(12) United States Patent
Holmes et al.

(10) Patent No.: US 9,176,126 B2
(45) Date of Patent: *Nov. 3, 2015

(54) SYSTEMS AND METHODS OF SAMPLE PROCESSING AND FLUID CONTROL IN A FLUIDIC SYSTEM

(71) Applicant: Theranos, Inc., Palo Alto, CA (US)

(72) Inventors: Elizabeth A. Holmes, Palo Alto, CA (US); Shaunak Roy, Palo Alto, CA (US); Ian Gibbons; Shize Daniel Qi, Palo Alto, CA (US); Edmond Ku, Palo Alto, CA (US); Chris Todd, Palo Alto, CA (US); Melissa Takahashi, Palo Alto, CA (US); Bruce Johnson, Palo Alto, CA (US); Jeff Fenton, Palo Alto, CA (US); Keith Moravick, Palo Alto, CA (US); Uwe Springborn, Palo Alto, CA (US); Anthony Delacruz, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/270,618

(22) Filed: May 6, 2014

(65) Prior Publication Data

US 2014/0329259 A1    Nov. 6, 2014

Related U.S. Application Data

(63) Continuation of application No. 11/554,509, filed on Oct. 30, 2006, now Pat. No. 8,741,230, which is a continuation-in-part of application No. 11/388,415, filed on Mar. 24, 2006, now Pat. No. 8,679,407, and a (Continued)

(51) Int. Cl.
*G01N 33/536* (2006.01)
*G01N 33/53* (2006.01)
(Continued)

(52) U.S. Cl.
CPC ............ *G01N 33/536* (2013.01); *A61B 5/1411* (2013.01); *A61B 5/1486* (2013.01);
(Continued)

(58) Field of Classification Search
CPC . G01N 33/00; G01N 33/5302; A61B 5/1411; A61B 5/1486; A61B 5/412
USPC ........... 422/500, 50, 68.1; 436/180, 164, 501; 435/15, 4
See application file for complete search history.

(56) References Cited

U.S. PATENT DOCUMENTS

| | | | |
|---|---|---|---|
| 4,003,379 A | 1/1977 | Ellinwood, Jr. | |
| 4,146,029 A | 3/1979 | Ellinwood, Jr. | |

(Continued)

FOREIGN PATENT DOCUMENTS

| | | |
|---|---|---|
| CN | 2559986 | 7/2003 |
| EP | 684315 A1 | 11/1995 |

(Continued)

OTHER PUBLICATIONS

Office Action dated Oct. 26, 2006 for U.S. Appl. No. 10/937,872.
(Continued)

*Primary Examiner* — Christine T Mui

(57) ABSTRACT

This invention is in the field of medical devices. Specifically, the present invention provides portable medical devices that allow real-time detection of analytes from a biological fluid. The methods and devices are particularly useful for providing point-of-care testing for a variety of medical applications.

13 Claims, 46 Drawing Sheets

Related U.S. Application Data continuation-in-part of application No. 11/389,410, filed on Mar. 24, 2006, now abandoned, and a continuation-in-part of application No. 11/388,823, filed on Mar. 24, 2006, and a continuation-in-part of application No. 11/388,723, filed on Mar. 24, 2006, now abandoned, and a continuation-in-part of application No. 11/388,824, filed on Mar. 24, 2006, now Pat. No. 7,888,125, and a continuation-in-part of application No. 11/389,409, filed on Mar. 24, 2006, now Pat. No. 7,635,594.

(51) Int. Cl.
- *A61B 5/1486* (2006.01)
- *A61B 5/15* (2006.01)
- *A61B 5/00* (2006.01)
- *G01N 33/573* (2006.01)

(52) U.S. Cl.
CPC ............... *A61B 5/412* (2013.01); *A61B 5/685* (2013.01); *G01N 33/5302* (2013.01); *G01N 33/573* (2013.01); *G01N 2333/46* (2013.01); *G01N 2333/91188* (2013.01); *G01N 2800/52* (2013.01)

(56) References Cited

U.S. PATENT DOCUMENTS

| | | |
|---|---|---|
| 4,347,176 A | 8/1982 | Mehta |
| 4,731,726 A | 3/1988 | Allen, III |
| 4,793,825 A | 12/1988 | Benjamin et al. |
| 4,910,131 A | 3/1990 | Mellman et al. |
| 4,920,213 A | 4/1990 | Dale et al. |
| 4,946,795 A | 8/1990 | Gibbons et al. |
| 5,039,617 A | 8/1991 | McDonald et al. |
| 5,089,229 A | 2/1992 | Heidt et al. |
| 5,104,813 A | 4/1992 | Besemer et al. |
| 5,130,238 A | 7/1992 | Malek et al. |
| 5,162,237 A | 11/1992 | Messenger et al. |
| 5,204,525 A | 4/1993 | Hillman et al. |
| 5,270,184 A | 12/1993 | Walker et al. |
| 5,273,905 A | 12/1993 | Muller et al. |
| 5,279,607 A | 1/1994 | Schentag et al. |
| 5,281,395 A | 1/1994 | Markart et al. |
| 5,310,652 A | 5/1994 | Gelfand et al. |
| 5,322,770 A | 6/1994 | Gelfand |
| 5,380,487 A | 1/1995 | Choperena et al. |
| 5,399,491 A | 3/1995 | Kacian et al. |
| 5,443,790 A | 8/1995 | Coeurveille et al. |
| 5,455,166 A | 10/1995 | Walker |
| 5,472,603 A | 12/1995 | Schembri |
| 5,480,784 A | 1/1996 | Kacian et al. |
| 5,527,670 A | 6/1996 | Stanley |
| 5,545,540 A | 8/1996 | Mian |
| 5,554,539 A | 9/1996 | Chadney et al. |
| 5,578,269 A | 11/1996 | Yaremko et al. |
| 5,624,850 A | 4/1997 | Kumar et al. |
| 5,670,375 A | 9/1997 | Seaton et al. |
| 5,674,698 A | 10/1997 | Zarling et al. |
| 5,716,852 A | 2/1998 | Yager et al. |
| 5,744,366 A | 4/1998 | Kricka et al. |
| 5,797,898 A | 8/1998 | Santini et al. |
| 5,801,057 A | 9/1998 | Smart et al. |
| 5,807,375 A | 9/1998 | Gross et al. |
| 5,820,548 A | 10/1998 | Sieben et al. |
| 5,832,296 A | 11/1998 | Wang et al. |
| 5,842,787 A | 12/1998 | Kopf-Sill et al. |
| 5,848,991 A | 12/1998 | Gross et al. |
| 5,854,033 A | 12/1998 | Lizardi |
| 5,874,214 A | 2/1999 | Nova et al. |
| 5,885,470 A | 3/1999 | Parce et al. |
| 5,902,549 A | 5/1999 | Mimura et al. |
| 5,939,291 A | 8/1999 | Loewy et al. |
| 5,942,443 A | 8/1999 | Parce et al. |
| 5,961,451 A | 10/1999 | Reber et al. |
| 5,961,923 A | 10/1999 | Nova et al. |
| 5,976,896 A | 11/1999 | Kumar et al. |
| 5,980,830 A | 11/1999 | Savage et al. |
| 6,033,850 A | 3/2000 | Purvis |
| 6,046,056 A | 4/2000 | Parce et al. |
| 6,074,616 A | 6/2000 | Buechler et al. |
| 6,123,861 A | 9/2000 | Santini, Jr. et al. |
| 6,156,181 A | 12/2000 | Parce et al. |
| 6,174,675 B1 | 1/2001 | Chow et al. |
| 6,176,962 B1 | 1/2001 | Soane et al. |
| 6,200,814 B1 | 3/2001 | Malmqvist et al. |
| 6,204,068 B1 | 3/2001 | Soini et al. |
| 6,221,677 B1 | 4/2001 | Wu et al. |
| 6,245,057 B1 | 6/2001 | Sieben et al. |
| 6,251,639 B1 | 6/2001 | Kurn |
| 6,267,858 B1 | 7/2001 | Parce et al. |
| 6,277,605 B1 | 8/2001 | Wijnhoven et al. |
| 6,299,839 B1 | 10/2001 | Karunaratne et al. |
| 6,319,668 B1 | 11/2001 | Nova et al. |
| 6,333,157 B1 | 12/2001 | Miller-Jones et al. |
| 6,340,588 B1 | 1/2002 | Nova et al. |
| 6,352,854 B1 | 3/2002 | Nova et al. |
| 6,361,958 B1 | 3/2002 | Shieh et al. |
| 6,368,275 B1 | 4/2002 | Sliwa et al. |
| 6,372,428 B1 | 4/2002 | Nova et al. |
| 6,375,469 B1 | 4/2002 | Brown |
| 6,410,278 B1 | 6/2002 | Notomi et al. |
| 6,429,025 B1 | 8/2002 | Parce et al. |
| 6,440,725 B1 | 8/2002 | Pourahmadi et al. |
| 6,464,687 B1 | 10/2002 | Ishikawa et al. |
| 6,477,394 B2 | 11/2002 | Rice et al. |
| 6,482,593 B2 | 11/2002 | Walt et al. |
| 6,491,666 B1 | 12/2002 | Santini et al. |
| 6,503,231 B1 | 1/2003 | Prausnitz et al. |
| 6,520,326 B2 | 2/2003 | McIvor et al. |
| 6,527,762 B1 | 3/2003 | Santini, Jr. et al. |
| 6,542,717 B1 | 4/2003 | Zimmerman et al. |
| 6,544,732 B1 | 4/2003 | Chee et al. |
| 6,551,838 B2 | 4/2003 | Santini, Jr. et al. |
| 6,591,124 B2 | 7/2003 | Sherman et al. |
| 6,632,216 B2 | 10/2003 | Houzego et al. |
| 6,649,358 B1 | 11/2003 | Parce et al. |
| 6,663,003 B2 | 12/2003 | Johnson et al. |
| 6,703,205 B2 | 3/2004 | Kopf-Sill et al. |
| 6,743,399 B1 | 6/2004 | Weigl et al. |
| 6,748,337 B2 | 6/2004 | Wardlaw et al. |
| 6,789,510 B1 | 9/2004 | Lee |
| 6,832,296 B2 | 12/2004 | Hooker |
| 6,849,237 B2 | 2/2005 | Housefield et al. |
| 6,878,755 B2 | 4/2005 | Singh et al. |
| 6,887,202 B2 | 5/2005 | Currie et al. |
| 6,915,679 B2 | 7/2005 | Chien et al. |
| 6,923,764 B2 | 8/2005 | Aceti et al. |
| 6,927,851 B2 | 8/2005 | McCaffrey et al. |
| 6,929,636 B1 | 8/2005 | von Alten |
| 6,942,771 B1 | 9/2005 | Kayyem |
| 6,946,251 B2 | 9/2005 | Kurn |
| 6,949,377 B2 | 9/2005 | Ho |
| 6,966,880 B2 | 11/2005 | Boecker et al. |
| 7,039,453 B2 | 5/2006 | Mullick et al. |
| 7,052,831 B2 | 5/2006 | Fletcher et al. |
| 7,105,183 B2 | 9/2006 | McGrath |
| 7,112,444 B2 | 9/2006 | Beebe et al. |
| 7,178,386 B1 | 2/2007 | Gamble et al. |
| 7,201,872 B2 | 4/2007 | Meron |
| 7,238,323 B2 | 7/2007 | Knapp et al. |
| 7,291,497 B2 | 11/2007 | Holmes et al. |
| 7,459,305 B2 | 12/2008 | Levy |
| 7,497,997 B2 | 3/2009 | Glezer et al. |
| 7,635,594 B2 | 12/2009 | Holmes et al. |
| 7,636,667 B2 | 12/2009 | Brown |
| 7,807,197 B2 | 10/2010 | Lee et al. |
| 7,824,890 B2 | 11/2010 | Hoser et al. |
| 8,055,329 B2 | 11/2011 | Kimchy et al. |
| 8,158,430 B1 | 4/2012 | Roy et al. |
| 8,202,492 B2 | 6/2012 | Linder et al. |
| 8,263,006 B2 | 9/2012 | Sutherland et al. |

(56) References Cited

U.S. PATENT DOCUMENTS

| | | |
|---|---|---|
| 8,318,109 B2 | 11/2012 | Saltsman et al. |
| 8,323,887 B2 | 12/2012 | Webster et al. |
| 8,889,083 B2 | 11/2014 | Ismagilov et al. |
| 2001/0019831 A1 | 9/2001 | Phillips et al. |
| 2001/0051340 A1 | 12/2001 | Singh et al. |
| 2001/0051766 A1 | 12/2001 | Gazdzinski |
| 2001/0053535 A1 | 12/2001 | Bashir et al. |
| 2002/0001854 A1 | 1/2002 | Lee |
| 2002/0034757 A1 | 3/2002 | Cubicciotti |
| 2002/0052761 A1 | 5/2002 | Fey et al. |
| 2002/0055094 A1 | 5/2002 | Reece et al. |
| 2002/0055127 A1 | 5/2002 | Gindilis |
| 2002/0059030 A1 | 5/2002 | Otworth et al. |
| 2002/0072733 A1 | 6/2002 | Flaherty |
| 2002/0092770 A1 | 7/2002 | Hedberg et al. |
| 2002/0110496 A1 | 8/2002 | Samsoondar |
| 2002/0114739 A1 | 8/2002 | Weigl et al. |
| 2002/0132226 A1 | 9/2002 | Nair et al. |
| 2002/0143437 A1 | 10/2002 | Handique et al. |
| 2003/0014362 A1 | 1/2003 | Yim |
| 2003/0017467 A1 | 1/2003 | Hooper et al. |
| 2003/0049833 A1 | 3/2003 | Chen et al. |
| 2003/0049865 A1 | 3/2003 | Santini et al. |
| 2003/0061687 A1 | 4/2003 | Hansen et al. |
| 2003/0069560 A1 | 4/2003 | Adamis et al. |
| 2003/0097092 A1 | 5/2003 | Flaherty |
| 2003/0104590 A1 | 6/2003 | Santini et al. |
| 2003/0117491 A1 | 6/2003 | Avni et al. |
| 2003/0143551 A1 | 7/2003 | Cattell |
| 2003/0148362 A1 | 8/2003 | Luka |
| 2003/0153900 A1 | 8/2003 | Aceti et al. |
| 2003/0167000 A1 | 9/2003 | Mullick et al. |
| 2003/0170705 A1 | 9/2003 | Schulman et al. |
| 2003/0185706 A1 | 10/2003 | Ribi |
| 2003/0191430 A1 | 10/2003 | D'Andrea et al. |
| 2003/0208113 A1 | 11/2003 | Mault et al. |
| 2003/0208133 A1 | 11/2003 | Mault |
| 2003/0210607 A1 | 11/2003 | Gilbert et al. |
| 2003/0211007 A1 | 11/2003 | Maus et al. |
| 2003/0211618 A1 | 11/2003 | Patel |
| 2003/0214057 A1 | 11/2003 | Huang |
| 2004/0005247 A1 | 1/2004 | Karp |
| 2004/0005582 A1 | 1/2004 | Shipwash |
| 2004/0014202 A1 | 1/2004 | King et al. |
| 2004/0033553 A1 | 2/2004 | Littarru et al. |
| 2004/0047767 A1 | 3/2004 | Bergman et al. |
| 2004/0053290 A1 | 3/2004 | Terbrueggen et al. |
| 2004/0058378 A1 | 3/2004 | Kong et al. |
| 2004/0086872 A1 | 5/2004 | Childers et al. |
| 2004/0096959 A1* | 5/2004 | Stiene et al. ............... 435/287.2 |
| 2004/0109793 A1 | 6/2004 | McNeely et al. |
| 2004/0121305 A1 | 6/2004 | Wiegand et al. |
| 2004/0122486 A1 | 6/2004 | Stahmann et al. |
| 2004/0157336 A1 | 8/2004 | Petroff et al. |
| 2004/0213825 A1 | 10/2004 | Levy |
| 2004/0228766 A1 | 11/2004 | Witty et al. |
| 2004/0260204 A1 | 12/2004 | Boecker et al. |
| 2005/0009101 A1 | 1/2005 | Blackburn |
| 2005/0019836 A1 | 1/2005 | Vogel et al. |
| 2005/0054078 A1 | 3/2005 | Miller et al. |
| 2005/0064529 A1 | 3/2005 | Kwon |
| 2005/0090726 A1 | 4/2005 | Ackerman |
| 2005/0100937 A1 | 5/2005 | Holmes |
| 2005/0106713 A1 | 5/2005 | Phan et al. |
| 2005/0112544 A1 | 5/2005 | Xu et al. |
| 2005/0130292 A1 | 6/2005 | Ahn et al. |
| 2005/0130321 A1 | 6/2005 | Nicholson et al. |
| 2005/0136548 A1 | 6/2005 | McDevitt et al. |
| 2005/0137481 A1 | 6/2005 | Sheard et al. |
| 2005/0147559 A1 | 7/2005 | von Alten |
| 2005/0159982 A1 | 7/2005 | Showalter et al. |
| 2005/0180891 A1 | 8/2005 | Webster et al. |
| 2005/0201892 A1 | 9/2005 | Taguchi et al. |
| 2005/0209565 A1 | 9/2005 | Yuzhakov et al. |
| 2005/0221281 A1 | 10/2005 | Ho |
| 2005/0249633 A1 | 11/2005 | Blatt et al. |
| 2005/0255001 A1 | 11/2005 | Padmanabhan et al. |
| 2005/0255600 A1 | 11/2005 | Padmanabhan et al. |
| 2006/0019319 A1 | 1/2006 | Billadeau et al. |
| 2006/0029924 A1 | 2/2006 | Brewster et al. |
| 2006/0062852 A1 | 3/2006 | Holmes |
| 2006/0078998 A1 | 4/2006 | Puskas et al. |
| 2006/0106316 A1 | 5/2006 | Palti |
| 2006/0160205 A1 | 7/2006 | Blackburn et al. |
| 2006/0177873 A1 | 8/2006 | Dowd et al. |
| 2006/0182738 A1 | 8/2006 | Holmes |
| 2006/0211933 A1 | 9/2006 | Zimmermann et al. |
| 2006/0257941 A1 | 11/2006 | McDevitt et al. |
| 2006/0264779 A1 | 11/2006 | Kemp et al. |
| 2006/0264780 A1 | 11/2006 | Holmes et al. |
| 2006/0264781 A1 | 11/2006 | Gibbons et al. |
| 2006/0264782 A1 | 11/2006 | Holmes et al. |
| 2006/0264783 A1 | 11/2006 | Holmes et al. |
| 2006/0292039 A1 | 12/2006 | Iida |
| 2007/0059196 A1 | 3/2007 | Brister et al. |
| 2007/0118399 A1 | 5/2007 | Avinash et al. |
| 2007/0166195 A1 | 7/2007 | Padmanabhan et al. |
| 2007/0224084 A1 | 9/2007 | Holmes et al. |
| 2007/0264629 A1 | 11/2007 | Holmes et al. |
| 2008/0009766 A1 | 1/2008 | Holmes et al. |
| 2008/0065420 A1 | 3/2008 | Tirinato et al. |
| 2008/0113391 A1 | 5/2008 | Gibbons et al. |
| 2009/0093970 A1 | 4/2009 | Lewy et al. |
| 2009/0318775 A1 | 12/2009 | Michelson et al. |
| 2010/0074799 A1 | 3/2010 | Kemp et al. |
| 2010/0081144 A1 | 4/2010 | Holmes et al. |
| 2010/0081894 A1 | 4/2010 | Zdeblick et al. |
| 2010/0152885 A1 | 6/2010 | Regan et al. |
| 2010/0184093 A1 | 7/2010 | Donovan et al. |
| 2010/0248277 A1 | 9/2010 | Gibbons et al. |
| 2011/0003699 A1 | 1/2011 | Yoder et al. |
| 2011/0104826 A1 | 5/2011 | Gibbons et al. |
| 2011/0166553 A1 | 7/2011 | Holmes et al. |
| 2011/0213564 A1 | 9/2011 | Henke |
| 2011/0213579 A1 | 9/2011 | Henke |
| 2011/0213619 A1 | 9/2011 | Henke |
| 2012/0034598 A1 | 2/2012 | Holmes et al. |
| 2012/0258472 A1 | 10/2012 | Roy et al. |
| 2013/0115685 A1 | 5/2013 | Holmes et al. |
| 2014/0222447 A1 | 8/2014 | Holmes et al. |

FOREIGN PATENT DOCUMENTS

| | | |
|---|---|---|
| EP | 1498067 | 1/2005 |
| JP | S6247555 A | 3/1987 |
| JP | H07304799 A | 11/1995 |
| JP | 2002511965 A | 4/2002 |
| JP | 2002538440 A | 11/2002 |
| JP | 2003167960 A | 6/2003 |
| JP | 2004527825 A | 9/2004 |
| JP | 2004317498 A | 11/2004 |
| JP | 2005130855 A | 5/2005 |
| JP | 2007187677 A | 7/2007 |
| WO | 9013668 A1 | 11/1990 |
| WO | 9401165 A | 1/1994 |
| WO | 0049176 A1 | 8/2000 |
| WO | 0135928 A | 5/2001 |
| WO | 0164344 A2 | 9/2001 |
| WO | 02064038 A | 8/2002 |
| WO | 03066128 A | 8/2003 |
| WO | 2005024437 A1 | 3/2005 |
| WO | 2005025413 A2 | 3/2005 |
| WO | 2005031355 A | 4/2005 |
| WO | 2005065157 A | 7/2005 |
| WO | 2005065538 A2 | 7/2005 |
| WO | 2005121367 A | 12/2005 |
| WO | 2006121510 A2 | 11/2006 |

(56) References Cited

FOREIGN PATENT DOCUMENTS

| WO | 2007120904 A | 10/2007 |
|---|---|---|
| WO | 2011106512 A | 9/2011 |
| WO | 2012040641 A | 3/2012 |

OTHER PUBLICATIONS

Office Action dated Oct. 31, 2013 for U.S. Appl. No. 12/986,954.
Office Action dated Oct. 6, 2008 for U.S. Appl. No. 11/746,535.
Office Action dated Nov. 22, 2011 for U.S. Appl. No. 11/202,231.
Office Action dated Nov. 5, 2009 for U.S. Appl. No. 11/202,231.
Office Action dated Nov. 9, 2011 for U.S. Appl. No. 11/388,823.
Office Action dated Dec. 11, 2012 for U.S. Appl. No. 12/750,518.
Office Action dated Dec. 19, 2008 for U.S. Appl. No. 11/202,206.
Office Action dated Dec. 22, 2009 for U.S. Appl. No. 11/388,823.
Office Action dated Dec. 22, 2010 for U.S. Appl. No. 11/554,509.
Office Action dated Dec. 9, 2013 for U.S. Appl. No. 12/625,430.
Office Action dated Feb. 1, 2013 for U.S. Appl. No. 13/187,960.
Office Action dated Feb. 17, 2009 for U.S. Appl. No. 11/202,231.
Office Action dated Feb. 2, 2011 for U.S. Appl. No. 11/746,535.
Office Action dated Feb. 22, 2008 for U.S. Appl. No. 11/202,231.
Office Action dated Feb. 22, 2008 for U.S. Appl. No. 11/746,535.
Office Action dated Feb. 27, 2009 for U.S. Appl. No. 11/388,723.
Office Action dated Mar. 16, 2011 for U.S. Appl. No. 11/202,231.
Office Action dated Mar. 17, 2009 for U.S. Appl. No. 11/388,415.
Office Action dated Mar. 18, 2008 for U.S. Appl. No. 11/202,206.
Office Action dated Mar. 21, 2008 for U.S. Appl. No. 11/388,723.
Office Action dated Mar. 21, 2011 for U.S. Appl. No. 11/388,415.
Office Action dated Mar. 22, 2010 for U.S. Appl. No. 11/202,206.
Office Action dated Mar. 3, 2011 for U.S. Appl. No. 11/202,206.
Office Action dated Mar. 5, 2009 for U.S. Appl. No. 11/388,823.
Office Action dated Mar. 5, 2010 for U.S. Appl. No. 11/746,535.
Office Action dated Mar. 7, 2006 for U.S. Appl. No. 10/937,872.
Office Action dated Apr. 1, 2010 for U.S. Appl. No. 11/388,824.
Office Action dated Apr. 13, 2012 for U.S. Appl. No. 11/554,509.
Office Action dated Apr. 18, 2007 for U.S. Appl. No. 10/937,872.
Office Action dated Apr. 29, 2009 for U.S. Appl. No. 11/389,409.
Office Action dated Apr. 30, 2009 for U.S. Appl. No. 11/388,824.
Office Action dated Apr. 30, 2013 for U.S. Appl. No. 13/647,325.
Office Action dated Apr. 4, 2013 for U.S. Appl. No. 12/986,954.
Office Action dated Apr. 5, 2010 for U.S. Appl. No. 11/554,509.
Office Action dated Apr. 8, 2009 for U.S. Appl. No. 11/389,410.
Office Action dated May 22, 2009 for U.S. Appl. No. 11/746,535.
Office Action dated May 29, 2012 for U.S. Appl. No. 12/986,954.
Office Action dated Jun. 1, 2007 for U.S. Appl. No. 11/389,409.
Office Action dated Jun. 1, 2012 for U.S. Appl. No. 11/388,823.
Office Action dated Jun. 11, 2012 for U.S. Appl. No. 11/388,415.
Office Action dated Jun. 11, 2014 for U.S. Appl. No. 12/625,430.
Office Action dated Jun. 12, 2014 for U.S. Appl. No. 12/986,954.
Office Action dated Jun. 21, 2007 for U.S. Appl. No. 11/202,231.
Office Action dated Jun. 24, 2013 for U.S. Appl. No. 13/436,568.
Office Action dated Jun. 5, 2013 for U.S. Appl. No. 12/750,518.
Office Action dated Jun. 9, 2010 for U.S. Appl. No. 11/746,535.
Office Action dated Jul. 18, 2012 for U.S. Appl. No. 12/576,197.
Office Action dated Jul. 25, 2008 for U.S. Appl. No. 11/389,409.
Office Action dated Jul. 27, 2011 for U.S. Appl. No. 11/554,509.
Office Action dated Jan. 13, 2015 for U.S. Appl. No. 13/647,325.
Office Action dated Dec. 3, 2014 for U.S. Appl. No. 12/625,430.
Office Action dated Jul. 28, 2009 for U.S. Appl. No. 11/202,206.
Office Action dated Jul. 29, 2011 for U.S. Appl. No. 12/986,954.
Office Action dated Aug. 24, 2010 for U.S. Appl. No. 11/388,415.
Office Action dated Aug. 27, 2010 for U.S. Appl. No. 11/388,823.
Office Action dated Aug. 29, 2008 for U.S. Appl. No. 11/388,823.
Office Action dated Aug. 31, 2011 for U.S. Appl. No. 12/221,816.
Office Action dated Sep. 1, 2005 for U.S. Appl. No. 10/937,872.
Office Action dated Sep. 11, 2008 for U.S. Appl. No. 11/389,409.
Office Action dated Sep. 22, 2011 for U.S. Appl. No. 12/576,197.
Office Action dated Sep. 4, 2013 for U.S. Appl. No. 11/388,823.
Office Action dated Sep. 5, 2008 for U.S. Appl. No. 11/388,723.

Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05.
Pal, et al. An integrated microfluidic device for influenza and other genetic analyses. Lab Chip. Oct. 2005;5(10):1024-32. Epub Aug. 18, 2005.
Patolsky, et al. Electrical detection of single viruses. Proc Natl Acad Sci USA. Sep. 28, 2004;101(39):14017-22. Epub Sep. 13, 2004.
Pescovitz, D. Sniffing out airborne disease. Lab Note: Research from the College of Engineering, University of California, Berkeley, 2004. Available online at http://www.coe.berkeley.edu/labnotes/0904/pisano.html. Accessed Jan. 28, 2011.
Preininger, et al. Polymer-coated optical fibres for application in a direct evanescent wave immunoassay. Analytica Chimica Acta, 2000; 403; 67-76.
Rai-Choudhury, ed., Handbook of Microlithography, Micromachining & Microfabrication. SPIE Optical Engineering Press. Bellingham, Wash. 1997. (Cover pages and table of contents only).
Ray, et al. Distinct hemagglutinin and neuraminidase epitopes involved in antigenic variation of recent human parainfluenza virus type 2 isolates. Virus Res. Jun. 1992;24(1):107-13.
Red Herring. Stopping bad reactions. Red Herring. Dec. 26, 2005.
Runyan, et al. Seminconductor integrated circuit processing technology. Addison-Wesley Publishing Co., Reading Mass. 1990. (Cover pages and table of contents only).
Sambrook, et al. Molecular Cloning: A Laboratory Manual. Cold Spring Harbor Laboratory Press. New York. 2001. (Cover pages and table of contents only).
Sapsford, et al. Demonstration of four immunoassay formats using the array biosensor. Anal Chem. 2002; 74 (5):1061-8.
Scheurle, et al. HER-2/neu expression in archival non-small cell lung carcinomas using FDA-approved hercep test. Anticancer Res. 2000; 20:2091-2096.
Spira, et al. The identification of monoclonal class switch variants by sib selection and an ELISA assay. J Immunol Methods. 1984;74(2):307-15.
Steplewski, et al. Isolation and characterization of anti-monosialoganglioside monoclonal antibody 19-9 class-switch variants. Proc Natl Acad Sci U S A. 1985; 82(24):8653-7.
Stevens, et al. Glycan microarray analysis of the hemagglutinins from modern and pandemic influenza viruses reveals different receptor specificities. J Mol Biol. Feb. 3, 2006;355(5):1143-55.
Tautz. Hypervariability of simple sequences as a general source for polymorphic DNA markers. Nucleic Acids Res. Aug. 25, 1989;17(16):6463-71.
Tedeschi, et al. Antibody immobilisation on fibre optic TIRF sensors. Biosens Bioelectron. 2003; 19(2):85-93.
U.S. Appl. No. 13/286,168, filed Oct. 31, 2011. Inventors: Holmes et al.
U.S. Appl. No. 13/366,193, filed Feb. 3, 2012. Inventors: Holmes et al.
U.S. Appl. No. 13/629,577, filed Sep. 27, 2012. Inventors: Holmes et al.
U.S. Appl. No. 13/896,171, filed May 16, 2013. Inventors: Holmes, et al.
U.S. Appl. No. 14/050,235, filed Oct. 9, 2013. Inventors: Holmes, et al.
Weber, et al. Abundant class of human DNA polymorphisms which can be typed using the polymerase chain reaction. Am J Hum Genet. Mar. 1989;44(3):388-96.
Williams, et al. DNA polymorphisms amplified by arbitrary primers are useful as genetic markers. Nucleic Acids Res. Nov. 25, 1990;18(22):6531-5.
Yan, et al. Multiplexed flow cytometric immunoassay for influenza virus detection and differentiation. Anal Chem. Dec. 1, 2005;77(23):7673-8.
Zhao, et al. Phylogenetic distribution and genetic mapping of a (GGC)n microsatellite from rice (*Oryza sativa* L.). Plant Mol Biol. Feb. 1993;21(4):607-14.
Zietkiewicz, et al. Genome fingerprinting by simple sequence repeat (SSR)-anchored polymerase chain reaction amplification. Genomics. Mar. 15, 1994;20(2):176-83.

(56) References Cited

OTHER PUBLICATIONS

Abbott. FDA Clears Abbott's i-STAT 1 Wireless Point of Care Testing System. Press release dated Mar. 29, 2011.
Abbott. Procedure Manual for the i-STAT System. Rev. dated Jul. 12, 2004.
Abbott. Testing Cartridges for the i-STAT System. Rev. B. Jun. 2009. Available at http://www.abbottpointofcare.com/PDFs/17845_CrtrdgeBrochure_M1.pdf. Accessed Sep. 13, 2011.
Bawendi, et al. The quantum-mechanics of larger semiconductor clusters. Annu. Rev. Phys. Chem. 1990; 41:477-496.
BD Biosciences, Directigen FluA&B Assay Manual. Oct. 11, 2016, pp. 1-11.
Beier, et al. Versatile derivatisation of solid support media for covalent bonding on DNA-microchips. Nucleic Acids Res. 1999; 27:1970-1977.
Bes, et al. Mapping the paratope of anti-CD4 recombinant Fab 13B8.2 by combining parallel peptide synthesis and site-directed mutagenesis. J Biol Chem. Apr. 18, 2003;278(16):14265-73.
Bhatia, et al. Use of thiol-terminal silanes and heterobifuntional crosslinkers for immobilization of antibodies on silica surfaces. Anal Biochem. 1989; 178(2):408-13.
Botstein, et al. Construction of a genetic linkage map in man using restriction fragment length polymorphisms. Am J Hum Genet. May 1980;32(3):314-31.
Broadcaster Moira Gunn with Elizabeth Holmes, recorded Mar. 5, 2005 on Biotech Nation.
Bruchez, et al. Semiconductor nanocrystals as fluorescent biological labels. Science. 1998; 281(5385):2013-6.
Celebre, et al. A comparative sudy of efficiencies of fibre optic and prism TIRF sensors. Meas. Sci. Technol. 1992; 3:1166-1173.
Chan. Quantum dot bioconjugates for ultrasensitive nonisotopic detection. Science. 1998;281(5385):2016-8.
Chang, et al. Micromachining & Microfabrication. SPIE Optical Engineering Press. Bellingham, Wash. 1997. (Cover pages and table of contents only).
Charles, et al. Synthesis of a flurescent analog of polychlorinated biphenyls for use in a continuous flow immunosensor assay. Bioconjug Chem. 1995; 6(6):691-4.
Di Serio, et al. Integration between the tele-cardiology unit and the central laboratory: methodological and clinical evaluation of point-of-care testing cardiac marker in the ambulance. Clin Chem Lab Med. 2006;44(6):768-73.
Duffy, et al. Rapid Prototyping of Microfluidic Systems in Poly(dimethylsiloxane). Analytical Chemistry. 1998; 70 (23);4974-4084.
European search report and search opinion dated Feb. 7, 2012 for EP Application No. 11180769.9.
European search report and search opinion dated Mar. 6, 2012 for EP Application No. 10179887.4.
European search report and search opinion dated May 29, 2012 for EP Application No. 11180769.9.
European search report dated Jun. 2, 2009 for Application No. 07762092.
Gavin, et al. Review of Rapid Diagnostic Tests for Influenza. Clinical and Applied Immunology Reviews. 2004; 4 (3):151-172.
Geddes, et al. The impedance of stainless-steel electrodes. Med Biol Eng. Sep. 1971;9(5):511-21.
Guatelli, et al. Isothermal, in vitro amplification of nucleic acids by a multienzyme reaction modeled after retroviral replication. Proc. Natl. Acad. Sci. USA. 1990;87:1874-1878.

Harlow, et al. Antibodies: A Laboratory Manual. Cold Spring Harbor Laboratory. New York. 1988. (Cover pages and table of contents only).
Harrison's Principles of Internal Medicine, Part 2 Cardinal Manifestations of Disease, Ch. 60 (12th ed. 1991; pp. 338-343.).
Health Buddy device. Available at http://www.3hc.org/images/2009%20images/health-buddy-appliance.gif. Accessed Aug. 26, 2011.
Health Buddy Health Management Programs. Available at http://www.bosch-telehealth.com/content/language1/img_zoom/health_buddy_system.gif. Accessed Aug. 26, 2011.
Hirsh, et al. The electrical conductivity of blood. I: Relationship to erythrocyte concentration. Blood. Nov. 1950;5 (11):1017-35.
International search report and written opinion dated Sep. 16, 2008 for PCT/US2007/009878.
International search report dated Jan. 22, 2008 for PCT/US06/42563.
International search report dated Dec. 8, 2008 for PCT/US06/11090.
International search report dated Jul. 4, 2005 for PCT/US04/029462.
International search report dated Aug. 11, 2008 for PCT/US07/68665.
International search report dated Sep. 9, 2008 for PCT/US07/23904.
Jaeger. Introduction to Microelectronic fabrication. Addison-Wesley Publishing Co. Reading Mass. 1988. (Cover pages and table of Contents only).
Kessler, et al. Use of the DNA flow-thru chip, a three-dimensional biochip, for typing and subtyping of influenza viruses. J Clin Microbiol. May 2004;42(5):2173-85.
Khan, et al. Detection of influenza virus neuraminidase-specific antibodies by an enzyme-linked immunosorbent assay. J Clin Microbiol. Jul. 1982;16(1):115-22.
Kilbourne, et al. Independent and disparate evolution in nature of influenza A virus hemagglutinin and neuraminidase glycoproteins. Proc Natl Acad Sci U S A. Jan. 1990;87(2):786-90.
Kwok, et al. Increasing the information content of STS-based genome maps: identifying polymorphisms in mapped STSs. Genomics. Jan. 1, 1996;31(1):123-6.
Landgren. Molecular mechanics of nucleic acid sequence amplification. Trends Genet. Jun. 1993;9(6):199-204.
Lee, et al. Microfluidic enzyme-linked immunosorbent assay technology. Adv Clin Chem. 2006;42:255-95.
Liu, et al. Validation of a fully integrated microfluidic array device for influenza A subtype identification and sequencing. Anal Chem. Jun. 15, 2006;78(12):4184-93.
Lizardi, et al. Exponential amplification of recombinant-RNA hybridization probes. BioTechnol. 1988; 6:1197-1202.
Lupiani, et al. Improved diagnostic tests for Avian influenza surveillance, 2005. Proceedings of the Institute of Food Technologies' First Annual Forod protection and Defense Research Conference.
Mohapatra, et al. Blood resistivity and its implications for the calculation of cardic output by the thoracic electrical impedance technique. Intensive Care Med. Aug. 1977;3(2):63-7.
Mukerjee, et al. Microneedle array for transdermal biological fluid extraction and in situ analysis. Sensors and Actuators A. 2004; 114:267-275.
Office Action dated Jan. 5, 2010 for U.S. Appl. No. 11/388,415.
Office Action dated Jan. 8, 2013 for U.S. Appl. No. 11/388,415.
Office Action dated Oct. 17, 2008 for U.S. Appl. No. 11/389,410.
Notice of Allowance dated May 14, 2015 for U.S. Appl. No. 12/625,430.
Office Action dated Feb. 9, 2015 for U.S. Appl. No. 12/986,954.
Office Action dated Jun. 19, 2015 for U.S. Appl. No. 13/647,325.

* cited by examiner

Prior Art

6

22

22

Typical assay dose-response data for a two-step assay for TxB2

Dose responses computed with and without errors in calibration parameters.

Computed concentration errors produced by 1% mis-estimation of A and D calibration values Calibration using a "differential" approach Verification of calibration using the "1-point spike" method (log scale)

Verification of calibration using the "1-point spike" method (linear scale)

Dose-response of assays calibrated against a plasma sample with a very low TxB2 concentration Using spike recovery to eliminate calibration errors of the "C" parameter.

Calculating difference in concentration between two samples

Assay of plasma samples

Time course of assay signal generation

Impact of change in calibration parameter A on assay calibration

| Subject | Candidate output parameter | | | | | Input parameter | | | | |
|---|---|---|---|---|---|---|---|---|---|---|
| | OP1 | OP2 | OP3 | . | OPn | IP1 | IP2 | IP3 | . | IPn |
| 1 | | | | | | | | | | |
| 2 | | | | | | | | | | |
| 3 | | | | | | | | | | |
| . | | | | | | | | | | |
| . | | | | | | | | | | |
| N | | | | | | | | | | |

Figure 33

Computing the Therapeutic Index (TI)

Multiple Regression Analysis of the Computed TI

Illustration of the relationship between measured drug, analyte and biomarker concentration and therapeutic index.

Illustration of the application of this invention to minimize ADRs.

User Enter Food

Enter Food and Servings

Food Name: peach

Amount: 1    serving

Enter a food.

Date: January  1, 2004
Time: 0  :00

[Set to Now]

[Submit] [Reset Form] [Commit] [Cancel]

Food Values

| Amount | Units | Food | Cal. | Fat | Sat.Fat | Carb | Prot. |
|---|---|---|---|---|---|---|---|
| 1 | sv | Banana | 105 | 0 | 0 | 26 | 1 |
|  |  | Totals | 105 | 0 | 0 | 26 | 1 |

Figure 38

Patient input values

Use of TI to follow treatment progression in an autism patient

SYSTEMS AND METHODS OF SAMPLE PROCESSING AND FLUID CONTROL IN A FLUIDIC SYSTEM

BACKGROUND OF THE INVENTION

The discovery of a vast number of disease biomarkers and the establishment of miniaturized microfluidic systems have opened up new avenues to devise methods and systems for the prediction, diagnosis and treatment of diseases in a point-of-care setting. Point-of-care testing is particularly desirable because it rapidly delivers results to medical practitioners and enables faster consultation. Early diagnosis allows a practitioner to begin treatment sooner and thus avoiding unattended deterioration of a patient's condition. Examples of point-of-care analyses include tests for glucose, drugs of abuse, serum cholesterol, pregnancy, and ovulation. However, these and other currently available point-of-care methods and systems do not provide an integrated solution for sample acquisition, testing, analysis and communication of results to medical practitioners or health providers when needed. Thus, there remains a considerable need for a portable, multi-parameter measurement instrument that provides convenient and rapid data collection, transmission, analysis, as well as on-line medical consultation or decision making.

New and improved point-of-care testing is also needed for research and development of therapeutic agents as well as for monitoring possible adverse drug reactions (ADRs), after a drug is brought to the market place.

The safety and efficacy of a drug is determined by the pharmacokinetic (what the body does to the drug) and pharmacodynamic parameters (what the drug does to the body) of the drug. Currently, the pharmacokinetic (PK) and pharmacodymanic (PD) parameters of a drug are generally determined by first drawing blood samples from a patient followed by laboratory analyses. Such approach has numerous shortcomings. First, the patient is generally required to visit a clinic to provide clinical samples such as blood or urine samples at multiple time points. Second, most of the analytical techniques for determining target analyte and biomarker concentrations that reflect either the pharmacokinetic (PK) and pharmacodymanic (PD) parameters require that the blood samples be pre-processed before the parameters can be determined. This results in delay of data response, variability in physiological drug distribution and metabolism (warranting poor dosing), sparse sampling, and the lack of dosing history. Notably, numerous clinical trials often suffer from insufficient numbers of blood tests because of poor patient compliance; the patients often fail to return to a phlebotomist to provide the blood samples required by the trial.

Similarly, the current techniques and systems for monitoring ADRs are also inadequate. ADRs are one of the leading causes of morbidity and mortality in health care. The Institute of Medicine reported in January 2000 that 44,000 to 98,000 deaths occurred due to medical errors, of which 7,000 deaths were due to ADRs. Other studies conducted on hospitalized patient populations have indicated an ever higher overall incidence of several ADRs. Several reasons contribute to the prevalence of ADRs. First, there are more combination therapies available to patients. Second, there is an increasing trend towards chronic use of drugs (statins such as Lipitor and Cox-2 inhibitors such as Vioxx). Chronic use of drugs also increases the chance that changes in the patient's lifestyle, health status and use of other medications will occur. In women, the chronic use of drugs can result in unanticipated consequences if the woman becomes pregnant. Such risks are of particular concern to the fetus, which is especially susceptible to ADRs including teratogenicity.

A further important factor in managing the risks and benefits of drug therapy is patient compliance. Patients often fail to take scheduled dose of drug, take more than the prescribed dose, or fail to complete a course of drug therapy (especially common in treatment for infectious disease). These behaviors (deliberate or inadvertent) result in improper levels of drugs in the body which can cause serious adverse effects. The patient is typically oblivious to such consequences and the prescribing physician is also unlikely to realize the problem before several consequences occur.

Thus, there remains a pressing need for methods and apparatus that allow real-time data transmission between patient and medical practitioners to enable efficient communication and high throughput point-of-care testing in an ambulatory context. A beneficial system will detect ADRs, and efficacy and/or toxicity of a therapeutic agent in real-time in an ambulatory setting. It may also facilitate medical practitioners assessing patients' physiological conditions in response to therapeutic agents during the course of clinical trials or follow-on treatments. The present invention satisfies these needs and provides related advantages as well.

SUMMARY OF THE INVENTION

One aspect of the present invention is a fluidic device for detecting the presence or absence of an analyte in a bodily fluid from a subject. The fluidic device comprises a cartridge which comprises a sample collection unit and an assay assembly. The sample collection unit is configured to collect a sample of bodily fluid from the subject and deliver a predetermined portion of the sample to the assay assembly, and the assay assembly comprises at least one reaction site containing a reactant that reacts with the analyte to yield a signal indicative of the presence of the analyte.

In some embodiments the sample collection unit comprises a sample collection well in fluid communication with a metering channel, configured so that a collected sample flows from the sample collection well into the metering channel, and a metering element. The metering element is adapted to close the fluid communication of the sample collection well to the metering channel, thereby isolating a specific volume of the sample in the metering channel.

In some embodiments the metering element comprises a pin configured to be movable from an open position to a closed position. In the closed position the pin can block the metering channel. The pin can be moved from the open position to the closed position by an actuator in a device in which the cartridge can be inserted.

In some embodiments the sample collection unit further comprises a dilution chamber in fluidic communication with the metering channel, wherein the dilution chamber is configured to store a diluent and comprises a port for engaging pressure means for transferring said diluent from the dilution chamber into the metering channel.

In some embodiments the sample collection unit further comprises a mixing chamber in fluidic communication with the metering channel, the mixing chamber is configured to mix the predetermined portion of the sample with the diluent to yield a diluted sample. The mixing chamber can comprise a movable mixing element that causes the mixing of the predetermined portion of the sample with the diluent. In some embodiments the movable mixing element is magnetically controlled.

In some embodiments the sample collection unit further comprising a filter configured to filter the diluted sample before it is assayed.

In some embodiments the predetermined portion of the sample is less than about 50 ul. In some embodiments the predetermined portion of the sample is less than about 20 ul. In some embodiments the predetermined portion of the sample is about 10 ul.

In some embodiments the assay assembly is adapted to run an immunoassay.

In some embodiments the assay assembly comprises at least one reagent chamber in fluidic communication with the at least one reaction site, wherein the reagent chamber is configured to store an assay reagent.

One aspect of the invention is a fluidic device for detecting an analyte in a bodily fluid from a subject. The fluidic device comprises a cartridge including a sample collection unit, wherein the sample collection unit is configured to collect a sample of bodily fluid from the subject, and an assay assembly. The assay assembly comprises at least one reaction site in fluidic communication with the sample collection unit. The reaction site contains a reactant that reacts with the analyte to yield a signal indicative of the presence of the analyte. The assay assembly also comprises at least one reagent chamber in fluidic communication with the at least one reaction site, wherein the reagent chamber is configured to store an assay reagent. The assay assembly also comprises a fluidic channel connecting the reagent chamber with the reaction site. In addition, the assay assembly includes an actuatable valve assembly configured to control the flow of reagent through said fluidic channel, wherein the valve assembly comprises a sealing element and actuator element. The fluidic channel includes first and second locations, wherein the sealing element positioned in the first location obstructs the flow of fluid through the channel and the sealing element positioned in the second location allows the flow of fluid through the channel, and wherein the actuator element is adapted to move the sealing element from the first location to the second location.

In some embodiments the actuator element is not adapted to move the sealing element from the second location to the first location. In some embodiments the actuator element is adapted to be actuated by an actuator in a device in which the cartridge can be inserted. The actuator element can be adapted to be mechanically actuated by the actuator.

In some embodiments the second location has a larger cross section than the first location. The sealing element can be substantially sphere shaped and the actuator element can be substantially pin-shaped.

In some embodiments the actuator element comprises a sealing member such that when said actuator element moves the sealing element the sealing member forms a substantially air tight seal such that said fluid can only flow through said channel. The actuator element can be substantially pin shaped and the sealing member can be an O-ring adapted to be placed around the actuator element.

In some embodiments the assay assembly is adapted to run an immunoassay.

In some embodiments the sample of bodily fluid is less than about 50 ul. In some embodiments the sample of bodily fluid is less than about 20 ul. In some embodiments the sample of bodily fluid is about 10 ul.

One aspect of the invention is a system for detecting an analyte in a bodily fluid from a subject. The system comprises a fluidic device, a reader assembly comprising a detection assembly for detecting the signal, and a communication assembly for transmitting the signal to an external device.

In some embodiments the assay assembly is adapted to run an assay based on an assay protocol transmitted from the external device. The assay protocol can be transmitted wirelessly from said external device.

In some embodiments the fluidic device includes an identifier to provide the identity of said fluidic device that is adapted to trigger the transmission of the assay protocol. The assay protocol can vary depending on the identify of the fluidic device that is recognizable by an identifier detector.

In some embodiments the system is adapted to monitor more than one pharmacological parameter useful for assessing efficacy and/or toxicity of a therapeutic agent.

In some embodiments the system is adapted to automatically monitor patient compliance with a medical treatment involving a therapeutic agent.

In some embodiments, the assay assembly includes a waste chamber, the waste chamber comprising an optical quenching agent that reduces interfering signals generated from unbound reactants.

One aspect of the invention is a method of detecting an analyte in a bodily fluid from a subject. The method comprises providing a fluidic device comprising a cartridge, the cartridge comprising a sample collection unit and an assay assembly, wherein the sample collection unit is configured to collect a sample of bodily fluid from said subject, and wherein the assay assembly comprises at least one reaction site containing a reactant adapted to reacts with said analyte, metering a predetermined portion of the sample to be assayed in the sample collection unit, allowing the predetermined portion of sample to react with assay reagents contained within the assay assembly to yield a signal indicative of the presence of the analyte in the sample, and detecting the signal generated from the analyte collected in the sample of bodily fluid.

In some embodiments the method also comprises mixing the predetermined portion of the sample with a diluent in the fluidic device after the metering step. The mixing can include diluting the predetermined portion of the sample with the diluent to yield a diluted sample.

In some embodiments the method also includes filtering the diluted sample before allowing the predetermined portion of sample to react with assay reagents.

In some embodiments the assay assembly comprises at least one reagent chamber and an actuatable valve assembly configured to control flow of the reagents out of the reagent chamber and into the at least one reaction site. The method can also include actuating the actuatable valve assembly to permit the reagent to flow from the reagent chamber to the reaction site.

In some embodiments the actuatable valve assembly comprises an actuator pin and a sealing ball, and the actuating comprises actuating the actuator pin to displace the sealing ball.

In some embodiments the method includes quantifying the amount of the analyte present in the bodily fluid after the detecting step. The method may further include the step of comparing the amount of the analyte present in the biologic fluid to a predetermined amount of the analyte. In some embodiments the fluidic device communicates data relating to the signal via a wireless transmitter to an external device.

In some embodiments the analyte detected is indicative of at least one pharmacological parameter.

In some embodiments the method includes cross-referencing medical records of the subject with the at least one pharmacological parameter to assistant a clinician in providing an individualized medical treatment.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 33 shows how a reference therapeutic index would be computed.

FIG. 38 shows exemplary patient input values.

DETAILED DESCRIPTION OF THE INVENTION

System

Figure 1:
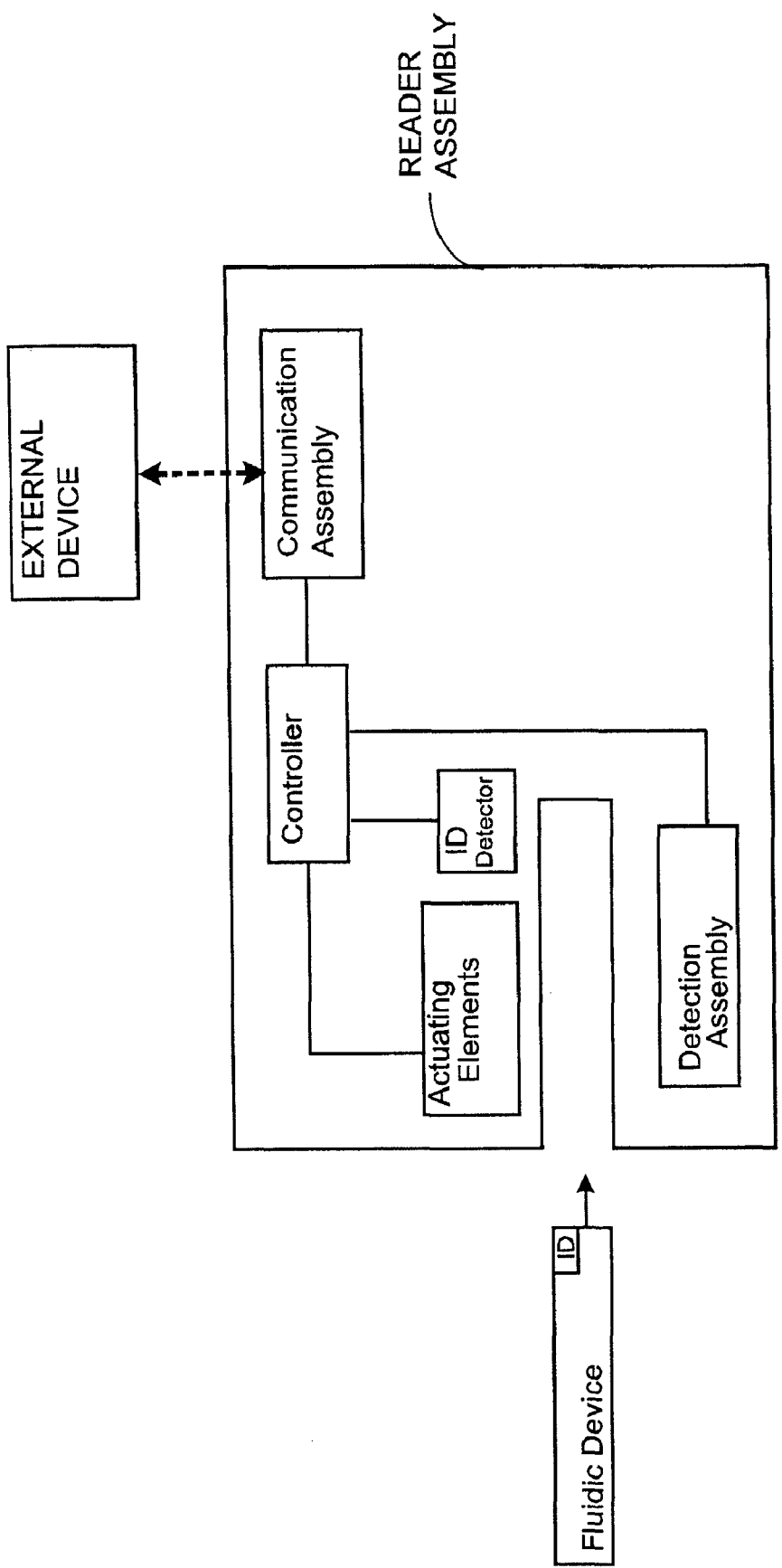
FIG. 1 is one embodiment showing multiple components of the present system.

One aspect of the present invention is a system for detecting an analyte in a sample of bodily fluid. The system is capable of detecting and/or quantifying analytes that are associated with specific biological processes, physiological conditions, disorders or stages of disorders.

The subject system comprises a fluidic device having one or more of the following components: a sample collection unit, an assay assembly, a reader assembly, and a communication assembly. The sample collection unit typically allows a sample of bodily fluid collected from a subject to react with reactants contained within the assay assembly for generating a signal indicative of the presence of the analyte of interest. The reader assembly detects the signal, which is then transmitted via the communication assembly to an external device for further processing.

Any bodily fluids suspected to contain an analyte of interest can be used in conjunction with the subject system or devices. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

In some embodiments, the bodily fluids are used directly for detecting the analytes present therein with the subject fluidic device without further processing. Where desired, however, the bodily fluids can be pre-treated before performing the analysis with the subject fluidic devices. The choice of pre-treatments will depend on the type of bodily fluid used and/or the nature of the analyte under investigation. For instance, where the analyte is present at low level in a sample of bodily fluid, the sample can be concentrated via any conventional means to enrich the analyte. Methods of concentrating an analyte include but are not limited to drying, evaporation, centrifugation, sedimentation, precipitation, and amplification. Where the analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufactures. Where the analyte is a molecule present on or within a cell, extraction can be performed using lysing agents including but not limited to denaturing detergent such as SDS or non-denaturing detergent such as thesit, sodium deoxylate, triton X-100, and tween-20.

In some embodiments, pretreatment can include diluting and/or mixing the sample, and filtering the sample to remove, e.g., red blood cells from a blood sample.

The volume of bodily fluid to be used with a fluidic device of the present invention is generally less than about 500 microliters, typically between about 1 to 100 microliters. Where desired, a sample of 1 to 50 microliters or 1 to 10 microliters can be used for detecting an analyte using the subject fluidic device.

A bodily fluid may be drawn from a patient and brought into the fluidic device in a variety of ways, including but not limited to, lancing, injection, or pipetting. In one embodiment, a lancet punctures the skin and draws the sample into the fluidic device using, for example, gravity, capillary action, aspiration, or vacuum force. The lancet may be part of the fluidic device, or part of a reader assembly, or as a stand alone component. Where needed, the lancet may be activated by a variety of mechanical, electrical, electromechanical, or any other known activation mechanism or any combination of such methods. In another embodiment where no active mechanism is required, a patient can simply provide a bodily fluid to the fluidic device, as for example, could occur with a saliva sample. The collected fluid can be placed in the sample collection unit within the fluidic device. In yet another embodiment, the fluidic device comprises at least one microneedle which punctures the skin. The microneedle can be used with a fluidic device alone, or can puncture the skin after the fluidic device is inserted into a reader assembly.

In some embodiments a microneedle is about the size of a human hair and has an integrated microreservoir or cuvette. The microneedle may painlessly penetrate the skin and draw a small blood sample. More preferably, the microneedle collects about 0.01 to about 1 microliter, preferably about 0.05 to about 0.5 microliters and more preferably about 0.1 to about 0.3 microliters of capillary blood. In some embodiments a microneedle may be constructed out of silicon and is about 10 to about 200 microns in diameter, preferably about 50 to about 150 microns in diameter, and most preferably about 100 microns in diameter, making their application to the skin virtually painless. To ensure that a capillary is actually struck by a needle, a plurality of microneedles may be used for sample collection. Such microneedles may be of the type marketed by Pelikan (Palo Alto, Calif.) and/or Kumetrix (Union City, Calif.). U.S. Pat. No. 6,503,231 discloses microneedles which may be used with the present invention.

Microfabrication processes that may be used in making the microneedles disclosed herein include without limitation lithography; etching techniques such as wet chemical, dry, and photoresist removal; thermal oxidation of silicon; electroplating and electroless plating; diffusion processes such as boron, phosphorus, arsenic, and antimony diffusion; ion implantation; film deposition such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997). Alternatively, microneedles may be molded in silicon wafers and then plated using conventional wire cutting techniques with nickel, gold, titanium or various other biocompatible metals. In some embodiments microneedles can be fashioned from biopolymers. In some embodiments microneedles may be fabricated and employed for the claimed devices according to the methods of Mukerjee et al., Sensors and Actuators A: Physical, Volume 114, Issues 2-3, 1 Sep. 2004, Pages 267-275.

In preferred embodiments a microneedle is only used once and then discarded. In some embodiments a mechanical actuator can insert and withdraw the microneedle from the patient, discard the used needle, and reload a new microneedle. The mechanical technologies developed and manufactured in very high volumes for very small disk drives have a similar set of motion and low cost requirements. In preferred embodiments the actuator is a MEMS (micro machined electromechanical system) device fabricated using semiconductor-like batch processes. Such actuators include without limitation nickel titanium alloy, neumatic, or piezo electric devices. In some embodiments the microneedles are about 1 micron to about 10 microns in thickness, preferably about 2 microns to about 6 microns in thickness, and most preferably about 4 microns in thickness. In some embodiments the microneedles are about 10 microns to about 100 microns in height, preferably about 30 microns to about 60 microns in height, and most preferably about 40 microns in height.

FIG. 1 illustrates an exemplary system of the present invention. As illustrated, a fluidic device provides a bodily fluid from a patient and can be inserted into a reader assembly. The fluidic device may take a variety of configurations and in some embodiments the fluidic device may be in the form of a cartridge. An identifier (ID) detector may detect an identifier on the fluidic device. The identifier detector communicates with a communication assembly via a controller which transmits the identifier to an external device. Where desired, the external device sends a protocol stored on the external device to the communication assembly based on the identifier. The protocol to be run on the fluidic device may comprise instructions to the controller of the reader assembly to perform the protocol on the fluidic device, including but not limited to a particular assay to be run and a detection method to be performed. Once the assay is performed on the fluidic device, a signal indicative of an analyte in the bodily fluid sample is generated and detected by a detection assembly. The detected signal may then be communicated to the communications assembly, where it can be transmitted to the external device for processing, including without limitation, calculation of the analyte concentration in the sample.

Figure 2:
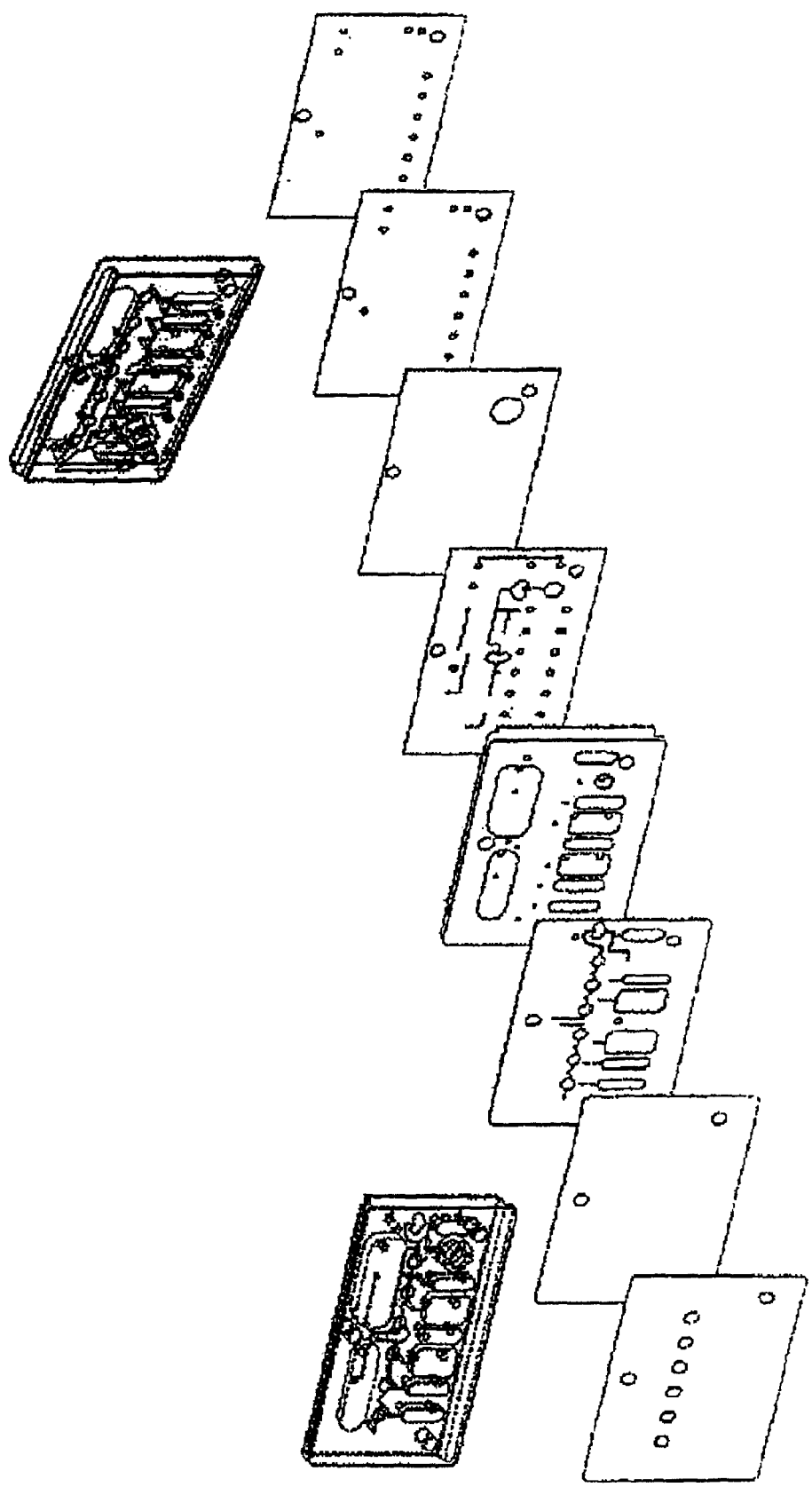
FIG. 2 shows different layers of an exemplary fluidic device prior to assembly.
Figure 3:
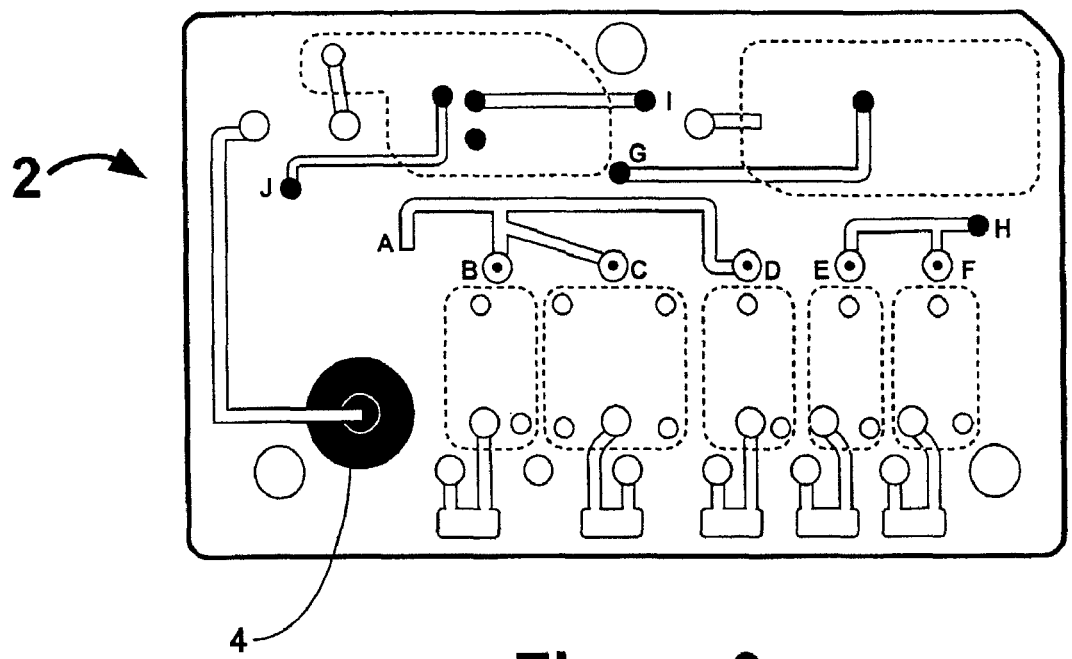
FIGS. 3 and 4 illustrate the fluidic network within an exemplary fluidic device.
Figure 4:
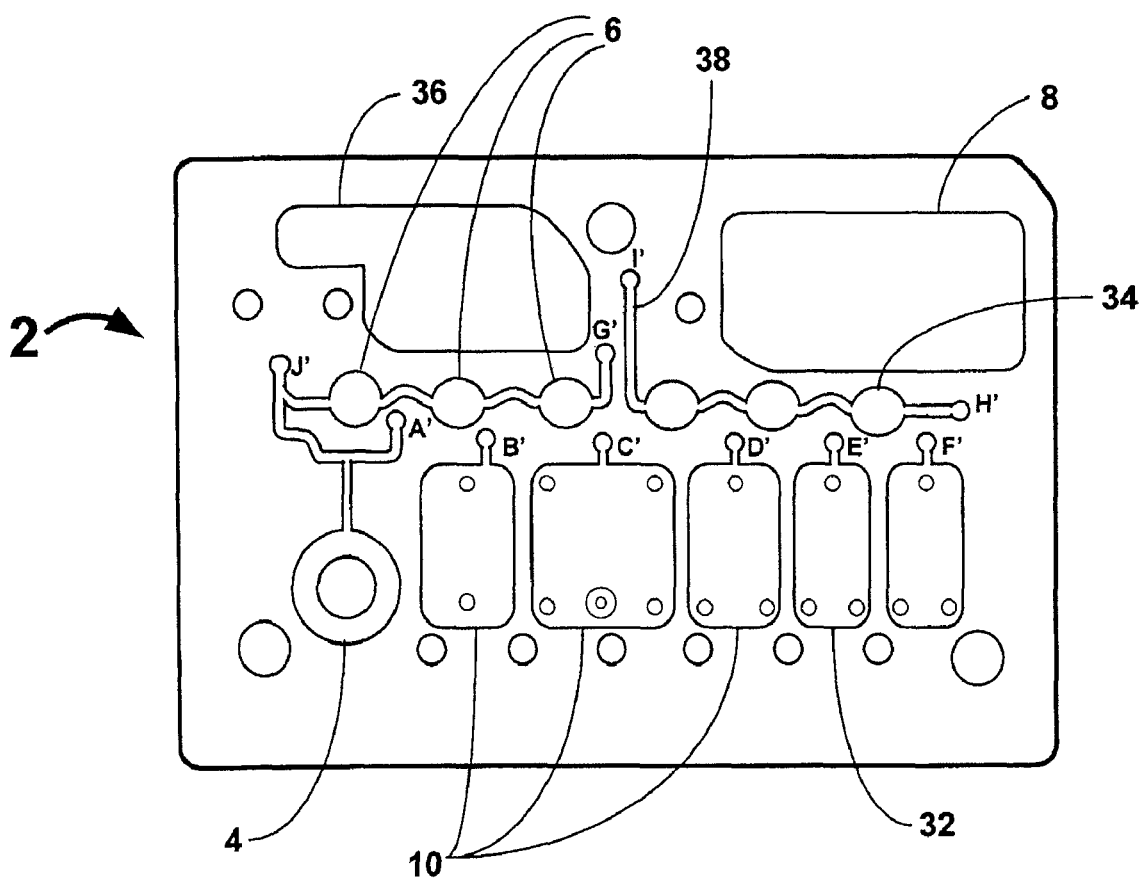

FIG. 2 illustrates exemplary layers of a fluidic device according to the present invention prior to assembly of the fluidic device which is disclosed in more detail below. FIGS. 3 and 4 show a top and bottom view, respectively, of an exemplary fluidic device after the device has been assembled. The different layers are designed and assembled to form a three dimensional fluidic channel network. A sample collection unit 4 provides a sample of bodily fluid from a patient. As will be explained in further detail below a reader assembly comprises actuating elements (not shown) can actuate the fluidic device to start and direct the flow of a bodily fluid sample and assay reagents in the fluidic device. In some embodiments actuating elements first cause the flow of sample in the fluidic device 2 from sample collection unit 4 to reaction sites 6, move the sample upward in the fluidic device from point G' to point G, and then to waste chamber 8. The actuating elements then initiate the flow of reagents from reagent chambers 10 to point B', point C', and point D', then upward to points B, C, and D, respectively, then to point A, down to point A', and then to waste chamber 8 in the same manner as the sample.

A sample collection unit 4 in a fluidic device 2 may provide a bodily fluid sample from a patient by any of the methods described above. If necessary, the sample may first be processed by diluting the bodily fluid in a dilution chamber, and or may be filtered by separating the plasma from the red blood cells in a filtration chamber. In some embodiments the sample collection unit, diluting chamber, and filtration chamber may be the same component, and in some embodiments they may be different components, or any two may be the same component and the other may be a separate component. In some embodiments there may be more than one sample collection unit in the fluidic device.

In some embodiments the sample collection unit is configured to collect a sample of bodily fluid from the subject and to deliver a predetermined portion of the sample to be assayed by the assay assembly. In this manner, the device automatically meters the appropriate volume of the sample that is to be assayed. The sample collection unit can comprise a sample collection well, a metering channel, and a metering element. Generally, the sample collection well collects the bodily fluid from the patient. The metering channel is in fluidic communication with the sample collection well and is dimensioned to collect the predetermined portion of the sample to be assayed. The metering element is adapted to prevent a volume of sample larger than the predetermined portion of the sample from being assayed.

Figure 4A:
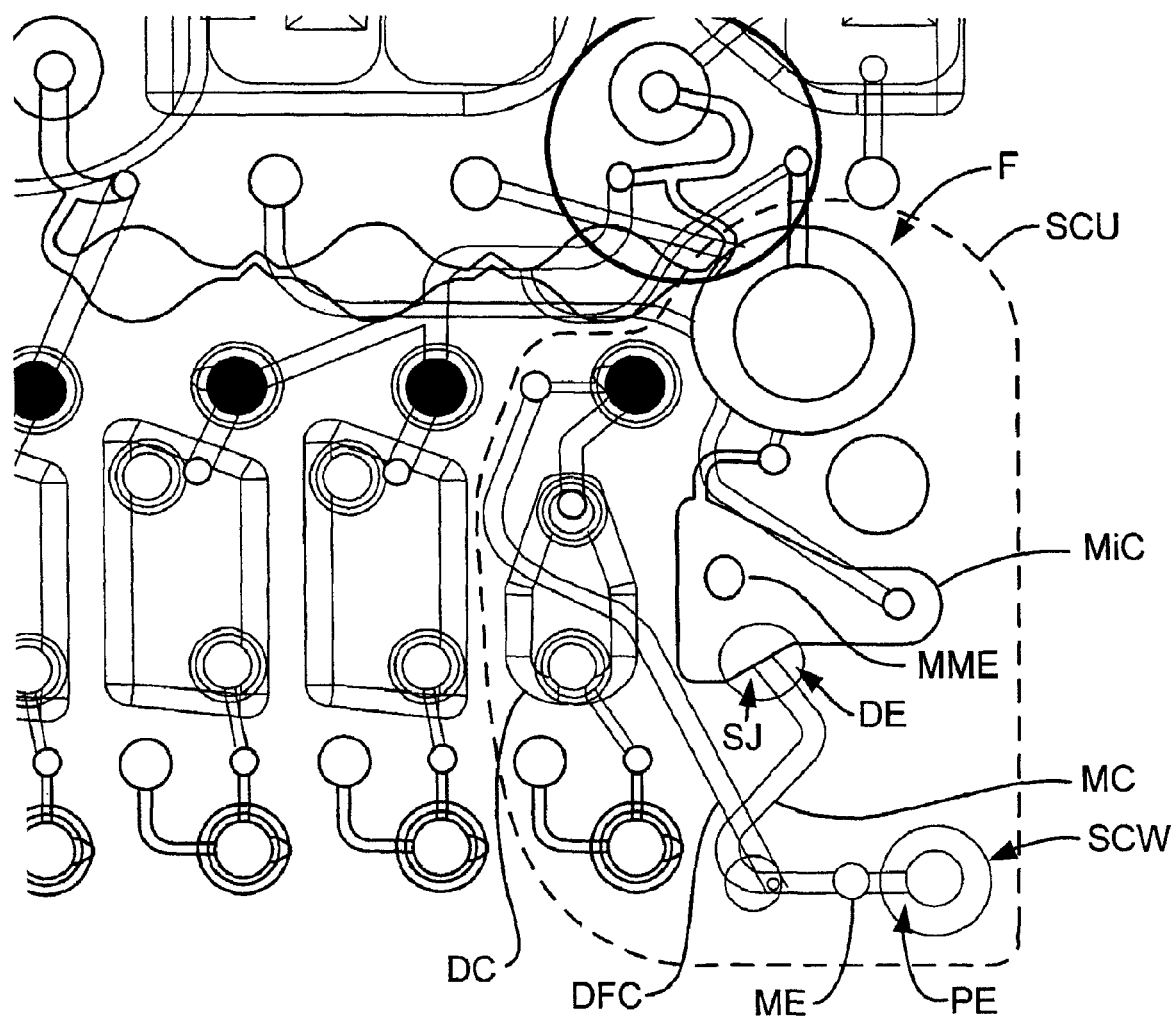
FIG. 4A illustrates an exemplary sample collection unit of the present invention.

FIG. 4A illustrates a top view of an exemplary sample collection unit (SCU) showing sample collection well SCW in fluidic communication with metering channel MC, and metering element (ME).

As shown, the sample collection well comprises a through hole with a larger diameter at the top tapering to a smaller diameter at the bottom. The through hole is intended to be the location where the sample is provided to the fluidic device, such as by fingerstick or pipetted blood. The sample collection well may be any inlet which allows for a sample to be received by the fluidic device.

The metering channel ME is in fluidic communication with the sample collection well SCW to receive the sample. The metering channel MC has a proximal end PE and a distal end DE. The distal end of the metering channel includes a stop junction SJ as will be described below.

In some embodiments the metering channel is about 10 mm long and has a cross section of about 1 mm$^2$. In other embodiments the metering channel is about 12.5 mm long and is about 0.9 mm wide and about 0.9 mm high.

A predetermined portion of sample as used herein generally refers to the volume of sample inside the metering channel between the stop junction and the metering element after it has closed the fluidic connection between the sample collection well and the metering channel. The dimensions of the metering channel will typically determine the volume of the predetermined portion of sample.

The metering channel is preferably capable of holding, prior to actuation of the metering element, a volume of sample greater than the predetermined portion such that the stop junction will not allow sample to flow into the mixing chamber when stressed by a hydrostatic pressure of sample from the sample collection unit.

Figure 4B:
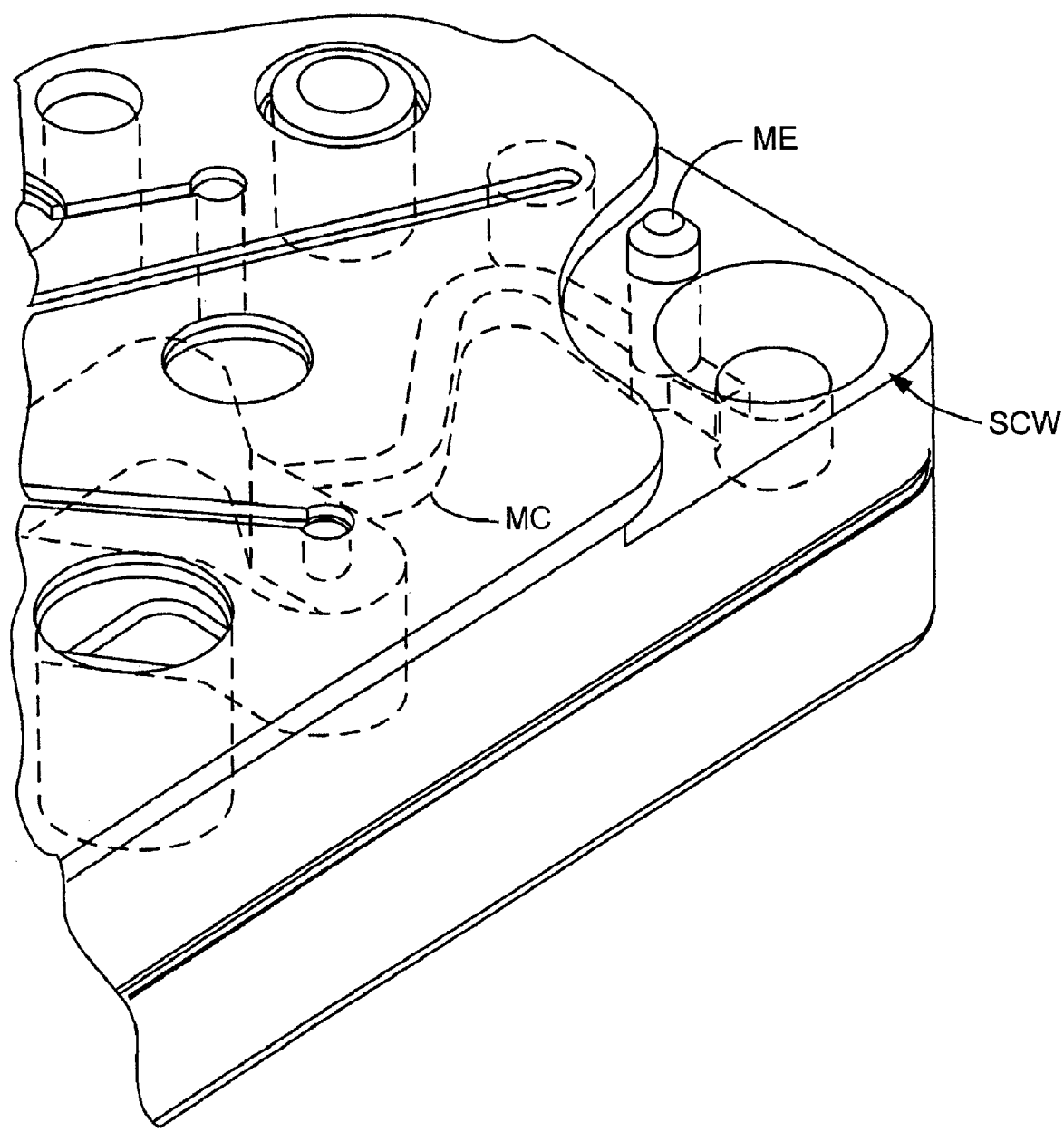
FIG. 4B illustrates an exemplary sample collection well in fluidic communication with a metering channel, and a metering element.

In some embodiments the metering element is adapted to prevent a volume of sample greater than the predetermined portion from being assayed. Generally, the metering element is adapted to pinch off the sample inside the metering channel from the sample collection well. The metering element can be a one-time valve initially open and adapted to be actuated by mechanical action by the reader assembly, as described herein. FIG. 4B is a perspective view of the metering element ME as a pin shown in an open, or unactuated, position that can be mechanically actuated by the reader assembly to close off the fluidic connection between the sample collection well and the metering channel. The metering element can take any shape and can be of any size, and can be moved into a position to prevent a volume of sample greater than the predetermined portion from being assayed by any technique, e.g., manual force or magnetic force.

In some embodiments the metering channel has at its distal end a stop junction. In FIG. 4A, stop junction SJ comprises metering channel MC opening into the larger mixing chamber MiC, thereby creating an abrupt end to the capillary dimensions of metering channel MC. The stop junction is shown comprising a right-angled junction between the MC and the mixing chamber MiC.

The stop junction is adapted to prevent sample from flowing into the mixing chamber before the predetermined portion of sample has been metered. While the stop junction as shown does not comprise any moveable elements, the stop junction may also comprises a valve or other blocking element that prevents the predetermined portion of sample from flowing from the metering channel into the mixing chamber.

An alternative method of loading the sample into the fluidic device is by side loading rather than loading the sample onto the top of the fluidic device. In such an embodiment, the metering channel terminates on the side or preferably, at a corner, of the cartridge. The metering channel is in direct communication with the mixing chamber and the diluent chamber is connected by a channel to the metering channel similar to the top loading embodiment above. The sample can be drawn into the metering channel by capillary action but does not enter the diluent flush channel as that channel is initially sealed from the metering channel. The user or an automated mechanism in the reader assembly is then seals the proximal end of the sample capillary prior to actuating the dilution operation as described above.

In some embodiments the inner surface of the sample collection well and/or the metering channel may be coated with a surfactant and/or an anti-coagulant solution. The surfactant provides a wettable surface to the hydrophobic layers of the fluidic device and facilitate filling of the metering channel with the liquid sample, e.g., blood, such that the contact angle of the metering channel is not so small that the stop junction cannot prevent flow of the blood at the distal end of the metering channel. The anti-coagulant solution helps prevent the sample, e.g., blood, from clotting when provided to the fluidic device. Exemplary surfactants that can be used include without limitation, Tween, Triton, Pluronic and other non-hemolytic detergents that provide the proper wetting characteristics of a surfactant. EDTA and heparin are non-limiting anti-coagulants that can be used.

In one embodiment the solution comprises 2% Tween, 25 mg/mL EDTA in 50% Methanol/50% H2O, which is then air dried. A methanol/water mixture provides a means of dissolving the EDTA and Tween, and also dries quickly from the surface of the plastic. The solution can be applied to the layers of the fluidic device by any means that will ensure an even film over the surfaces to be coated, such as, e.g., pipetting, spraying, printing, or wicking.

In some embodiments the sample collection unit also comprises a dilution chamber DC in fluidic communication with the metering channel, wherein the dilution chamber is configured to store a diluent and comprises a port for engaging pressure means for transferring the diluent from the dilution chamber into the metering channel. FIG. 4A shows dilution chamber DC and diluent flush channel DFC fluidly connecting dilution chamber DC with the metering channel MC. The diluent flush channel is adapted to be filled with diluent from the dilution chamber to provide a conduit from the diluent chamber to the sample capillary.

In some embodiments the sample collection unit further comprises a mixing chamber in fluidic communication with the metering channel, wherein the mixing chamber is configured to mix the predetermined portion of the sample with the diluent to yield a diluted sample. An exemplary mixing chamber MiC is shown in FIG. 4A. The mixing chamber is preferably dimensioned such that the intersection between the metering channel and the mixing chamber creates a stop junction to prevent the predetermined portion of sample from entering the mixing chamber until the diluent flushes the sample into the mixing chamber.

In some embodiments the mixing chamber includes a movable mixing element that causes the mixing of the predetermined portion of the sample with the diluent. Exemplary moveable mixing element MME is shown in FIG. 4A with a general ball shape. The movable mixing elements may have any shape, such as, e.g., a cube shape.

In one embodiment the movable mixing element is magnetically controlled, e.g., a magnetically controlled ball in the mixing chamber that, when magnetically controlled, will cause the mixing of the predetermined portion of the sample and the diluent. The ball can be about 5% of the combined volume of the sample and diluent. The ball can be magnetically controlled to move in a reciprocal, linear fashion, within the mixing chamber. The ball may be pre-magnetized or unmagnetized, but susceptible to magnetic forces.

The moveable mixing element is shown inside the mixing chamber, however, it is contemplated that the mixing element might operate outside of the fluidic device, such as if the reader assembly were adapted to agitate the fluidic device and thereby mix the predetermined portion of sample and the diluent.

In some embodiments the sample collection unit further comprises a filter configured to filter the diluted sample before it is assayed. Exemplary filter F is shown in FIG. 4A. In some embodiments the filter is fluidly connected to and downstream to the mixing chamber as shown in FIG. 4A.

While the sample collection unit can include a dilution chamber, mixing chamber, and a filter, it is contemplated that some or all of these components may not be included in the sample collection unit. It may, for example, be unnecessary to filter a sample and thus the sample collection unit may not have a filter.

In some embodiments it may be desirable to detect the presence of analytes on a cell surface, within a cell membrane, or inside a cell. The difficulty of detecting such analytes is that cells and other formed elements are particulate and components of cells do not readily interact with traditional assay chemistries which are designed to operate on analytes in solution. Cell-surface analytes react slowly and inefficiently with surface bound probes, and analytes inside the cell can not react at all with bound probes. To allow the detection of such analytes, in some embodiments the fluidic device may include a lysing assembly to lyse cells present in the bodily fluid sample. The lysing assembly may be incorporated with the sample collection unit, a dilution chamber, and/or a filtration chamber. In some embodiments the sample collection unit, dilution chamber, and lysing component are within the same element in the fluidic device. In some embodiments the lysing component may be incorporated with an assay reagent described below.

Where desired, lysing agents may be impregnated and then dried into porous mats, glass fiber mats, sintered frits or particles such as Porex, paper, or other similar material. Lysing agents may be dried onto flat surfaces. Lysing agents may also be dissolved in liquid diluents or other liquid reagents. In some embodiments porous materials are used to store the lysing agents because they can store a lysing agent in dry form likely to be very stable. They also facilitate the mixing of the bodily fluid sample with the lysing agent by providing a tortuous path for the sample as it moves through the porous material. In some embodiments such porous materials have a disc shape with a diameter greater than its thickness. In some embodiments lysing agents may be dried onto porous materials using lyophilization, passive evaporation, exposure to warm dry flowing gas, or other known methods.

A variety of lysing agents are available in the art and are suitable for use in connection with the subject fluidic device. Preferred lysing agents are non-denaturing, such as non-denaturing detergents. Non-limiting examples of non-denaturing detergents include thesit, sodium deoxylate, triton X-100, and tween-20. The agents are preferably non-volatile in embodiments where the agents are impregnated into a solid porous materials. In some embodiments lysing agents are mixed together. Other materials may be mixed with the lysing agents to modify the lytic effects. Such exemplary materials may be, without limitation, buffers, salts, and proteins. In some embodiments lysing agents will be used in amounts that are in excess of the minimum amount required to lyse cells. In some embodiments lysing agents will be used that can lyse both white and red cells.

One of the advantages of the present invention is that any reagents necessary to perform an assay on a fluidic device according to the present invention are preferably on-board, or housed within the fluidic device before, during, and after the assay. In this way the only inlet or outlet from the fluidic device is preferably the bodily fluid sample initially provided by the fluidic device. This design also helps create an easily disposable fluidic device where all fluids or liquids remain in the device. The on-board design also prevents leakage from the fluidic device into the reader assembly which should remain free from contamination from the fluidic device.

In a preferred embodiment there is at least one reagent chamber. In some embodiments there may be two, three, four, five, six, or more, or any number of reagent chambers as are necessary to fulfill the purposes of the invention. A reagent chamber is preferably in fluid communication with at least one reaction site, and when the fluidic device is actuated as described herein, reagents contained in said reagent chambers are released into the fluidic channels within the fluidic device.

Reagents according to the present invention include without limitation wash buffers, enzyme substrates, dilution buffers, conjugates, enzyme-labeled conjugates, DNA amplifiers, sample diluents, wash solutions, sample pre-treatment reagents including additives such as detergents, polymers, chelating agents, albumin-binding reagents, enzyme inhibitors, enzymes, anticoagulants, red-cell agglutinating agents, antibodies, or other materials necessary to run an assay on a fluidic device. An enzyme conjugate can be either a polyclonal antibody or monoclonal antibody labeled with an enzyme that can yield a detectable signal upon reaction with an appropriate substrate. Non-limiting examples of such enzymes are alkaline phosphatase and horseradish peroxidase. In some embodiments the reagents comprise immunoassay reagents. In general, reagents especially those that are relatively unstable when mixed with liquid are confined in a defined region (e.g. a reagent chamber) within the subject fluidic device. The containment of reagents can be effected by valves that are normally closed and designed for one-time opening, preferably in a unidirectional manner.

In some embodiments a reagent chamber contains approximately about 50 μl to about 1 ml of fluid. In some embodiments the chamber may contain about 100 μl of fluid. The volume of liquid in a reagent chamber may vary depending on the type of assay being run or the sample of bodily fluid provided. In some embodiments the reagents are initially stored dry and liquified upon initiation of the assay being run on the fluidic device.

Figure 5:
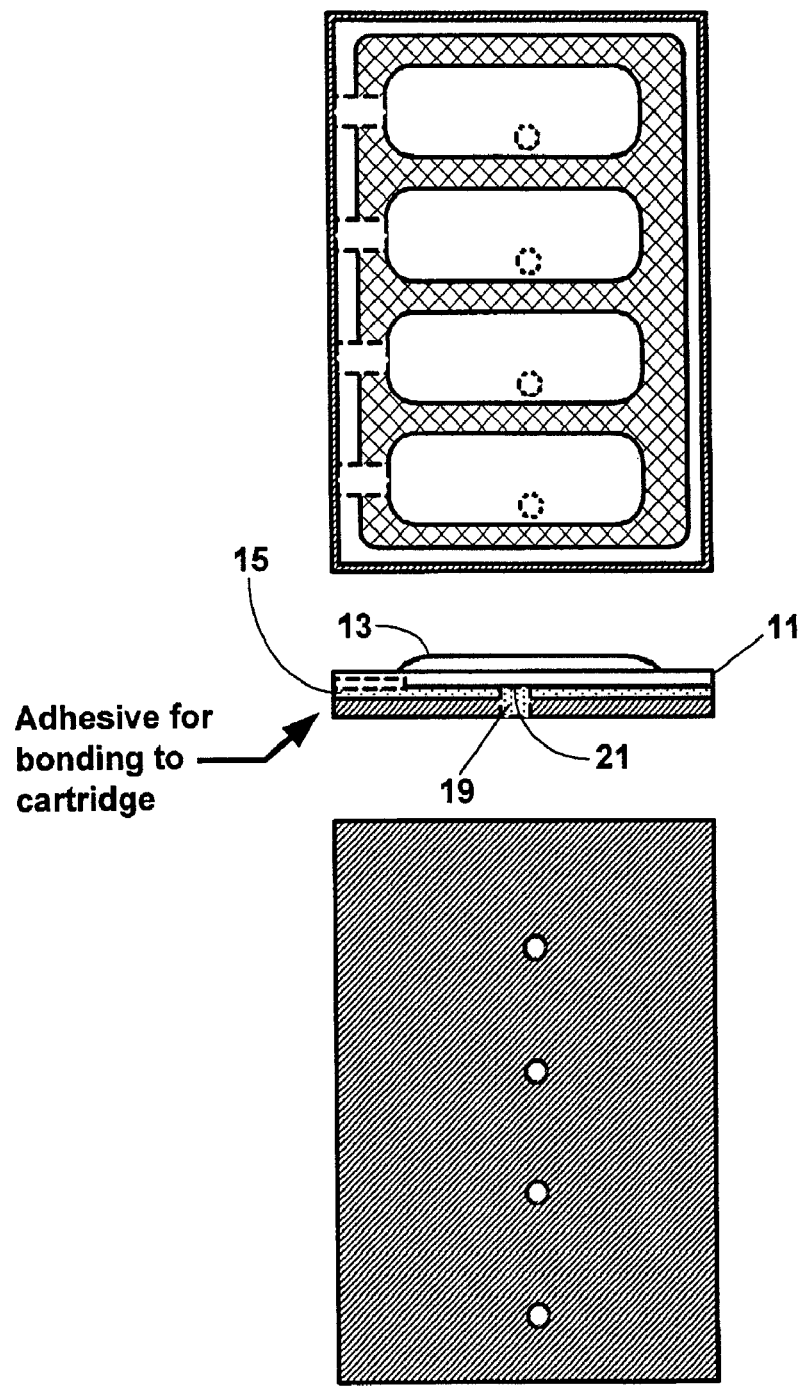
FIG. 5 shows a top, side, and bottom view of exemplary reagent chambers of the present invention.
Figure 6:
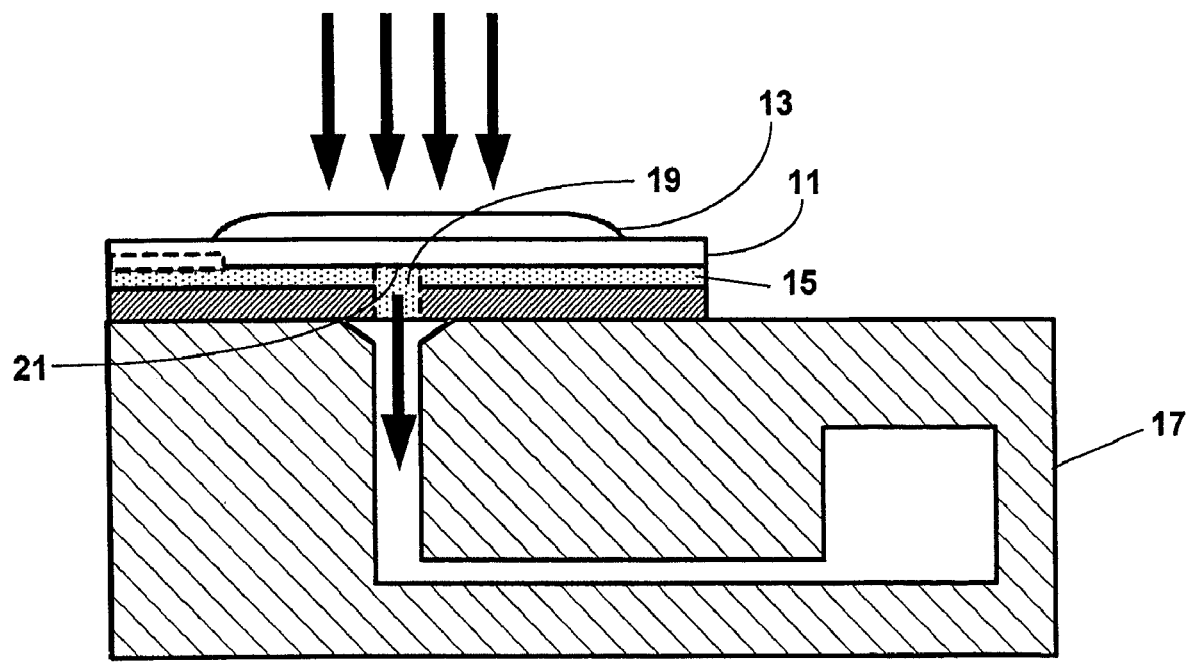
FIG. 6 illustrates an exemplary side view of a reagent chamber in fluidic communication with a fluidic device.

FIGS. 5 and 6 illustrate an exemplary embodiment of a sealed reagent chamber. FIG. 5 shows a top, side, and bottom view of a reagent chamber. A top layer 11 contains a plurality of bubbles or pouches 13. A bottom layer 15 has a bottom surface that is bonded to the fluidic device base 17 as shown in FIG. 6. The bottom layer 15 has a plurality of fluidic channels 19 dispersed through the entire surface, where each channel traverses the bottom layer 15. The fluid in the reagent chamber is contained within the chamber by pressure burstable seal 21 between the fluidic channel 19 and the chamber 13. The burstable seal 21 is designed such that at a predetermined pressure the seal bursts allowing the fluid in the chamber 13 to flow out into a fluidic channel 19.

Figure 7:
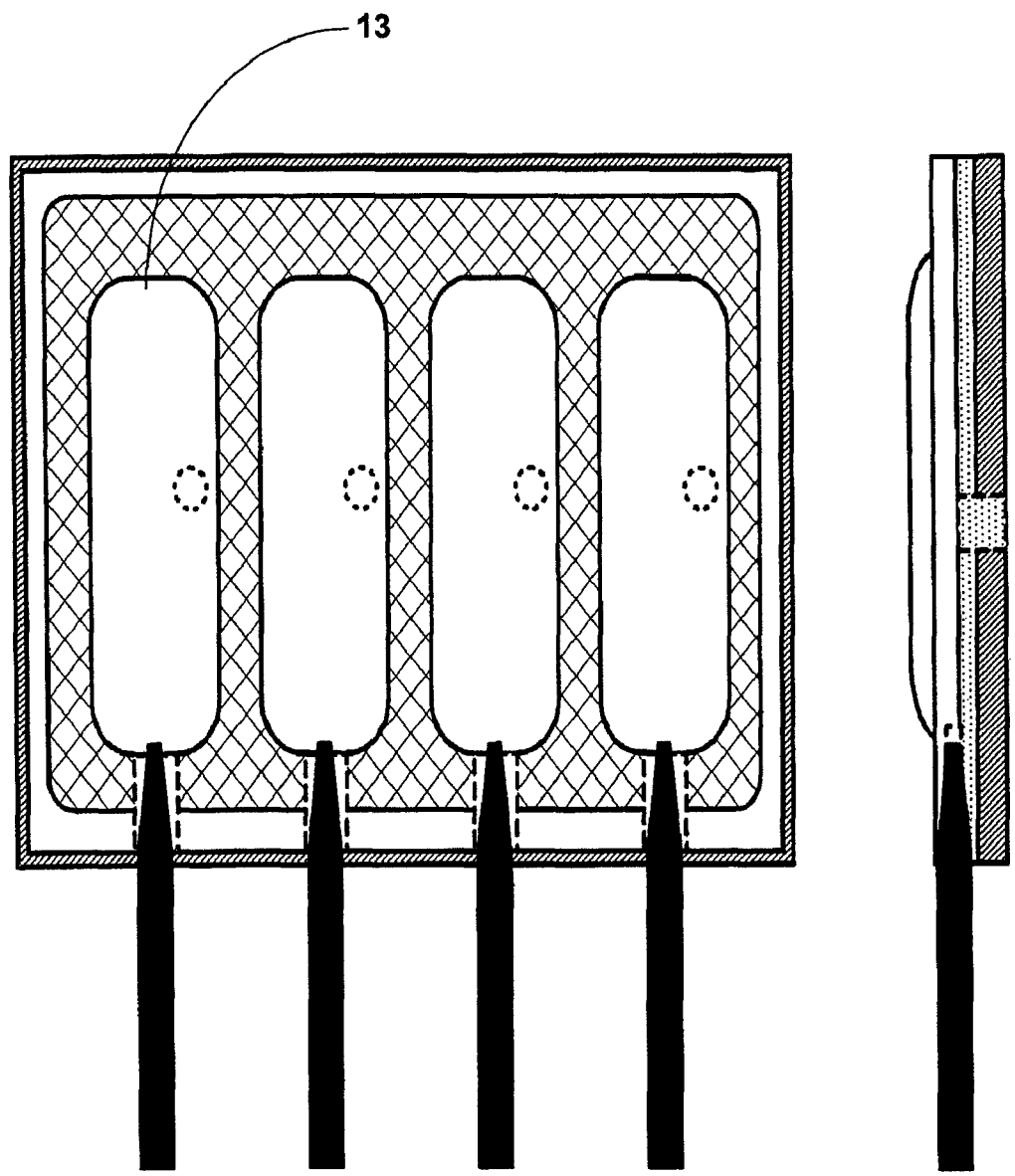
FIG. 7 illustrates exemplary reagent chambers being filled with reagents.

FIG. 7 shows an exemplary process of filling the reagent chambers 13 with, for example, reagents. Reagent chambers 13 may be filled with fluid using a fill channel and a vacuum draw channel. The process of filling the reagents involves first removing all the air from the chamber. This is done by drawing a vacuum through the vacuum draw channel. Once the vacuum is drawn, a permanent seal is placed between the fill channel and the vacuum draw channel. Next, required reagents are dispensed into the chamber through the fill channel. Then, a permanent seal is placed between the chamber and the fill channel. This ensures that when the chamber is compressed, the fluid can flow in only one direction, towards the burstable seal. If the compression imparts a pressure larger than the burst pressure of seal, the seal bursts and the fluid flows into the fluidic channel.

Figure 8:
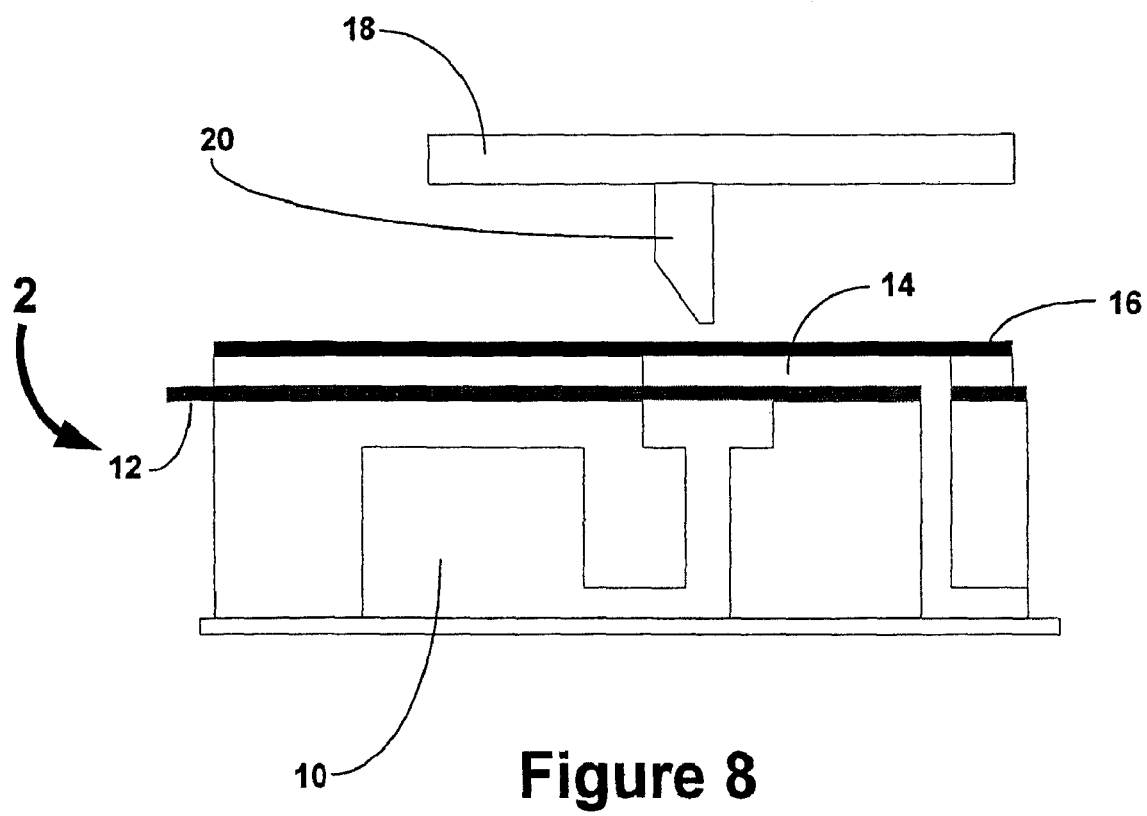
FIGS. 8 and 9 illustrate a side view of an exemplary fluidic device is combination with actuating elements of the reader assembly.
Figure 9:
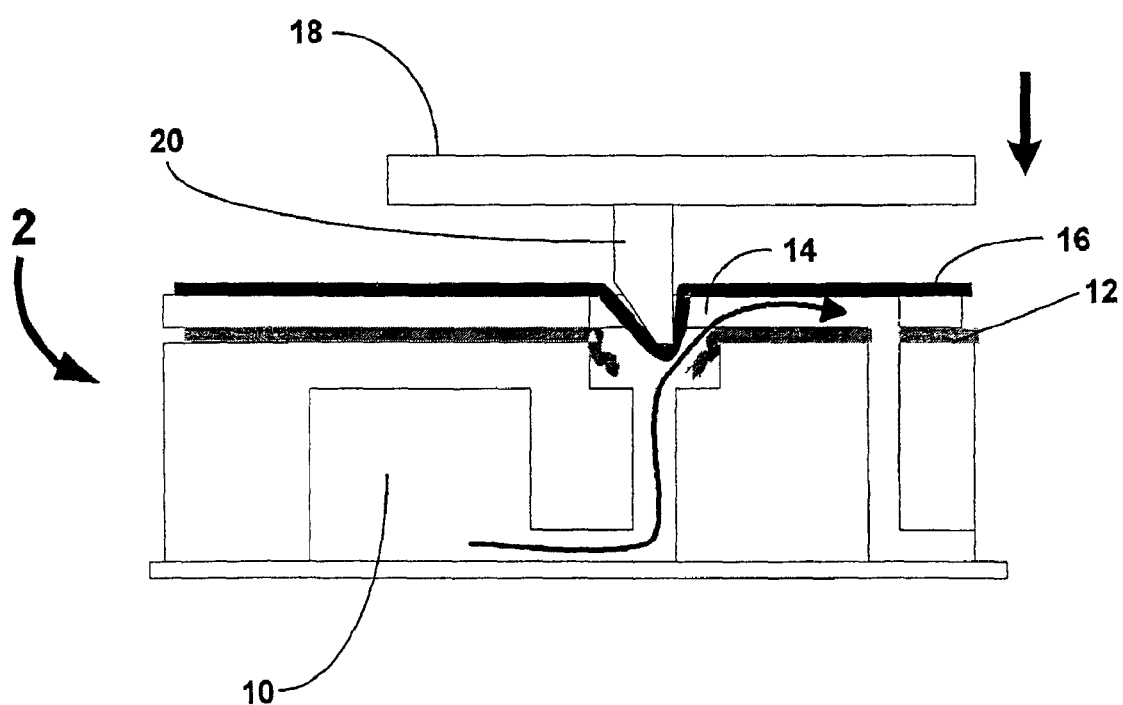

FIGS. 8 and 9 illustrate an embodiment of a fluidic device in operation with actuating elements as described herein. Fluidic device 2 contains a reagent chamber 10 and a layer of burstable foil 12 enclosing the reagent chamber. Above the burstable foil 12 is a portion of the microfluidic circuit 14. A tough, but elastomeric top cover 16 acts as the top layer of the fluidic device 2. The reader assembly includes a valve actuation plate 18. Securely attached to the plate 18 is a non-coring needle 20 such that when the plate is lowered, the sharp edge of the needle contacts the elastomeric cover 16. The top cover could also be made of flexible silicone material that would act as a moisture impermeable seal. This embodiment also provides a solution to liquid evaporation and leakage from a fluidic device by isolating any liquid reagents in the fluidic device from any dry reagents until the assay is initiated.

Figure 9A:
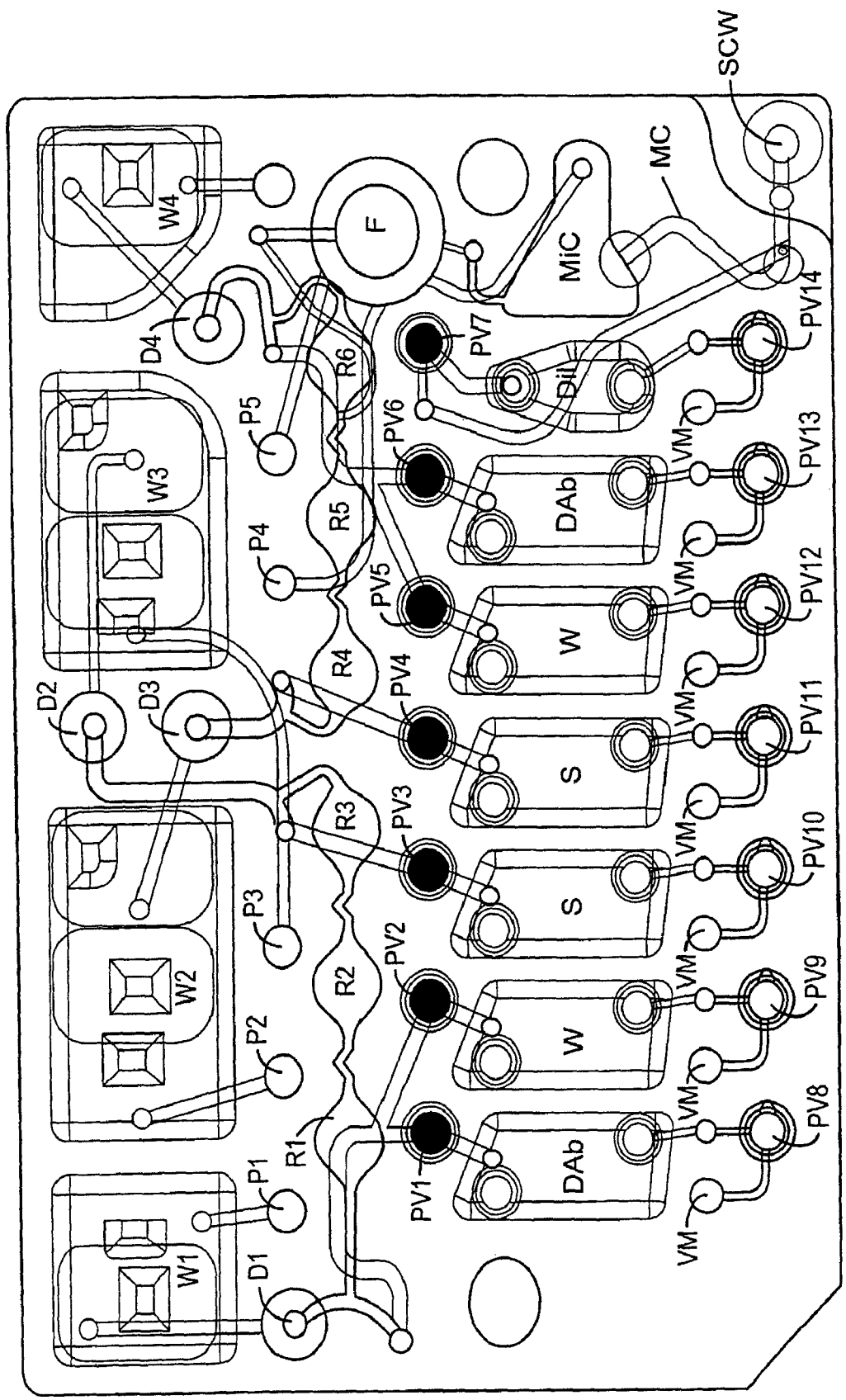
FIG. 9A illustrates an exemplary fluidic device including pump valves and vent modules

In another embodiment of the fluidic device shown in FIG. 9A, actuatable push valve assemblies PV1-PV14 are placed near the inlets and outlets of each reagent chamber and the dilution chamber to allow for long term isolation of the liquid contained therein. The actuatable valve assemblies are also configured to control the flow of reagent from the reagent chamber and dilution chamber into a fluidic channel connecting the chambers to the reaction sites.

In general the actuatable valve assembly comprises a sealing element and an actuator element. The sealing element is adapted to obstruct the flow of fluid when it is in a first position, and allows the flow of fluid when in a second position. The actuator element is adapted to move the sealing element from the first location to the second location.

Figure 9B:
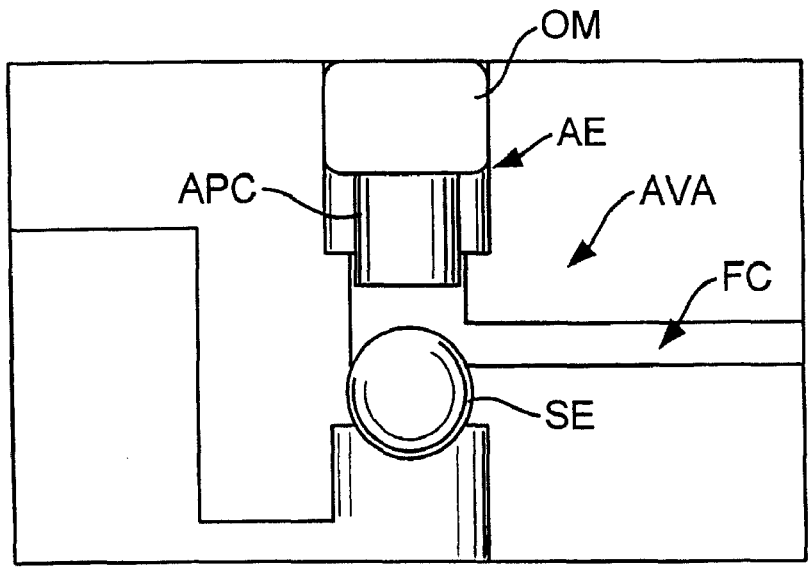
FIG. 9B-9I illustrates exemplary actuatable valve assemblies of the present invention.

In one embodiment of actuatable valve assembly AVA shown in FIG. 9B, the actuator element AE is a pin and the sealing element SE is a sealing ball. The pin comprises an actuatable pin core APC with an elastic over mold OM positioned over about half of the core. The sealing ball as shown has a generally spherical shape.

The core can be a stainless steel core, while the over mold can be made of silicone. The sealing ball can be of any material that can prevent fluid from flowing from reagent chamber RC to fluidic channel FC. In one embodiment the sealing ball is Nitrile (Buna-N).

Figure 9C:
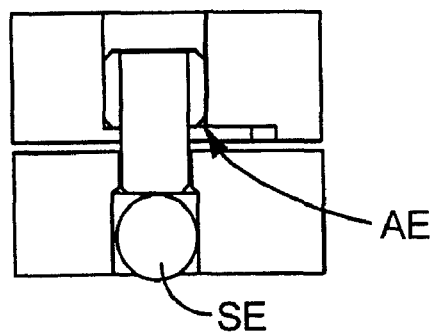

The actuator pin is adapted such that when the fluidic device in placed in a reader assembly, the actuator plate (not shown) actuates the actuator pin to displace the sealing ball into an open position shown in FIG. 9C. When the ball is in an open position, fluid from the reagent chamber can flow into the fluidic channel to the assay assembly.

As the actuator pin is actuated downward it forms an air tight seal ATS with the bottom of its guide hole to prevent fluid movement outside the designated flow path from the reagent chamber into the fluidic channel. The actuator pin is configured so that when it makes the air tight seal at the bottom of the guide hole the core of the actuator pin can still move down. This frees up a significant amount of build tolerance in the reader.

Figure 9D:
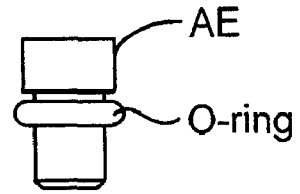
Figure 9E:
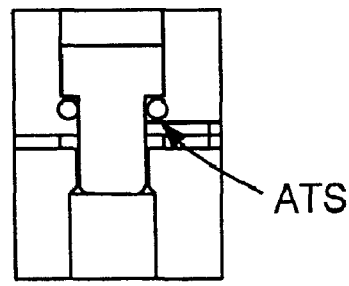

In one embodiment the actuator element comprises an actuator pin with two concentric diameters of different size and an O-ring positioned over the region with the smaller diameter as shown in FIG. 9D. The O-ring is adapted to slide over the smaller diameter of the actuator pin and the larger diameter is used as a guide to keep the pin straight in the fluidic device. When the valve assembly is actuated by the actuation plate of the reader, the O-ring contacts a fixed stop in the fluidic device. This contact forms an air tight seal between the fluidic device and the actuator pin.

Figure 9F:
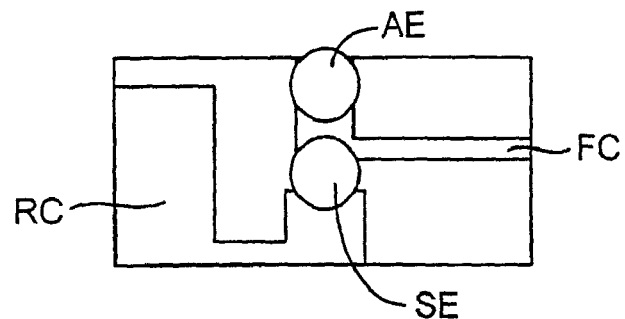
Figure 9G:
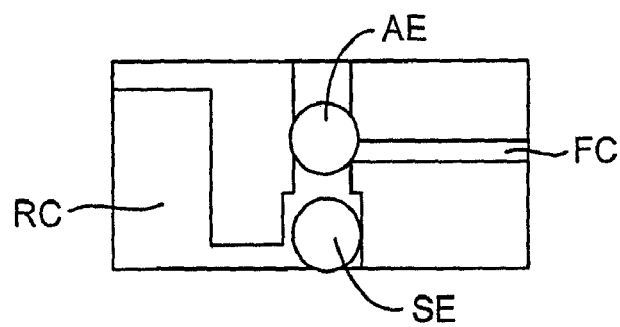

In one embodiment both the actuating element and the sealing element are two sealing balls as shown in FIG. 9F. The sealing element forms an air tight seal with the fluidic device, effectively sealing the reagent chamber from the fluidic network. A second ball is used to displace the first ball into an open position, opening the reagent chamber and forming an air tight seal as shown in FIG. 9G.

Figure 9H:
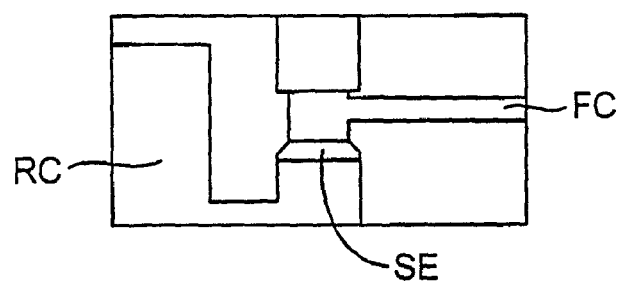
Figure 9I:
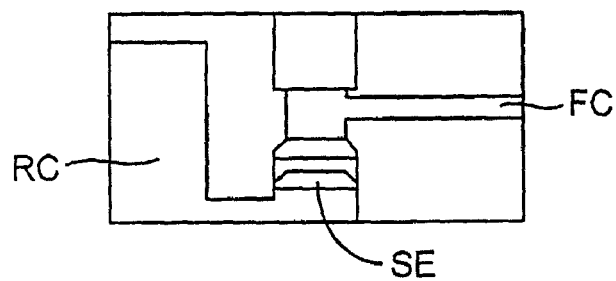

In one embodiment the sealing element SE comprises a stopper or plug which is adapted to block the fluid from the reagent chamber from entering the fluidic circuit. The stopper can be placed in the fluidic device during assembly, and is shown in its initial closed position in FIG. 9H. An actuating plate of the reader assembly can then actuate an actuator pin as described above to displace the stopper, thus allowing fluid to flow. FIG. 9I shows the stopped in an open position.

In preferred embodiments the reagent chamber and sample collection unit are fluidly connected to reaction sites where bound probes can detect an analyte of interest in the bodily fluid sample using the assay. A reaction site could then provide a signal indicative of the presence of the analyte of interest, which can then be detected by a detection device described in detail herein below.

In some embodiments the reactions sites are flat but they may take on a variety of alternative surface configurations. The reaction site preferably forms a rigid support on which a reactant can be immobilized. The reaction site surface is also chosen to provide appropriate light-absorbing characteristics. For instance, the reaction site may be functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, or combinations thereof. Other appropriate materials may be used in accordance with the present invention.

A reactant immobilized at a reaction site can be anything useful for detecting an analyte of interest in a sample of bodily fluid. For instance, such reactants include without limitation nucleic acid probes, antibodies, cell membrane receptors, monoclonal antibodies and antisera reactive with a specific analyte. Various commercially available reactants such as a host of polyclonal and monoclonal antibodies specifically developed for specific analytes can be used.

One skilled in the art will appreciate that there are many ways of immobilizing various reactants onto a support where reaction can take place. The immobilization may be covalent or noncovalent, via a linker moiety, or tethering them to an immobilized moiety. These methods are well known in the field of solid phase synthesis and micro-arrays (Beier et al., Nucleic Acids Res. 27:1970-1-977 (1999). Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art.

In some embodiments there are more than one reaction sites which can allow for detection of multiple analytes of interest from the same sample of bodily fluid. In some embodiments there are 2, 3, 4, 5, 6, or more reaction sites, or any other number of reaction sites as may be necessary to carry out the intent of the invention.

In embodiments with multiple reaction sites on a fluidic device, each reaction site may be immobilized with a reactant different from a reactant on a different reaction site. In a fluidic device with, for example, three reaction sites, there may be three different probes, each bound to a different reaction site to bind to three different analytes of interest in the sample. In some embodiments there may be different reactants bound to a single reaction site if, for example, a CCD with multiple detection areas were used as the detection device, such that multiple different analytes could be detected in a single reaction site. The capability to use multiple reaction sites in addition to multiple different probes on each reaction site enables the high-throughput characteristics of the present invention.

Figure 14A:
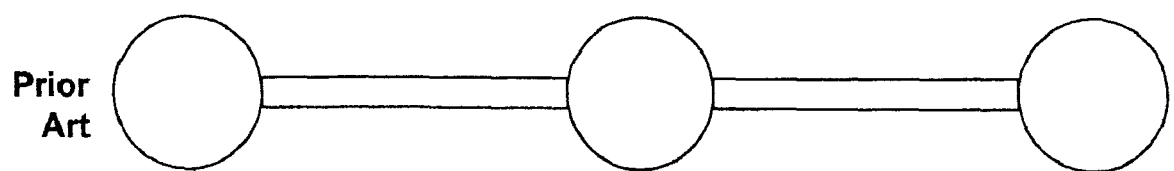
FIGS. 14A-C illustrate exemplary fluidic channels between reaction sites.
Figure 14B:
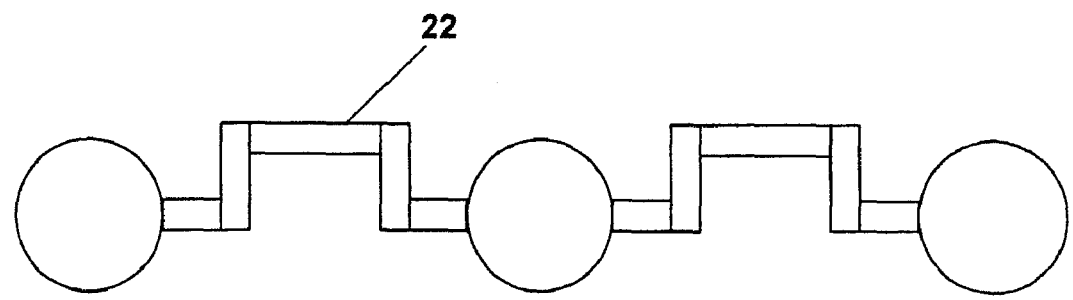
Figure 14C:
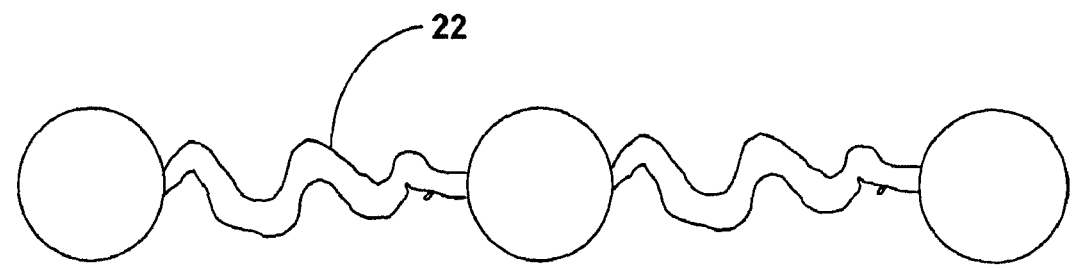

The present invention allows for the detection of multiple analytes on the same fluidic device. If assays with different luminescent intensities are run in adjacent reaction sites, photons (signals that emanate from the reactions) may travel from one reaction site to an adjacent reaction site, as reaction sites may be constructed of materials that allow photons to travel through the fluidic channels that connect the sites. This optical cross talk may compromise the accuracy of the detected photons. FIGS. 14B and 14C illustrate different embodiments of this invention that can eliminate or reduce the amount of optical cross-talk. Non-linear channels 22 will not allow photons (light) to pass through. Hence, embodiments such as those shown in FIGS. 14B and 14C would not allow signals from a reaction site to contaminate a signal produced from an adjacent site from which a detection device may be detecting. Additionally, the edges or walls of a reaction site may be constructed using optically opaque materials so that light will not escape the wells. In some embodiments the reaction sites are white or opaque.

Figure 15A:
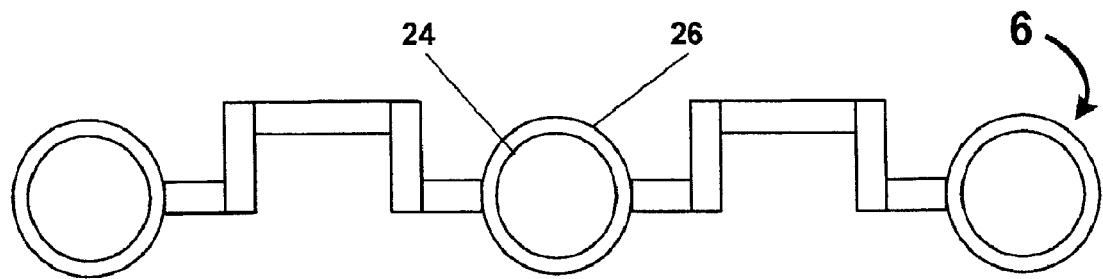
FIGS. 15A and 15B illustrate reactions sites to reduce the signal from unbound conjugates remaining in reaction sites.
Figure 15B:
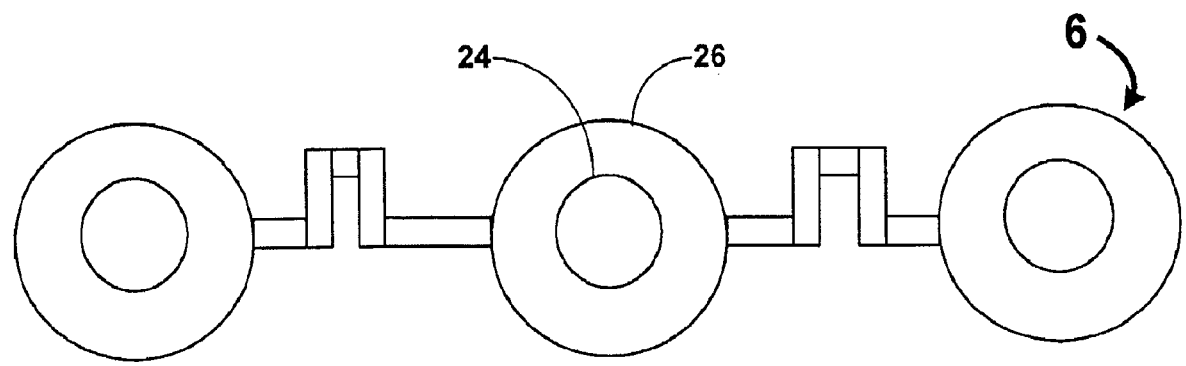

In some embodiments, unbound conjugates may need to be washed from a reaction site to prevent unbound conjugates from activating the substrate and producing and inaccurate signal. It may be difficult to remove conjugates sticking to the edges of the reaction sites in such a fluidic device if, for example, there is not an excess of a wash solution. To decrease the signal contributed from unbound conjugates stuck to the edge of a reaction site, it may be advantageous to expand the reaction site edge or wall radius in order to distance stuck conjugate from the desired actual detection area, represented by bound reactant. FIGS. 15A and 15B illustrates this concept. Reaction site 6 contains reaction surface 24 and edge or wall surface 26. In FIG. 15B, an edge surface 26 is shown at a greater distance from the center of the reaction site 6 than is the edge surface of the prior art design. This allows unbound conjugates to adhere to the edge surfaces and be distanced from bound conjugates, which are concentrated closer to the center of the reaction site 6.

In preferred embodiments of the invention the fluidic device includes at least one waste chamber to trap or capture all liquids after they have been used in the assay. In preferred embodiments, there is more than one waste chamber, at least one of which is to be used with a calibration assembly described herein below. On-board waste chambers also allow the device to be easily disposable. The waste chamber is preferably in fluidic communication with at least one reaction site.

At least one of these channels will typically have small cross sectional dimensions. In some embodiments the dimensions are from about 0.01 mm to about 5 mm, preferably from about 0.03 mm to about 3 mm, and more preferably from about 0.05 mm to about 2 mm. Fluidic channels in the fluidic device may be created by, for example without limitation, precision injection molding, laser etching, or any other technique known in the art to carry out the intent of the invention.

One of the common problems encountered in a microfluidic based assay system is the presence of air or gas bubbles. It is extremely difficult to remove a bubble once it is trapped within a fluidic channel. Bubbles present anywhere in the fluidic circuit, particularly in the reaction sites can compromise the assay capabilities. A bubble may end up occupying part of all of the surface area of a reaction site. Consequently the reader may end up reading a muted signal or no signal at all. FIG. 16 illustrates an embodiment where a bubble could be trapped in a filter 28 before it reaches a reaction site 6. A bubble trapper 28 can be positioned between a sample collection unit 4 and reaction site 6. The bubble trapper can have such a geometry that the bubbles tend to migrate towards the edges of this surface and remain stuck at that service, thereby not entering into the reaction sites.

In other embodiments the fluidic device is adapted to remove air trapped within the fluidic device. During an assay, a plurality of reagents may be passed over the reaction sites described herein. A segment of air, or an air slug, can separate the reagent to be flowed from the preceding reagent. To prevent the air slug from becoming trapped in the reaction site, each reagent is first "primed" into a separate waste chamber for the first few pump strokes before it is routed through the reaction sites. In FIG. 9A, W1 and W4 serve as the prime waste chamber for the control and sample side circuits respectively. An example of this "priming" is as follows. After the sample has passed through the reaction sites, the DAb as shown in FIG. 9A must bridge a large air gap before a continuous liquid column is once again established. The first few pump strokes are therefore actuated with pump P6 in the open position. Once the DAb has wet the entire line leading to the reaction site, pump P6 is promptly closed and pump P2 set to the open position. Flow of DAb thus proceeds through the read wells and into waste chamber W2.

Figure 16A:
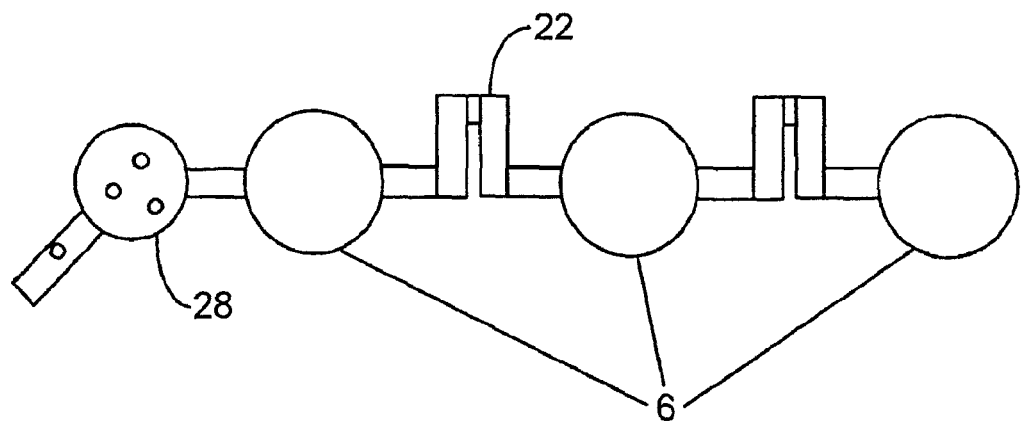
FIG. 16A shows an exemplary bubble trapper or remover to prevent bubbles from entering the reaction sites.
Figure 16B:
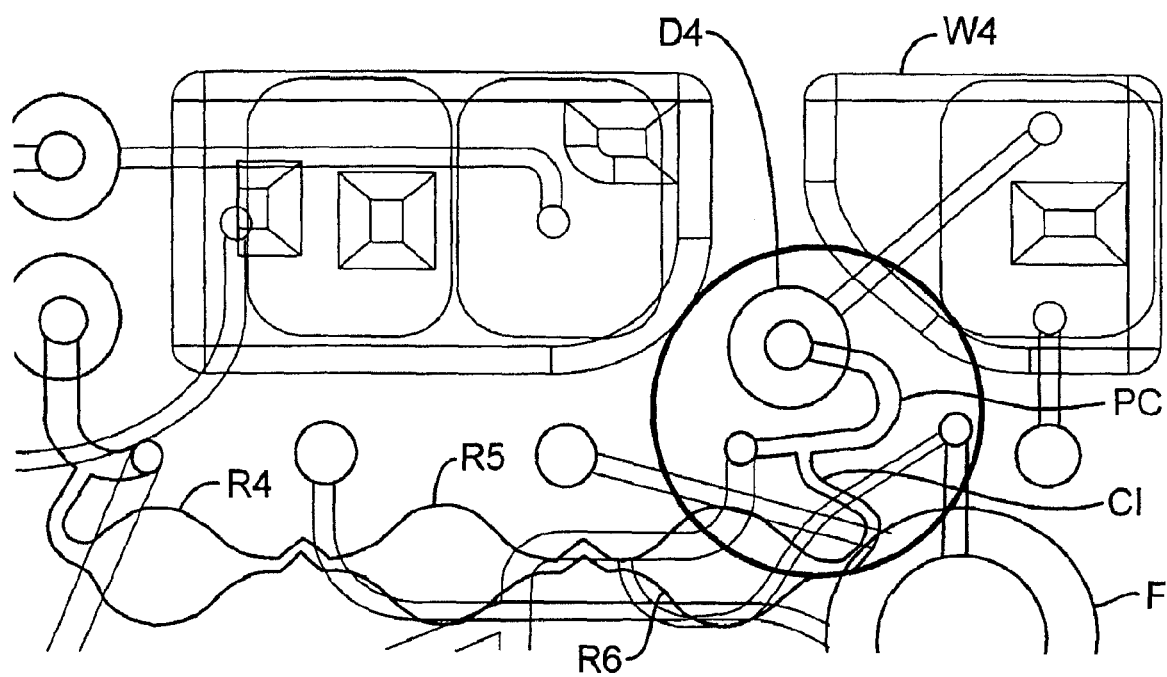
FIG. 16B illustrates exemplary fluidic communication between a duckbill valve and a waste chamber.

As shown in FIG. 16B, the size of the channels in the fluidic device can reduce the amount of air that enters the reaction sites. As the reagent passes through the priming circuit encircled in FIG. 16B, the width of the priming channel PC is about double the width of the channel C1 leading to the reaction sites. The potential for air to enter into the channel leading to the reaction sites is reduced or eliminated as the air would be forced to squeeze in the smaller channel.

In addition, the channel branching from the priming channel is perpendicular to the priming channel. Air flowing through the priming channel would thus be forced to flow 90 degrees into the channel leading to the reaction sites. The orifice to the branch is also reduced compared to the priming channel, thus enhancing the increased pressure that would need to occur for air to flow therethrough.

In some embodiments the fluidic device comprises valves that prevent backflow through the circuitry. During assays it is highly preferably that the volume, velocity, and timing of the liquid movement be as controlled as possible. In particular, assays may incorporate prolonged incubations where very little, if any, liquid movement should occur. During these stages it is particularly important that no or substantially no back-flow of liquid occur in the fluidic device. A likelihood of significant pressure differences exists, however, after the pump has stopped operating. To eliminate this backflow, a set of duck-billed valves are placed at appropriate locations in the fluidic circuit. The potential for backflow can be most serious when reagents that have mixed in the waste chamber, such as the DAb and the S reagents described herein flow back in the direction of the reaction sites. Four duckbilled check valves D1-D4 as shown in FIG. 9A are placed one at each inlet of each waste chamber. The duckbilled valves open under pressure in the forward direction and shut under pressure in the reverse direction. No liquid from the waste chamber is therefore able to traverse the duckbill and leak back into the reactions sites.

Figure 16C:
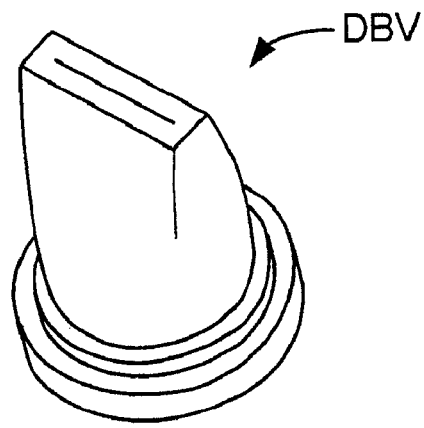
FIGS. 16C-16E show an exemplary duckbill valve
Figure 16D:
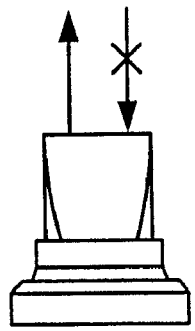
Figure 16E:
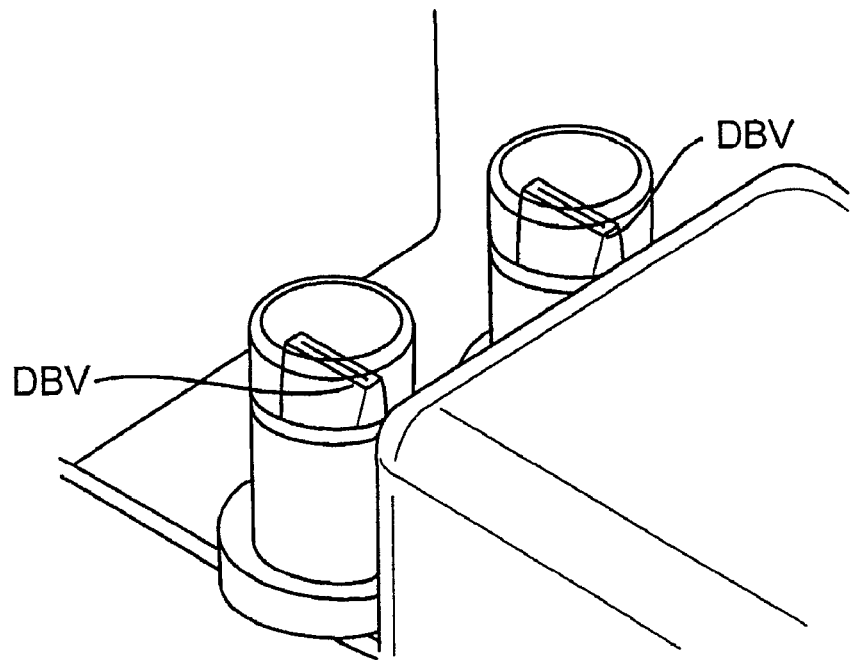

FIG. 16C shows an exemplary duckbilled valves DBV of the present invention. FIG. 16D illustrates the direction of allowed flow and the direction of prevented flow in the duck billed valves of the present invention. FIG. 16E shows two duckbilled valves inside the fluidic device.

Figure 16F:
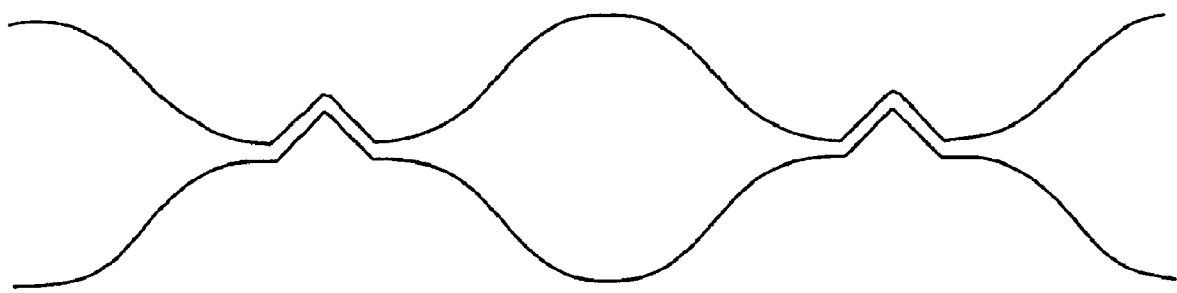
FIG. 16F illustrates reaction sites that are adapted for smooth flow of the reagents and for minimal boundary layer effects.

In preferred embodiments the wash reagent is able to remove the DAb reagent from the reaction sites by about 99.9% by washing. In general, a high washing efficiency resulting in a high degree of reduction of undesired background signals is preferred. Washing efficiency is typically defined by the ratio of signal from a given assay to the total amount of signal generated by an assay with no wash step and can be readily determined by routine experimentation. It is generally preferred to increase the volume of washing solution and time of incubation but without sacrificing the signals from a given assay. In some embodiments, washing is performed with about 200 ul to about 5000 ul of washing buffer, preferably between about 250 ul to about 1000 ul washing buffer, for about 30 to about 300 seconds. To facilitate this efficiency, the sides of the reaction sites as shown in FIG. 16F are adapted for smooth flow of the reagents and for minimal boundary layer effects. Where desired, the channels connecting the reaction sites can be configured as a chicane so as to reduce cross-talk of any kind and also uncontrolled fluid flow.

Additionally, it can be advantageous to use several cycles of small volumes of wash solution which are separated by periods of time where no wash solution is used. This sequence allows for diffusive washing, where labeled antibodies diffuse over time into the bulk wash solution from protected parts of the assay wells such as the well edges or surfaces where it is loosely bound and can then be removed when the wash solution is moved from the reaction well.

To ensure that a given photon count produced at a reaction site correlates with an accurate concentration of an analyte of interest in a sample, it is preferably advantageous to calibrate the fluidic device before detecting the photons. Calibrating a fluidic device at the point of manufacturing for example may be insufficient to ensure an accurate analyte concentration is determined because a fluidic device may be shipped prior to use and may undergo changes in temperature, for example, so that a calibration performed at manufacturing does not take into effect any subsequent changes to the structure of the fluidic device or reagents contained therein. In a preferred embodiment of the present invention, a fluidic device has a calibration assembly that mimics the assay assembly in components and design except that a sample is not introduced into the calibration assembly. Referring to FIGS. 3 and 4, a calibration assembly occupies about half of the fluidic device 2 and includes reagent chambers 32, reactions sites 34, a waste chamber 36, and fluidic channels 38. Similar to the assay assembly, the number of reagent chambers and reaction sites may vary depending on the assay being run on the fluidic device and the number of analytes being detected.

FIG. 9A shows a top view of an alternative embodiment of fluidic device with control assembly. The left side of the fluidic device as shown has no connection to any of the blood treatment elements on the right side, such as the sample collection unit, and it serves as the control assembly. The control assembly connects the reaction sites R1, R2, and R3 to waste chambers W1 and W3 and the set of three reagent chambers on the left side of the cartridge. A predetermined level of the analyte is dried in each of reaction sites R1, R2, and R3. The reagents Dab, W, and S then flow over the reaction sites in succession to produce the control signal for the cartridge.

Where desired, a sensor for assessing the reliability of an assay for an analyte in a bodily fluid with the use of the subject fluidic device can be provided together with the fluidic device, the reader and/or within the packaging of the subject system. The sensor is capable of detecting a change in operation parameters under which the subject system normally operates. The operation parameters include but are not limited to temperature, humidity, and pressure, which may affect the performance of the present system.

A fluidic device and reader assembly may, after manufacturing, be shipped to the end user, together or individually. As a reader assembly is repeatedly used with multiple fluidic devices, it may be necessary to have sensors on both the fluidic device and reader assembly to detect such changes during shipping, for example. During shipping, pressure or temperature changes can impact the performance of a number of components of the present system, and as such a sensor located on either the fluidic device or reader assembly can relay these changes to, for example, the external device so that adjustments can be made during calibration or during data processing on the external device. For example, if the pressure of a fluidic device dropped to a certain level during shipping, a sensor located on the fluidic device could detect this change and convey this information to the reader assembly when it is inserted into the reader assembly by the user. There may be an additional detection device in the reader assembly to perform this, or such a device may be incorporated into another system component. In some embodiments this information may be wirelessly transmitted to either the reader assembly or the external device. Likewise, a sensor in the reader assembly can detect similar changes. In some embodiments, it may be desirable to have a sensor in the shipping packaging as well, either instead of in the system components or in addition thereto.

Manufacturing of the fluidic channels may generally be carried out by any number of microfabrication techniques that are well known in the art. For example, lithographic techniques are optionally employed in fabricating, for example, glass, quartz or silicon substrates, using methods well known in the semiconductor manufacturing industries such as photolithographic etching, plasma etching or wet chemical etching. Alternatively, micromachining methods such as laser drilling, micromilling and the like are optionally employed. Similarly, for polymeric substrates, well known manufacturing techniques may also be used. These techniques include injection molding or stamp molding methods where large numbers of substrates are optionally produced using, for example, rolling stamps to produce large sheets of microscale substrates or polymer microcasting techniques where the substrate is polymerized within a micromachined mold.

In some embodiments at least one of the different layers of the fluidic device may be constructed of polymeric substrates. Non limiting examples of polymeric materials include polystyrene, polycarbonate, polypropylene, polydimethysiloxanes (PDMS), polyurethane, polyvinylchloride (PVC), and polysulfone.

The fluidic device may be manufactured by stamping, thermal bonding, adhesives or, in the case of certain substrates, for example, glass, or semi-rigid and non-rigid polymeric substrates, a natural adhesion between the two components. In some embodiments the fluidic device is manufactured by ultrasonic or acoustic welding.

FIG. 2 shows one embodiment of the invention in which fluidic device 2 is comprised of 7 layers. Features as shown are, for example, cut in the polymeric substrate such that when the layers are properly positioned when assembly will form a fluidic network. In some embodiments more or fewer layers may be used to construct a fluidic device to carry out the purpose of the invention.

Figure 16G:
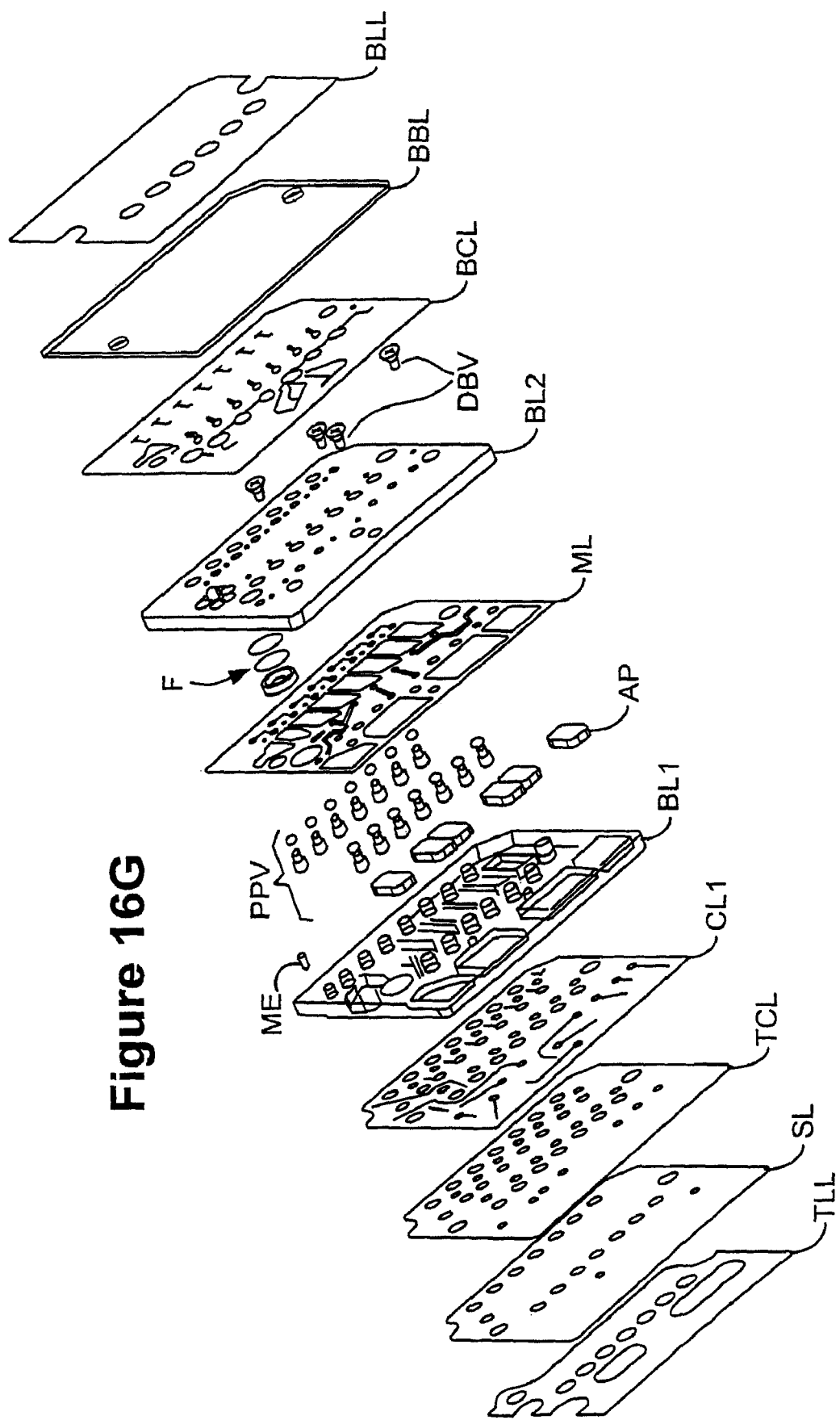
FIG. 16G shows a perspective view of various layers of an exemplary fluidic device of the present invention.

FIG. 16G illustrates the layers of an exemplary fluidic device. The fluidic device as shown has ten (10) layers held together by adhesive attached to appropriate layers. The layers may also be ultrasonically welded together.

The top label TLL is the top layer of the cartridge and preferably contains basic printed instructions for the user, e.g. where to place the blood and how to insert the cartridge into the reader assembly, as well as any relevant lot, type, and regulatory information.

Silicone layer SL provides a compliant material on the top surface of the cartridge that enables a robust seal. During an assay, the silicone layer as shown is adapted to be pierced by the actuation plate in the reader assembly in thirteen separate locations to connect the fluidic circuits to the pump within the instrument as described herein.

The silicone layer can also ensures that once the cartridge is removed from the reader after completion of an assay, liquid remaining in the cartridge are unable to leak from the cartridge via the holes created by the needles in the actuation plate. The surface tension required to traverse the silicone layer is typically enough to keep the liquids contained with the fluidic device.

The top cover TCL as shown is a thin, clear layer of polycarbonate. This layer provides a fluid tight seal to the top fluidic circuit and provides through-holes accommodating the fourteen (14) push pin valves PPV, the metering element ME of the sample collection unit and the thirteen (13) needles in the actuation plate discussed above. This layer is relieved at one corner to provide access to the sample collection well.

The next layer comprises the top channel layer CL1, and can be made of clear polycarbonate or clear acrylic.

The top block BL1, and can be made of clear polystyrene. As shown, this block serves as part of the chambers which accommodate the liquid reagents, while the other part is in the bottom block BL2. It also forms part of the waste chambers.

Middle layer ML as shown can be made of clear polycarbonate or clear acrylic.

Bottom block layer BL2 is preferably opaque, white polystyrene. BL2 as shown provides part of the chambers which house the reagents and the waste chambers. It also forms the top surface of the reaction sites. The opaque, white feature of this layer serves to scatter light generated by the assay chemistry downwards towards the detector. In this way, the number of photons generated that reach the detector is approximately doubled.

Bottom channel layer BCL can be made of clear polycarbonate or clear acrylic. BCL contains the cutouts for the six (6) read wells as well as fluidic circuitry that connects them to the other layers in the cartridge as well as to each other.

Bottom layer BBL provides the surface of the reaction sites. It is preferably clear polystyrene through which light generated by the assay can reach the detection assembly. This layer further seals the bottom of the fluidic device.

The bottom label BLL can contain, e.g., a barcode that identifies the cartridge as well as holes corresponding to the read wells that act as windows for the emitted light to pass through and which is detected by the detection assembly.

In one aspect, the subject device is designed to prevent fluid inside a fluidic device from contacting the components of a reader assembly which may need to remain dry and or uncontaminated before the actual assay, and also to prevent contamination to a detection device within the reader assembly. A leak in the fluidic device could result in liquids, for example reagents or waste, escaping from the fluidic device and contaminating the reader. In other embodiments a liquid absorbing material, such as polymeric materials, can be placed within a portion of the fluidic channel or waste chamber to absorb the waste liquid. An absorbent material can be a solid material, porous material, gel, porous or sintered polymer, high salt fluid, thermoplastic polymer (such as those available from Sigma, Aldrich, Porex™, etc.), polyolefin resin, or porous plastic, including, e.g., Porex™ plastics. The absorbent material may also be an aerosol particulate spray, for example, comprising porous particulate matter. The absorbent material can also be a cellulosic material such as paper, e.g., Kimwipe™, paper towel or the like. In addition, the absorbent material can a be, for example, sodium polyacrylate, polyacrylamide, agarose, agar, polyethylene, polypropylene, a high molecular weight polyethylene, polyvinylidene fluoride, ethylene-vinyl acetate, polytetrafluoroethylene, stryene-acrylonitrile, polysulfone, polycarbonate, dextran, dry sephadex, polyphthalate, silica, glass fiber, or other material similar to those included herein. Additionally, an absorbent material can be any combination of the materials described herein. Many polymers can absorb fluids many of times their weight. Hence, only minute quantities of such polymeric materials may be required to accomplish the goal of absorbing leaked fluids. In general the absorbent material can be bibulous and the volume fraction of air is generally about 10-70% of the absorbent material. In some embodiments a waste chamber is filled with a superabsorbent material. In some embodiments leaked liquid may be converted into a gel or other solid or semi-solid form.

In some embodiments the absorbent material comprises at least one quenching agent which reacts with at least one reagent from said assay assembly to reduce interference of the optical signal indicative of the presence of the analyte in the sample. The quenching agent can inhibit the binding between reagents, or in preferred embodiments the quenching agent inactivates at least one and more preferably all reagents which may contribute to an interfering optical signal.

The reagent or reagents with which the quenching agent in the waste chamber reacts to reduce the interference can be, for example without limitation, an unbound enzyme and/or an unbound substrate. The reagent with which the quenching agent reacts to reduce the interference is generally not as important as the reduction of the interference itself. The quenching agent in the waste chamber can vary depending on the type of assay that is being performed in the fluidic device. Preferably a subject quenching agent reduces an interfering optical signal by at least about 95%, at least about 98%, at least about 99%, at least about 99.9%, or more. In a preferred embodiment the quenching agent reduces an interfering optical signal by about 99%. In another preferred embodiments the waste chamber reduces optical interference by at least about 99.5%. In more preferred embodiments the quenching agent reduces optical interference by at least about 99.9%. The quenching effect should preferably be rapid, typically within a few
minutes and more preferably within a few seconds. It also should preferably be as complete as possible to ensure the interference is reduced as much as possible. In preferred embodiments the inactivation of the enzyme reaction should be more than 99% complete before the optical signal indicative of the presence of the analyte in the sample is detected by any detection mechanism that may be used with the fluidic device as described herein.

In some embodiments the quenching agent can be a chemical that is a strong non-volatile acid such as trichloroacetic acid or its salt sodium trichloracetate. The substance can also be a strong alkali such as sodium hydroxide. Other strong non-volatile acids and strong alkalis can be used in accordance with the present invention. In some embodiments the quenching agent reduces the optical interference by inhibiting the enzyme. In an ELISA, e.g., the quenching agent can interfere with the enzyme's ability to convert the substrate to produce a luminescent signal. Exemplary enzyme inhibitors include lactose which inhibits the action of β-galactosidase on luminogenic galactosides, and phosphate salts which inhibit phosphatases. In other embodiments the quenching agent can reduce the interference by denaturing the enzyme. Once denatured the enzyme it is unable to carry out it enzymatic function and the optical interference is suppressed or reduced. Exemplary denaturants include detergents such as sodium dodecyl sulfate (SDS), heavy metal salts such as mercuric acetate, or chelating agents such as EDTA which can sequester metal ions essential for activity of certain enzymes such as alkaline phosphatase. All types of surfactants may be used including cationic (CTMAB) and anionic (SDS).

In addition, the quenching agent can be a non-denaturing chemical that is incompatible with enzyme activity. Exemplary chemicals include buffers and the like that change the pH to a value where the enzyme becomes inactive and thus unable to catalyze the production of the interfering signal.

Furthermore, the quenching agent can be, for example, an organic charge-transfer molecule, including 7,7,8,8-tetracyanoquinodimethane (TCNQ), 2,3,5,6-tetrafluoro-7,7,8,8-tetracyanoquinodimethane (TFTCNQ), carbon nanotubes, mordant yellow 10 (MY) and 4-amino-1,1$^1$-azobenzene-3,4$^1$-disulfonic acid (AB). In preferred embodiments the azobenzene compounds are MY and AB, as they are considerably more water-soluble than TCNQ, TFTCNQ and carbon nanotubes. The structure of AB is shown below in:

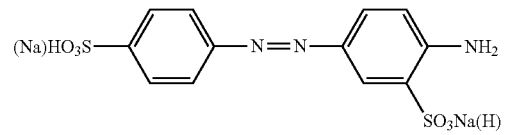

In some embodiments the quenching agent can be heavy atoms such as iodine which reduces the interference by quenching a fluorescent species used to enhance a chemiluminescent signal. In other embodiments the quenching agent can be an organic compound with an absorption spectrum overlapping the fluorescence emission spectrum of a fluorescent species used to enhance a chemiluminescent signal. In some embodiments such a quenching agent is a dark quencher such as a dispersion of carbon particles (e.g., carbon black, charcoal). Carbon can inactivate chemiluminescence by absorbing actives species, and it is also a very good quenching agent that is substantially incapable of emitting fluorescence.

In yet some embodiments the quenching agent can be an antioxidant, which can reduce the interference by disrupting the chemiluminescent reaction. Quenching agents that may be used in some embodiments of the invention include but are not limited to Trolox, butylated hydroxytoluene (BHT), ascorbic acid, citric acid, retinol, carotenoid terpenoids, non-carotenoid terpenoids, phenolic acids and their esters, and bioflavinoids.

In still other embodiments, the quenching agent can be a singlet oxygen quencher, which can reduce the interference by disrupting the chemiluminescent reaction. Some singlet oxygen quenchers include but are not limited to 1,4 diazabicyclo[2,2,2]octane, thiol containing compounds such as methionine or cysteine, and carotenoids such as lycopene. In general, the substance used to impregnate or saturate the absorbent material is preferably highly concentrated, typically in large molar excess of the assay reagents.

The present system also provides a fluidic device that can run a variety of assays, regardless of the analyte being detected from a bodily fluid sample. A protocol dependent on the identity of the fluidic device may be transferred from an external device where it can be stored to a reader assembly to enable the reader assembly to carry out the specific protocol on the fluidic device. In preferred embodiments, the fluidic device has an identifier (ID) that is detected or read by an identifier detector described herein. The identifier can then be communicated to a communication assembly, where it can then be transferred or transmitted to an external device.

In some embodiments the identifier may be a bar code identifier with a series of black and white lines, which can be read by an identifier detector such as a bar code reader, which are well known. Other identifiers could be a series of alpha-numerical values, colors, raised bumps, or any other identifier which can be located on a fluidic device and be detected or read by an identifier detector. In some embodiments the identifier may comprise a storage or memory device and can transmit information to an identification detector. In some embodiments both techniques may be used.

Once a bodily fluid sample is provided to a fluidic device, it is inserted in a reader assembly. In some embodiments the fluidic device is partially inserted manually, and then a mechanical switch in the reader assembly automatically properly positions the fluidic device inside the reader assembly. Any other mechanism known in the art for inserting a disk or cartridge into a device may be used as well. In some embodiments only manual insertion may be required.

In some embodiments the reader assembly comprises an identifier detector for detecting or reading an identifier on the fluidic device, a controller for automatically controlling the detection assembly and also mechanical components of the reader assembly, for example, pumps and/or valves for controlling or directing fluid through the fluidic device, a detection device for detecting a signal created by an assay run on the fluidic device, and a communication assembly for communicating with an external device.

An identifier detector detects an identifier on the fluidic device which is communicated to a communication assembly. In some embodiments the identifier detector can be a bar code scanner-like device, reading a bar code on a fluidic device. The identifier detector may also be an LED that emits light which can interact with an identifier which reflects light and is measured by the identifier detector to determine the identity of a fluidic device.

In preferred embodiments the reader assembly houses a controller which controls a pump and a series of valves to control and direct the flow of liquid within the fluidic device. In some embodiments the reader assembly may comprises multiple pumps. The sample and reagents are preferably pulled through the fluidic channels by a vacuum force created by sequentially opening and closing at least one valve while activating a pump within the reader assembly. Methods of using at least one valve and at least one pump to create a vacuum force are well known. While a negative pulling force may be used, a positive pushing force may also be generated by at least one pump and valve according to the present invention. In other embodiments movement of fluid on the fluidic device may be by electro-osmotic, capillary, piezo-electric, or microactuator action.

FIGS. 8 and 9 illustrate an exemplary sequence to initiate the flow of a reagent within the fluidic device. An actuation plate 18 in the reader assembly comprises a non-coring needle or pin 20 which when lowered flexes the top cover 16, as it is preferably made of strong, flexible elastomeric material. However, the easily rupturable foil 12 then ruptures due to the stress induced by the flexing of top cover 16. Valves located downstream to the reagent chamber puncture different areas of foil in the fluidic device and can then work in tandem with a pump within the reader assembly to create a vacuum force to pull the reagent out of the reagent chamber 6 into a fluidic channel and then direct the flow of the reagent to a reaction site. At least one valve is preferably fluidically connected to a pump housed within the reader assembly. The non-coring needle or pin 20 is removed from the fluidic device when the device is removed from the reader assembly. One of the advantages of this embodiment is that no on-chip pump is required, which, at least, decreases the size and cost of the fluidic device, and allows the device to be disposable.

In one embodiment the fluidic device comprises six pump ports P1-P6 shown in FIG. 9A which are adapted to be connected to a vacuum pump housed in the reader assembly. Each of the seven reagent tanks, (2 Dab chambers, 2 waste chamber, 2 substrate chambers and 1 dilution chamber), are connected via vent manifolds VM to the atmosphere. Fluid flows in the direction of negative pressure driven by ambient air pressure. The specific reagent to be moved and flow direction are selected by activating the pump and opening a specific pump port/vent combination that allows the desired reagent to flow towards the indicated waste tank. For example, if P3 and the control assembly DAb vent valve are opened, the detection antibody will flow through the circuit, through the reaction sites and into the waste chamber W3.

A reaction assembly preferably houses a detection assembly for detecting a signal produced by at least one assay on the fluidic device. FIG. 1 illustrates an exemplary position of a detection device of the present invention in relation to the fluidic device which is below the fluidic device. The detection assembly may be above the fluidic device or at a different orientation in relation to the fluidic device based on, for example, the type of assay being performed and the detection mechanism being employed.

In preferred embodiments an optical detector is used as the detection device. Non-limiting examples include a photodiode, photomultiplier tube (PMT), photon counting detector, or charge-coupled device (CCD). In some embodiments a pin diode may be used. In some embodiments a pin diode can be coupled to an amplifier to create a detection device with a sensitivity comparable to a PMT. Some assays may generate luminescence as described herein. In some embodiments chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

In some embodiments, the detection system may comprise non-optical detectors or sensors for detecting a particular parameter of a patient. Such sensors may include temperature, conductivity, potentiometric, and amperometric, for compounds that are oxidized or reduced, for example, $O_2$, $H_2O_2$, and $I_2$, or oxidizable/reducible organic compounds.

A communication assembly is preferably housed within the reader assembly and is capable of transmitting and receiving information wirelessly from an external device. Such wireless communication may be bluetooth or RTM technology. Various communication methods can be utilized, such as a dial-up wired connection with a modem, a direct link such as a T1, ISDN, or cable line. In preferred embodiments a wireless connection is established using exemplary wireless networks such as cellular, satellite, or pager networks, GPRS, or a local data transport system such as Ethernet or token ring over a local area network. In some embodiments the information is encrypted before it is transmitted over a wireless network. In some embodiments the communication assembly may contain a wireless infrared communication component for sending and receiving information.

In some embodiments the communication assembly can have a memory or storage device, for example localized RAM, in which the information collected can be stored. A storage device may be required if information can not be transmitted at a given time due to, for example, a temporary inability to wirelessly connect to a network. The information can be associated with the fluidic device identifier in the storage device. In some embodiments the communication assembly can retry sending the stored information after a certain amount of time. In some embodiments the memory device can store the information for a period of ten days before it is erased.

In preferred embodiments an external device communicates with the communication assembly within the readers assembly. An external device can wirelessly communicate with a reader assembly, but can also communicate with a third party, including without limitation a patient, medical personnel, clinicians, laboratory personnel, or others in the health care industry.

In some embodiments the external device can be a computer system, server, or other electronic device capable of storing information or processing information. In some embodiments the external device includes one or more computer systems, servers, or other electronic devices capable of storing information or processing information. In some embodiments an external device may include a database of patient information, for example but not limited to, medical records or patient history, clinical trial records, or preclinical trial records. In preferred embodiments, an external device stores protocols to be run on a fluidic device which can be transmitted to the communication assembly of a reader assembly when it has received an identifier indicating which fluidic device has been inserted in the reader assembly. In some embodiments a protocol can be dependent on a fluidic device identifier. In some embodiments the external device stores more than one protocol for each fluidic device. In other embodiments patient information on the external device includes more than one protocol. In preferred embodiments the external server stores mathematical algorithms to process a photon count sent from a communication assembly and in some embodiments to calculate the analyte concentration in a bodily fluid sample.

In some embodiment the external device can include one or more servers as are known in the art and commercially available. Such servers can provide load balancing, task management, and backup capacity in the event of failure of one or more of the servers or other components of the external device, to improve the availability of the server. A server can also be implemented on a distributed network of storage and processor units, as known in the art, wherein the data processing according to the present invention reside on workstations such as computers, thereby eliminating the need for a server.

A server can includes a database and system processes. A database can reside within the server, or it can reside on another server system that is accessible to the server. As the information in a database may contains sensitive information, a security system can be implemented that prevents unauthorized users from gaining access to the database.

One advantage of the present invention is that information can be transmitted from the external device back to not only the reader assembly, but to other parties or other external devices, for example without limitation, a PDA or cell phone. Such communication can be accomplished via a wireless network as disclosed herein. In some embodiments a calculated analyte concentration or other patient information can be sent to, for example but not limited to, medical personal or the patient.

Method of Use

The subject apparatus and systems provide an effective means for high throughput and real-time detection of analytes present in a bodily fluid from a subject. The detection methods may be used in a wide variety of circumstances including identification and quantification of analytes that are associated with specific biological processes, physiological conditions, disorders or stages of disorders. As such, the subject apparatus and systems have a broad spectrum of utility in, e.g. drug screening, disease diagnosis, phylogenetic classification, parental and forensic identification. The subject apparatus and systems are also particularly useful for advancing preclinical and clinical stage of development of therapeutics, improving patient compliance, monitoring ADRs associated with a prescribed drug, and developing individualized medicine.

Accordingly, in one embodiment, the present invention provides a method of detecting an analyte in a bodily fluid from a subject comprises providing a fluidic device comprising at least one sample collection unit, an immunoassay assembly containing immunoassay reagents, a plurality of channels in fluid communication with said sample collection unit and/or said immunoassay assembly; actuating said fluidic device and directing said immunoassay reagents within said fluidic device; allowing a sample of bodily fluid to react with said immunoassay reagents contained within said assay immunoassay assembly to yield a detectable signal indicative of the presence of said analyte in said bodily fluid; and detecting said detectable signal generated from said analyte initially collected in said sample of bodily fluid. Preferably, a sample of bodily fluid of less than about 1 ml, preferably less than about 500 ul is used for one or more of these applications.

As used herein, the term "subject" or "patient" is used interchangeably herein, which refers to a vertebrate, preferably a mammal, more preferably a human. Mammals include, but are not limited to, murines, simians, humans, farm animals, sport animals, and pets.

In some embodiments a sample of bodily fluid can first be provided to the fluidic device by any of the methods described herein. The fluidic device can then be inserted into the reader assembly. An identification detector housed within the reader assembly can detect an identifier of the fluidic device and communicate the identifier to a communication assembly, which is preferably housed within the reader assembly. The communication assembly then transmits the identifier to an external device which transmits a protocol to run on the fluidic device based on the identifier to the communication assembly. A controller preferably housed within the reader assembly controls actuating elements including at least one pump and one valve which interact with the fluidic device to control and direct fluid movement within the device. In some embodiments the first step of the assay is a wash cycle where all the surfaces within the fluidic device are wetted using a wash buffer. The fluidic device is then calibrated using a calibration assembly by running the same reagents as will be used in the assay through the calibration reaction sites, and then a luminescence signal from the reactions sites is detected by the detection means, and the signal is used in calibrating the fluidic device. The sample containing the analyte is introduced into the fluidic channel. The sample may be diluted and further separated into plasma or other desired component at a filter. The separated sample now flows through the reaction sites and analytes present therein will bind to reactants bound thereon. The plasma of sample fluid is then flushed out of the reaction wells into a waste chamber. Depending on the assay being run, appropriate reagents are directed through the reaction sites to carry out the assay. All the wash buffers and other reagents used in the various steps, including the calibration step, are collected in wash tanks. The signal produced in the reaction sites is then detected by any of the methods described herein.

In some embodiments the method of detecting an analyte in a bodily fluid from a subject includes metering a predetermined portion of the sample to be assayed in the sample collection unit and allowing the predetermined portion of the sample to react with assay reagents contained within the assay assembly to yield a signal indicative of the presence of the analyte in the sample.

In one embodiment a subject places a sample of bodily fluid onto the sample collection well, after which the sample is typically drawn into the metering channel by capillary action until it reaches the stop junction at the entrance of the mixing chamber. The metering channel preferably has physical dimensions and surface characteristics which reliably promote flow of blood from the sample collection well. In one preferred version, the metering channel is serpentine so as to provide an adequate sample volume with an acceptable length to cross section ratio and to fit within a constrained footprint. A precise sample volume is determined by several features.

Once the sample enters the metering channel, the fluidic device is inserted into a reader assembly as described herein. The reader assembly actuates a one-time valve closing off the metering channel from the sample collection well. The sample does not enter the diluent flush channel as it is initially sealed from the metering channel.

Diluent is then drawn from the diluent chamber into the metering channel by activating P4 and the vent valve for the dilution chamber, which flushes the sample into the mixing chamber. The pressure is preferably sufficient to break the back pressure at the stop-flow junction.

The sample collection unit allows for a precise sample dilution to occur because, at least, the metering channel and metering element are adapted to provide a predetermined volume of sample to the mixing chamber, and a precise volume of diluent is stored in the dilution chamber, both of which are drawn into the dilution chamber. In some embodiments the serpentine segment of the metering channel between the intersection of the diluent flush channel and the metering channel and the stop junction exactly is 10 ΞL. Because the diluent volume is accurately filled during manufacturing and is completely emptied from the tank during the diluent flush step, the sample is diluted with a high degree of precision.

Figure 4C:
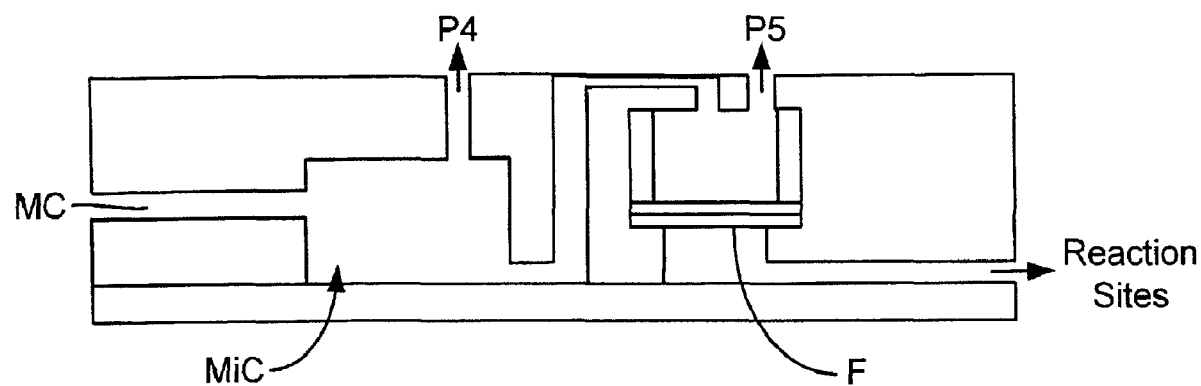
FIG. 4C shows an exemplary fluidic network between a metering channel, a mixing chamber and a filter.

In some embodiments it is desirable to control the flow of fluids into the mixing chamber and/or filter without allowing the fluid to escape the chamber through the outlet. This is illustrated with the side view of the fluidic device in FIG. 4C. The predetermined portion of the sample and the diluent are pulled into the mixing chamber using pump P4, as they simply empty into the mixing chamber by gravity and are not pulled into the filter chamber. This also allows the diluent chamber to be emptied completely without air bubbles entering the mixed solution in the mixing chamber, as air is able to escape through pump P4. The diluted sample is then pulled into the filter chamber with pump P5. Air is similarly able to escape through the top of the filter chamber while the liquid flows down into the filter chamber. The diluted sample is then pulled through the filter and further to the assay assembly. In one embodiment shown in FIG. 4C the filter is a composite of two glass fiber filters.

A variety of assays may be performed on a fluidic device according to the present invention to detect an analyte of interest in a sample. A wide diversity of labels are available in the art that can be employed for conducting the subject assays. In some embodiments labels are detectable by spectroscopic, photochemical, biochemical, immunochemical, or chemical means. For example, useful nucleic acid labels include 32P, 35S, fluorescent dyes, electron-dense reagents, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include radionucleotides, enzymes, substrates, cofactors, inhibitors, fluorescent moieties, chemiluminescent moieties, bioluminescent labels, calorimetric labels, or magnetic particles. Labeling agents optionally include, for example, monoclonal antibodies, polyclonal antibodies, proteins, or other polymers such as affinity matrices, carbohydrates or lipids. Detection proceeds by any of a variety of known methods, including spectrophotometric or optical tracking of radioactive or fluorescent markers, or other methods which track a molecule based upon size, charge or affinity. A detectable moiety can be of any material having a detectable physical or chemical property. Such detectable labels have been well-developed in the field of gel electrophoresis, column chromatograpy, solid substrates, spectroscopic techniques, and the like, and in general, labels useful in such methods can be applied to the present invention. Thus, a label includes without limitation any composition detectable by spectroscopic, photochemical, biochemical, immunochemical, electrical, optical thermal, or chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule is covalently bound to a polymer. The ligand then binds to an anti-ligand molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include luciferin, and 2,3-dihydrophthalazinediones, such as luminol.

Methods of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence by, for example, microscopy, visual inspection, via photographic film, by the use of electronic detectors such as digital cameras, charge coupled devices (CCDs) or photomultipliers and phototubes, or other detection device. Similarly, enzymatic labels are detected by providing appropriate substrates for the enzyme and detecting the resulting reaction product. Finally, simple colorimetric labels are often detected simply by observing the color associated with the label. For example, conjugated gold often appears pink, while various conjugated beads appear the color of the bead.

In some embodiments the detectable signal may be provided by luminescence sources. "Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radioactive decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

Suitable chemiluminescent sources include a compound which becomes electronically excited by a chemical reaction and may then emit light which serves as the detectable signal or donates energy to a fluorescent acceptor. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

In some embodiments immunoassays are run on the fluidic device. While competitive binding assays, which are well known in the art, may be run in some embodiments, in preferred embodiments a two-step method is used which eliminates the need to mix a conjugate and a sample before exposing the mixture to an antibody, which may be desirable when very small volumes of sample and conjugate are used, as in the fluidic device of the present invention. A two-step assay has additional advantages over the competitive binding assays when use with a fluidic device as described herein. It combines the ease of use and high sensitivity of a sandwich (competitive binding) immunoassay with the ability to assay small molecules.

Figure 10:
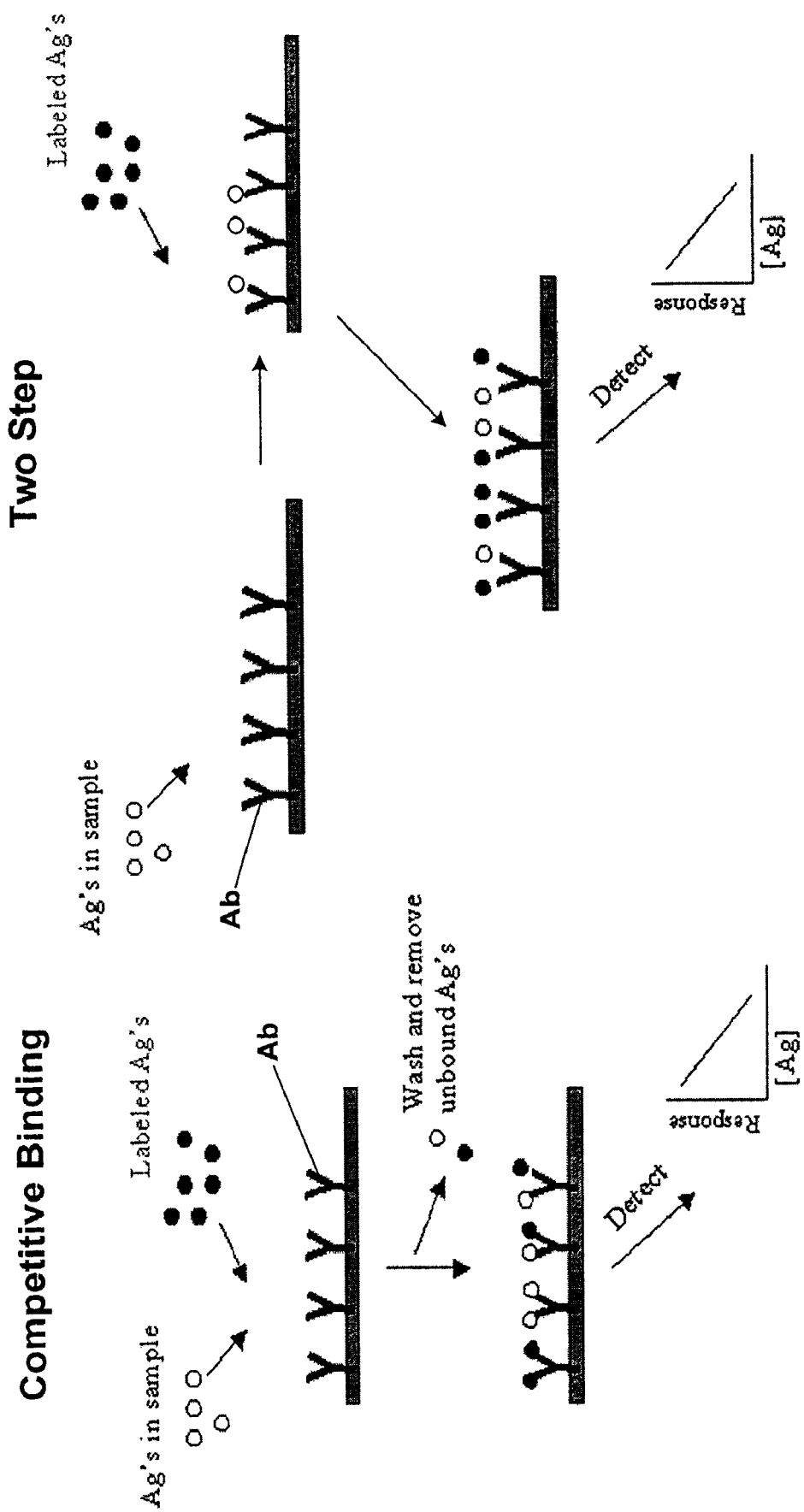
FIG. 10 compares a two-step assay with a competitive binding assay.

In an exemplary two-step assay shown in FIG. 10, the sample containing analyte ("Ag") first flows over a reaction site containing antibodies ("Ab"). The antibodies bind the analyte present in the sample. After the sample passes over the surface, a solution with analyte conjugated to a marker ("labeled Ag") at a high concentration is passed over the surface. The conjugate saturates any of the antibodies that have not yet bound the analyte. Before equilibrium is reached and any displacement of pre-bound unlabelled analyte occurs, the high-concentration conjugate solution is washed off. The amount of conjugate bound to the surface is then measured by the appropriate technique, and the detected conjugate is inversely proportional to the amount of analyte present in the sample.

Figure 11:
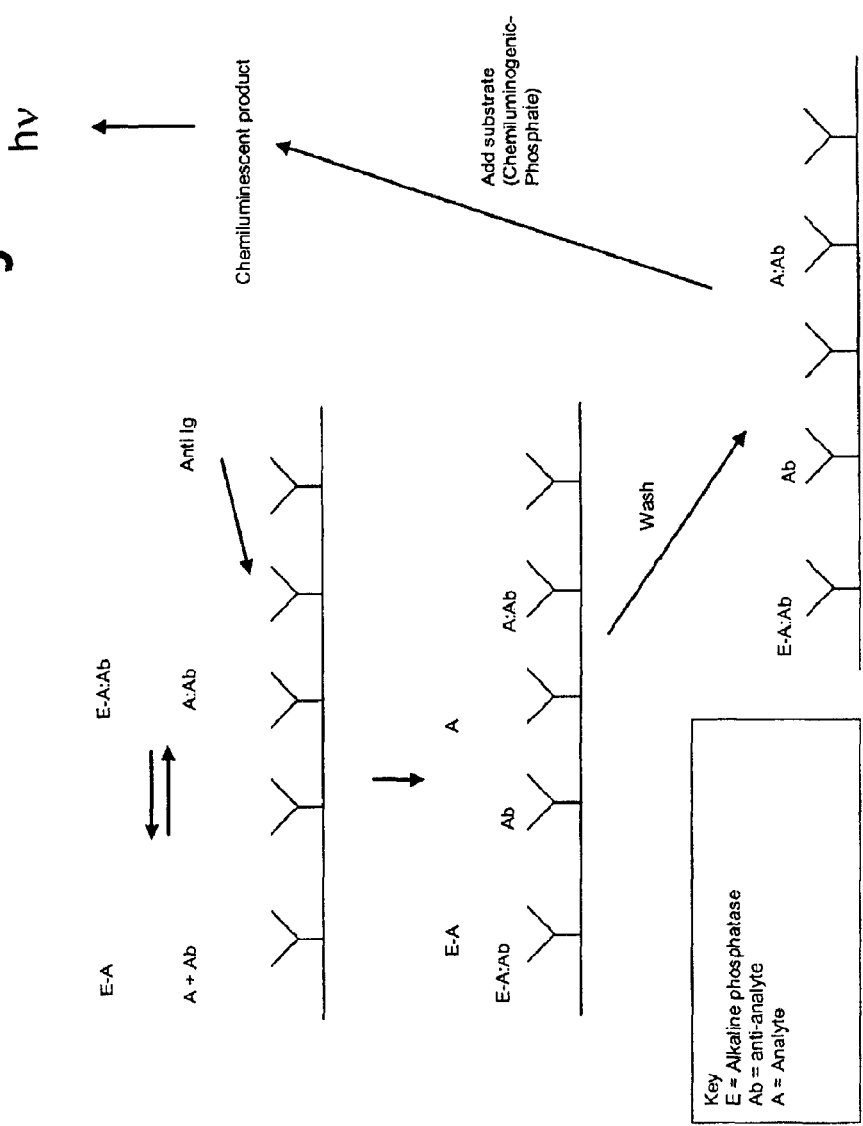
FIG. 11 shows an exemplary two-step chemiluminescence enzyme immunoassay.
Figure 12:
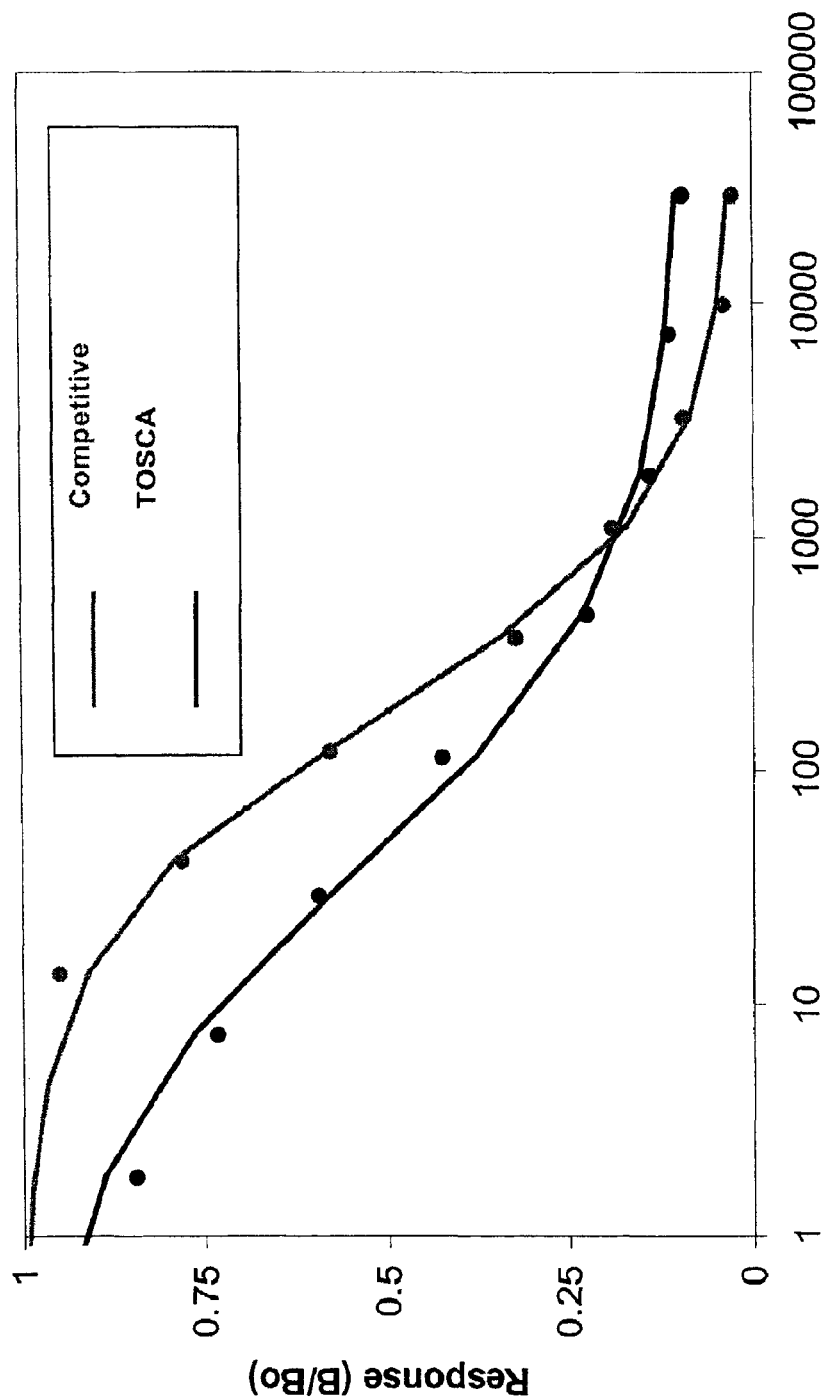
FIG. 12 shows the increased sensitivity of the two-step chemiluminescence enzyme immunoassay.

An exemplary measuring technique for a two-step assay is a chemiluminescence enzyme immunoassay as shown in FIG. 11. As is known in the field, the marker can be a commercially available marker such as dioxitane-phosphate, which is not luminescent but becomes luminescent after hydrolysis by, for example, alkaline phosphatase. An enzyme such as alkaline phosphatase is also passed over the substrate to cause the marker to luminesce. In some embodiments the substrate solution is supplemented with enhancing agents such as, without limitation, fluorescein in mixed micelles, soluble polymers, or PVC which create a much brighter signal than the luminophore alone. Moreover, an alkaline phosphatase conjugate with a higher turnover number than that used in the commercial assay is employed. This allows signal generation to proceed much more rapidly and a higher overall signal is achieved. The increased sensitivity of the two-step chemiluminescent enzyme immunoassay (TOSCA) is illustrated in FIG. 12. FIG. 12 shows that for analytes in the picomolar concentration, TOSCA is able to provide a more robust signal (higher sensitivity) than a competitive binding assay. Use of a two-step binding assay thus contributes to higher sensitivity capabilities of the present invention.

Figure 13:
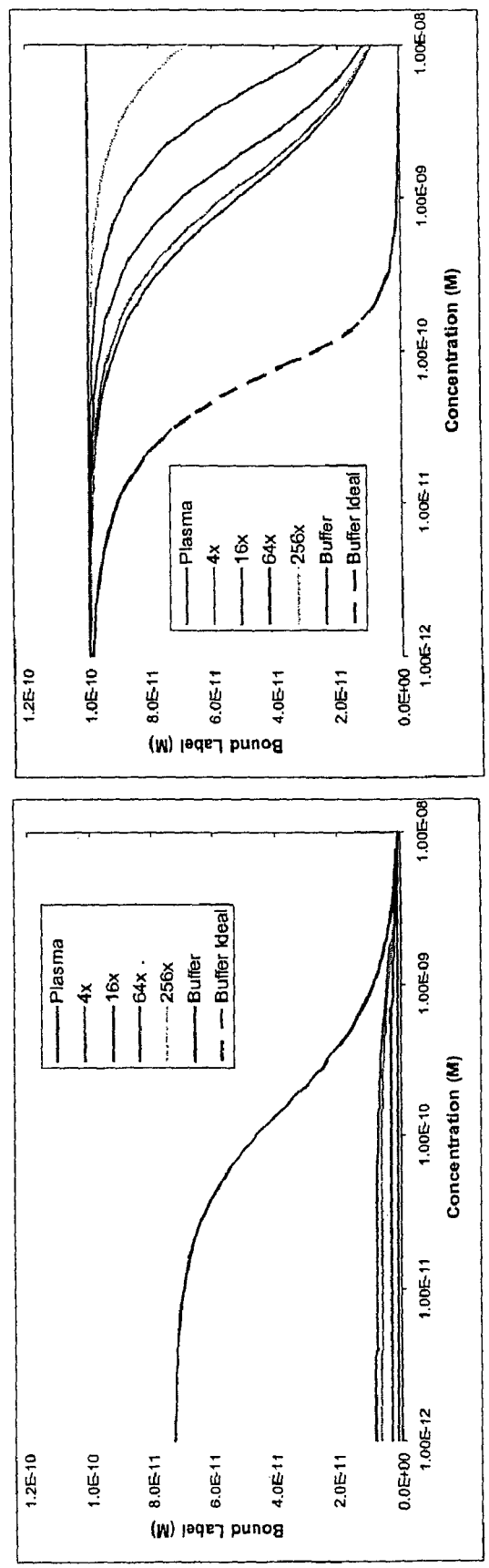
FIG. 13 shows the ability of TOSCA to assay less than ideal samples and maintain desired sensitivity.
Figure 17:
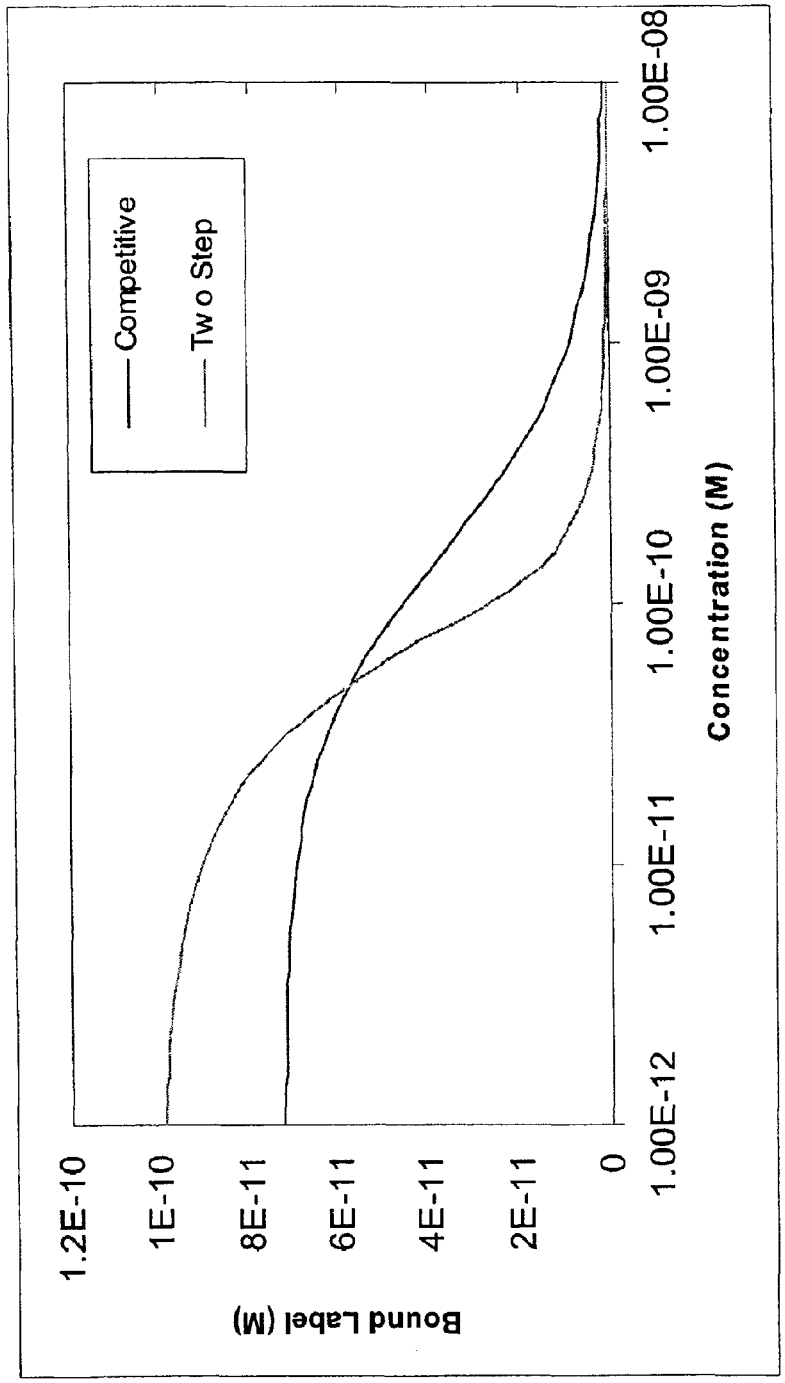
FIG. 17 shows the sensitivity enhancement achieved using TOSCA as compared with competitive binding.

Additionally, TOSCA is less sensitive to matrix effects than other methodologies. This allows one to work with samples that have not been extensively pre-processed using standard laboratory techniques such as, for example, solid phase extraction and chromatography. The ability of TOSCA to assay less than ideal samples and maintain desired sensitivity is illustrated in FIG. 13. Compared to competitive binding assay, for all sample preparations (and dilutions), TOSCA has better sensitivity than competitive binding. This is also illustrated in FIG. 17 where the sensitivity enhancement achieved using TOSCA is compared with the two-step assay.

The term "analytes" according to the present invention includes without limitation drugs, prodrugs, pharmaceutical agents, drug metabolites, biomarkers such as expressed proteins and cell markers, antibodies, serum proteins, cholesterol, polysaccharides, nucleic acids, biological analytes, biomarker, gene, protein, or hormone, or any combination thereof. At a molecular level, the analytes can be polypeptide glycoprotein, polysaccharide, lipid, nucleic acid, and a combination thereof.

Of particular interest are biomarkers are associated with a particular disease or with a specific disease stage. Such analytes include but are not limited to those associated with autoimmune diseases, obesity, hypertension, diabetes, neuronal and/or muscular degenerative diseases, cardiac diseases, endocrine disorders, any combinations thereof.

Of also interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are analytes that are indicative of a microorganism. Exemplary microorganisms include but are not limited to bacterium, virus, fungus and protozoa. Analytes that can be detected by the subject method also include bloodborn pathogens selected from a non-limiting group that consists of *Staphylococcus epidermidis, Escherichia coli,* methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influnzae, Staphylococcus simulans, Streptococcus pneumoniae* and *Candida albicans.*

Analytes that can be detected by the subject method also encompass a variety of sexually transmitted diseases selected from the following: gonorrhea (*Neisseria gorrhoeae*), syphilis (*Treponena pallidum*), clamydia (*Clamyda tracomitis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Additional analytes that can be detected by the subject methods encompass a diversity of respiratory pathogens including but not limited to *Pseudomonas aeruginosa,* methicillin-resistant *Staphlococcus aureus* (MSRA), *Klebsiella pneumoniae, Haemophilis influenzae, Staphlococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae,* and *Mycobacterium tuberculosis.*

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, High sensitivity CRP, Triglycerides, Tryptase, Low density lipoprotein Cholesterol, High density lipoprotein Cholesterol, Cholesterol, IGFR.

Exemplary liver markers include without limitation LDH, (LD5), (ALT), Arginase 1 (liver type), Alpha-fetoprotein (AFP), Alkaline phosphatase, Alanine aminotransferase, Lactate dehydrogenase, and Bilirubin.

Exemplary kidney markers include without limitation TNFα Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markes include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancrease markers include without limitation Amylase, Pancreatitis-Associated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx) Carboxyterminal cross-linking telopeptide of bone collagen, Lysyl-pyridinoline (deoxypyridinoline), Pyridinoline, Tartrate-resistant acid phosphatase, Procollagen type I C peptide, Procollagen type I N propeptide, Osteocalcin (bone glaprotein), Alkaline phosphatase, Cathepsin K, COMP (Cartilage Oligimeric Matrix Protein), Osteocrin Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease markers include without limitation Viremia, Bacteremia, Sepsis, PMN Elastase, PMN elastase/α1-PI complex, Surfactant Protein D (SP-D), HBVc antigen, HBVs antigen, Anti-HBVc, Anti-HIV, T-supressor cell antigen, T-cell antigen ratio, T-helper cell antigen, Anti-HCV, Pyrogens, p24 antigen, Muramyl-dipeptide.

Exemplary diabetes markers include without limitation C-Peptide, Hemoglobin Alc, Glycated albumin, Advanced glycosylation end products (AGEs), 1,5-anhydroglucitol, Gastric Inhibitory Polypeptide, Glucose, Hemoglobin, ANGPTL3 and 4.

Exemplary inflammation markers include without limitation Rheumatoid factor (RF), Antinuclear Antibody (ANA), C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. COX inhibitors include without limitation TxB2 (Cox-1), 6-keto-PGF-1-alpha (Cox 2), 11-Dehydro-TxB-1a (Cox-1).

Other markers of the present include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4) Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor).

Exemplary markers of Lipid metabolism include without limitation Apo-lipoproteins (several), Apo-A1, Apo-B, Apo-C-CII, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII: Antihemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1).

Exemplary monoclonal antibodies include those for EGFR, ErbB2, and IGF1R.

Exemplary tyrosine kinase inhibitors include without limitation Abl, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threoline Kinas Inhibitors include without limitation AKT, Aurora A/B/B, CDK, CDK (pan), CDK1-2, VEGFR2, PDGFRb, CDK4/6, MEK1-2, mTOR, and PKC-beta.

GPCR targets include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

In a separate embodiment, the present invention provides a method of monitoring more than one pharmacological parameter useful for assessing efficacy and/or toxicity of a therapeutic agent. The method comprises subjecting a sample of bodily fluid from a subject administered with the therapeutic agent to a fluidic device for monitoring said more than one pharmacological parameter, said fluidic device comprising at least one sample collection unit, and an assay assembly comprising reaction reagents; actuating said fluidic device and directing said immunoassay reagents within said fluidic device; allowing said sample of bodily fluid to react with immunoassay reagents to yield detectable signals indicative of the values of the more than one pharmacological parameter from said sample; and detecting said detectable signal generated from said sample of bodily fluid. Where desired, the method further involves repeating the steps at a time interval prompted by a wireless signal communicated to the subject.

For the purposes of this invention, a "therapeutic agent" is intended to include any substances that have therapeutic utility and/or potential. Such substances include but are not limited to biological or chemical compounds such as a simple or complex organic or inorganic molecules, peptides, proteins (e.g. antibodies) or a polynucleotides (e.g. anti-sense). A vast array of compounds can be synthesized, for example polymers, such as polypeptides and polynucleotides, and synthetic organic compounds based on various core structures, and these are also included in the term "therapeutic agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

Pharmacodynamic (PD) parameters according to the present invention include without limitation physical parameters such as temperature, heart rate/pulse, blood pressure, and respiratory rate, and biomarkers such as proteins, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters in real time from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the pharmacodynamic (PD) parameters fall outside the desired range during a treatment regime, immediate action may have to be taken as well.

In preferred embodiments physical parameter data is stored in or compared to store profiles of physical parameter data in a bioinformatics system which may be on an external device incorporating pharmacogenomic and pharmacokinetic data into its models for the determination of toxicity and dosing. Not only does this generate data for clinical trials years prior to current processes but also enables the elimination of current disparities between apparent efficacy and actual toxicity of drugs through real-time continuous monitoring. During the go/no go decision process in clinical studies, large scale comparative population studies can be conducted with the data stored on the database. This compilation of data and real-time monitoring allows more patients to enter clinical trials in a safe fashion earlier than currently allowed. In another embodiment biomarkers discovered in human tissue studies can be targeted by the device for improved accuracy in determining drug pathways and efficacy in cancer studies.

In another embodiment, the present invention provides a method of detecting at least two distinct analytes of different concentrations in a bodily fluid from a subject comprises providing a fluidic device comprising a sample collection unit, an assay assembly, and a plurality of channels in fluid communication with said sample collection unit and/or said assay assembly; allowing a sample of bodily fluid to react with a plurality of reactants contained in said assay assembly to yield signals indicative of the concentrations of said at least two analytes; and detecting said signals that are indicative of the presence or absence of the at least two distinct analytes, wherein said signals are detectable over a range of 3 orders of magnitude.

Figure 18:
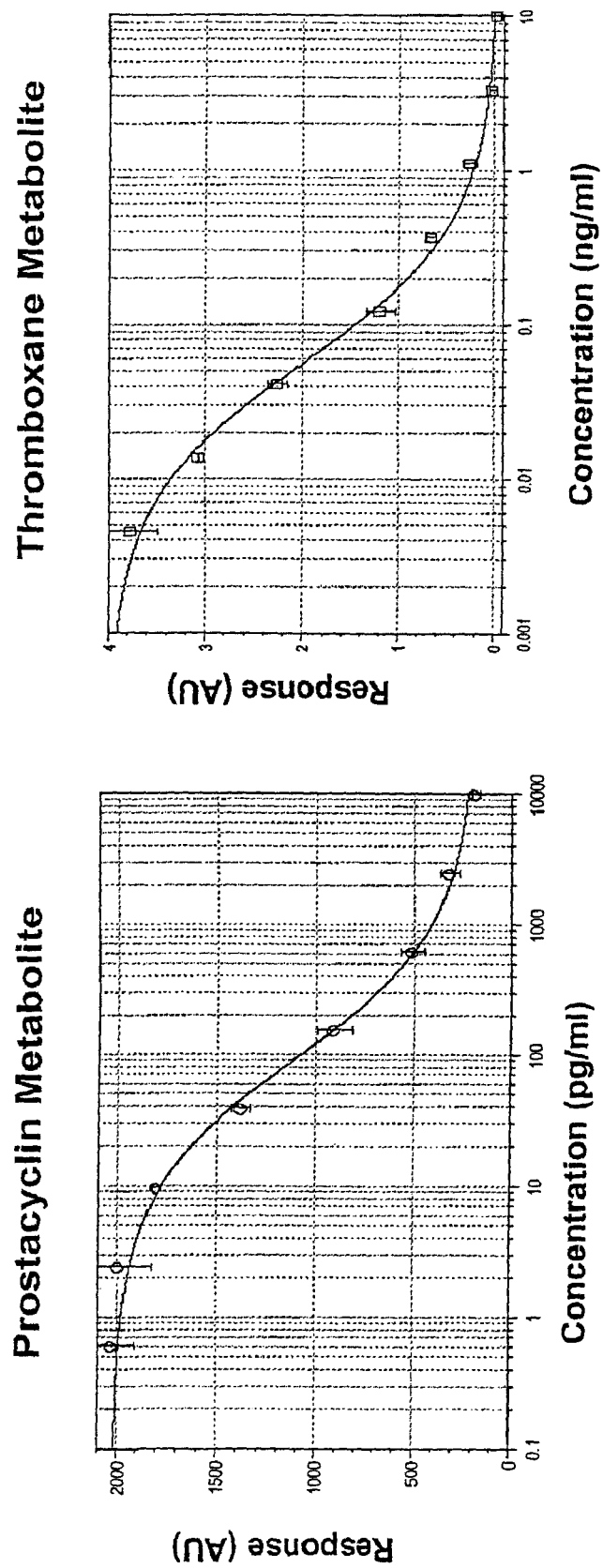
FIG. 18 shows two analytes, prostacyclin metabolite and thromboxane metabolite, which have been identified and quantified and their concentrations are different by more than 3 orders of magnitude.

Currently, a need exists for the detecting more than one analyte where the analytes are present in widely varying concentration range, for example, one analyte is in the pg/ml concentration and another is in the ng/ml concentration. TOSCA described herein has the ability to simultaneously assay analytes that are present in the same sample in a wide concentration range. FIG. 18 shows one embodiment where two analytes, prostacyclin metabolite and thromboxane metabolite, have been identified and quantified and their concentrations are different by more than 3 orders of magnitude. Another advantage for being able to detect concentrations of different analytes present in a wide concentration range is the ability to relate the ratios of the concentration of these analytes to safety and efficacy of multiple drugs administered to a patient. For example, unexpected drug-drug interactions can be a common cause of adverse drug reactions. A real-time, concurrent measurement technique for measuring different analytes would help avoid the potentially disastrous consequence of adverse drug-drug interactions.

Being able to monitoring the rate of change of an analyte concentration or PD or PK over a period of time in a single subject, or performing trend analysis on the concentration, PD, or PK, whether they are concentrations of drugs or their metabolites, can help prevent potentially dangerous situations. For example, if glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

Accordingly, the present invention provides a method of performing a trend analysis on the concentration of an analyte in a subject. The method comprise a) providing a fluidic device comprising at least one sample collection unit, an immunoassay assembly containing immunoassay reagents, a plurality of channels in fluid communication with said sample collection unit and/or said immunoassay assembly; b) actuating said fluidic device and directing said immunoassay reagents within said fluidic device; c) allowing a sample of bodily fluid of less than about 500 ul to react with said immunoassay reagents contained within said assay immunoassay assembly to yield a detectable signal indicative of the presence of said analyte in said sample; d) detecting said detectable signal generated from said analyte collected in said sample of bodily fluid; and e) repeating steps a) through d) for a single patient over a period of time to detect concentrations of said anayte, thereby performing said trend analysis.

In some embodiments, a method of detecting an analyte in a bodily fluid from a subject using an assay transmitted from an external device is provided. The method comprises providing a fluidic device comprising at least one sample collection unit and an immunoassay assembly containing immunoassay reagents; detecting said fluidic device and wirelessly transmitting an immunoassay protocol to said device; allowing a sample of bodily fluid to react with immunoassay reagents to yield a detectable signal indicative of the presence of said analyte using said transmitted immunoassay protocol; and detecting said detectable signal.

Communication between a reader assembly and an external storage device allows for a reader assembly of the present invention to download a fluidic device-specific protocol to run on the fluidic device based on the identity of the fluidic device. This allows a reader assembly to be used interchangeably with any appropriate fluidic device described herein. In addition, the external device can store a plurality of protocols associated with a given fluidic device, and depending on, for example, a subject's treatment regime or plan, different protocols can be communicated from the external device to the reader assembly to be run on the fluidic device to detect a variety of analytes. The external device can also store a plurality of protocols associated not only with a fluidic device, but also with a particular subject or subjects, such that a protocol can be associated with a subject as well as with a fluidic device.

In some embodiments, the present invention provides a business method of assisting a clinician in providing an individualized medical treatment comprises collecting at least one pharmacological parameter from an individual receiving a medication, said collecting step is effected by subjecting a sample of bodily fluid to reactants contained in a fluidic device, which is provided to said individual to yield a detectable signal indicative of said at least one pharmacological parameter; and cross referencing with the aid of a computer medical records of said individual with the at least one pharmacological parameter of said individual, thereby assisting said clinician in providing individualized medical treatment.

The present invention allows for automatic quantification of a pharmacological parameter of a patient as well as automatic comparison of the parameter with, for example, the patient's medical records which may include a history of the monitored parameter, or medical records of another group of subjects. Coupling real-time analyte monitoring with an external device which can store data as well as perform any type of data processing or algorithm, for example, provides a device that can assist with typical patient care which can include, for example, comparing current patient data with past patient data. The present invention therefore creates a business method which effectively performs at least part of the monitoring of a patient that is currently performed by medical personnel.

In some embodiments, the present invention provides a business method of monitoring a clinical trial of a pharmaceutical agent comprises collecting at least one pharmacological parameter from a subject in said clinical trial at a plurality of time intervals, said collecting step is effected at each time interval by subjecting a sample of bodily fluid from said subject to reactants contained in a fluidic device, wherein said fluidic device is provided to said subject to yield detectable signals indicative of the values of said at least one pharmacological parameter at a plurality of time intervals; comparing the detected values to a threshold value predetermined for said pharmacological parameter; notifying a clinician and/or a sponsor involved in said clinical trial when a statistically significant discrepancy exists between the detected values and the threshold value.

Figure 19:
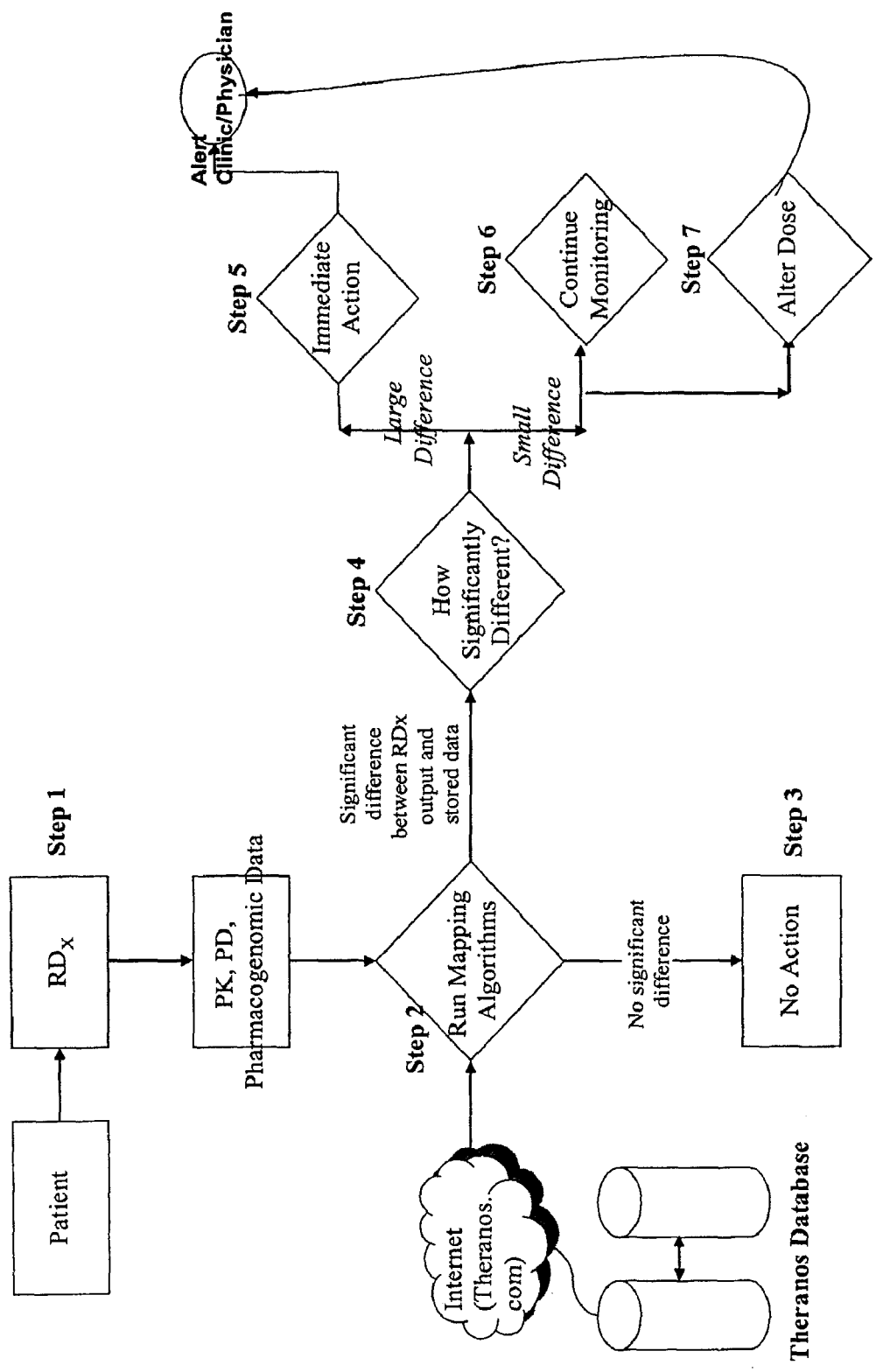
FIG. 19 shows an exemplary flow chart of a business method of monitoring a clinical trial of a therapeutic agent.

FIG. 19 shows an exemplary flow chart of a business method of monitoring a clinical trial of a pharmaceutical agent. As disclosed herein, a fluidic device gathers PK and/or PD parameters related to a patient of interest. The data is securely transmitted over, for example, a cellular network or the interne, and interpretations of the data are derived through computations in a series of biostatistical algorithms on the external device which correlate pharamcodynamic, pharmacokinetic, and pharmacogenetic profiles. Additionally, the data can be compared with information stored in databases. The stored information could be the patient's own PK and PD data over a previous treatment regiment, data related to placebo, pharmacogenomic data that are of relevance to the particular patient, or data related to a group of subjects. If the analysis done in Step 2 suggests that there are no significant difference between the patient's data and the stored data, as determined by using appropriate algorithms, then "No Action" is taken. However, if there is a significant difference, then Step 4 determines the size of the difference. If the difference is large, immediate action is taken. An exemplary type of immediate action could be to provide an emergency alert to the patient's healthcare provider. Another kind of immediate action could be to send instructions to the fluidic device to alter the dosing of the pharmaceutical agent. If in Step 4 the difference is small, then the algorithm could determine whether to continue monitoring the parameters and/or alter a dosage of the pharmaceutical agent. This method provides for automatic notification to at least medical personnel or a subject of a possible need to take additional medical action.

Where a statistically significant discrepancy exists between the detected values and the threshold value, a further action may be taken by a medical practitioner. Such action may involve a medical action such as adjusting dosage of the therapeutic agent; it may also involve a business decision such as continuing, modifying, or terminating the clinical trial.

Figure 20:
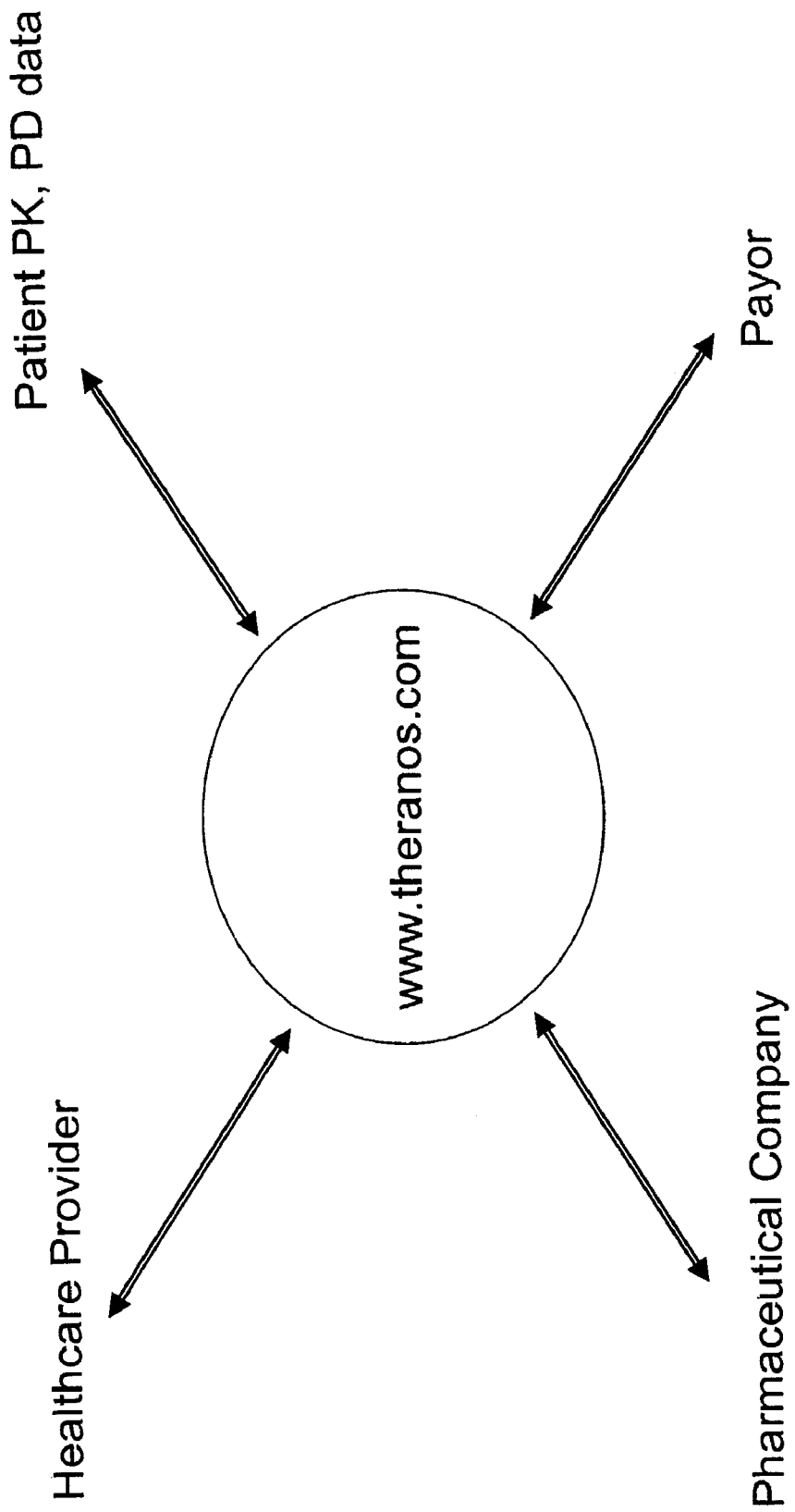
FIG. 20 shows simultaneous sharing of the information detected with a fluidic device with various interested parties.

One of the significant advantages of the envisioned network is illustrated in FIG. 20. As all the information is securely channeled through the interne, this allows the simultaneous sharing of the information with various interested parties, while satisfying the appropriate clinical, regulatory and business needs. For example, the flowchart shows how the patient's clinical needs are met. The ability of the company that is sponsoring a drug study, for example a clinical trial or a post-market Phase IV surveillance, to monitor in real-time the safety and efficacy of the performance of the drug provides extremely valuable regulatory and business information. Similarly, the ability of a payor to monitor the efficacy, and perhaps cost-effectiveness, of a treatment is greatly enhanced by their ability to obtain data in real-time.

In some embodiments, the present invention provides a method of transmitting a pharmacological parameter of a patient via a handheld device comprises providing a fluidic device comprising at least one sample collection unit and an assay assembly; allowing a sample of bodily fluid to react with reactants contained within said assay assembly to yield a detectable signal indicative of the presence of said analyte; detecting said detectable signal; transmitting said signal to an external device; processing said signal in said external device; and transmitting said processed signal via a handheld device.

One advantage of the current invention is that assay results can be substantially immediately communicated to any third party that may benefit from obtaining the results. For example, once the analyte concentration is determined at the external device, it can be transmitted to a patient or medical personnel who may need to take further action. The communication step to a third party can be performed wirelessly as described herein, and by transmitting the data to a third party's hand held device, the third party can be notified of the assay results virtually anytime and anywhere. Thus, in a time-sensitive scenario, a patient may be contacted immediately anywhere if urgent medical action may be required.

In some embodiments a method of automatically selecting a protocol to be run on a fluidic device comprises providing a fluidic device comprising an identifier detector and an identifier; detecting said identifier with said identifier detector; transferring said identifier to an external device; and selecting a protocol to be run on said fluidic device from a plurality of protocols on said external device associated with said identifier.

By detecting each fluidic device based on an identifier associated with the fluidic device after it is inserted in the reader assembly, the system of the present invention allows for fluidic device-specific protocols to be downloaded from an external device and run on the fluidic device. In some embodiments the external device can store a plurality of protocols associated with the fluidic device or associated with a particular patient or group of patients. For example, when the identifier is transmitted to the external device, software on the external device can obtain the identifier. Once obtained, software on the external device, such as a database, can use the identifier to identify protocols stored in the database associated with the identifier. If only one protocol is associated with the identifier, for example, the database can select the protocol and software on the external device can then transmit the protocol to the communication assembly on the reader assembly. The ability to use protocols specifically associated with a fluidic device allows for any appropriate fluidic device to be used with a single reader assembly, and thus virtually any analyte of interest can be detected with a single reader assembly.

In some embodiments multiple protocols may be associated with a single identifier. For example, if it is beneficial to detect from the same patient an analyte once a week, and another analyte twice a week, protocols on the external device associated with the identifier can also each be associated with a different day of the week, so that when the identifier is detected, the software on the external device can select a specific protocol that is associated with the day of the week.

In some embodiments a patient may be provided with a plurality of fluidic devices to use to detect a variety of analytes. A subject may, for example, use different fluidic devices on different days of the week. In some embodiments the software on the external device associating the identifier with a protocol may include a process to compare the current day with the day the fluidic device is to be used based on a clinical trial for example. If for example, the two days of the week are not identical, the external device can wirelessly send notification to the subject using any of the methods described herein or known in the art to notify them that an incorrect fluidic device is in the reader assembly and also of the correct fluidic device to use that day. This example is only illustrative and can easily be extended to, for example, notifying a subject that a fluidic device is not being used at the correct time of day.

In some embodiments, the present invention provides a method of manufacturing a fluidic device for detecting an analyte in a biological fluid of a subject comprises providing a plurality of layers of a material. The method comprises providing a plurality of layers of a fluidic device, and ultrasonically welding said layers together such that a fluidic network exists between a sample collection unit, at least one reactant chamber, at least one reaction site, and at least one waste chamber. Where desired, the fluidic device manufactured by this method comprise in at least one of said layers a sample collection unit, at least one of said layers comprises a filtration site, and at least one of said layers comprises a reactant chamber, and at least one of said layers comprises a fluidic channel, and at least one of said layers comprises a reaction site, and at least one of said layers comprises a waste chamber.

In preferred embodiments the different layers of the fluidic device are ultrasonically welded together according to methods known in the art. The layers may also be coupled together using other methods, including without limitation stamping, thermal bonding, adhesives or, in the case of certain substrates, e.g., glass, or semi-rigid and non-rigid polymeric substrates, a natural adhesion between the two components.

In some embodiments, the present invention provides a method of obtaining pharmacological data useful for assessing efficacy and/or toxicity of a pharmaceutical agent from a test animal. The method involves the steps of a) providing a fluidic device comprising at least one sample collection unit, an assay assembly; and a plurality of channels in fluid communication with said sample collection unit and/or said assay assembly; b) allowing a sample of biological fluid of less than about 50 ul to react with reactants contained within said assay assembly to yield a detectable signal generated from an analyte initially collected in said sample that is indicative of a pharmacological parameter; and c) detecting said detectable signal; and d) repeating the reaction and detection steps with a second sample of biological fluid from the same test animal. In a related embodiment, the present invention provides a method comprising a) providing a fluidic device comprising at least one sample collection unit, an assay assembly; and a plurality of channels in fluid communication with said sample collection unit and/or said assay assembly; b) allowing a sample of biological fluid to react with reactants contained within said assay assembly to yield a detectable signal generated from an analyte initially collected in said sample that is indicative of a pharmacological parameter; and c) detecting said detectable signal; and d) repeating the reaction and detection steps with a second sample of biological fluid from the same test animal, wherein the animal is not subjected to anesthesia.

When using laboratory animals in preclinical testing of a pharmaceutical agent, it is often necessary to kill the test subject to extract enough blood to perform an assay to detect an analyte of interest. This has both financial and ethical implications, and as such it may be advantageous to be able to draw an amount of blood from a test animal such that the animal does not need to be killed. In addition, this can also allow the same test animal to be tested with multiple pharmaceutical agents at different times, thus allowing for a more effective preclinical trial. On average, the total blood volume in a mouse, for example, is 6-8 mL of blood per 100 gram of body weight. A benefit of the current invention is that only a very small volume of blood is required to perform preclinical trials on mice or other small laboratory animals. In some embodiment between about 1 microliter and about 50 microliters are drawn. In preferred embodiment between about 1 microliter and 10 microliters are drawn. In preferred embodiments about 5 microliters of blood are drawn.

A further advantage of keeping the test animal alive is evident in a preclinical time course study. When multiple mice, for example, are used to monitor the levels of an analyte in a test subject's bodily fluid over time, the added variable of using multiple subjects is introduced into the trial. When, however, a single test animal can be used as its own control over a course of time, a more accurate and beneficial preclinical trial can be performed.

In some embodiments a method of automatically monitoring patient compliance with a medical treatment using a fluidic device comprises allowing a sample of bodily fluid to react with assay reagents in a fluidic device to yield a detectable signal indicative of the presence of an analyte in said sample; detecting said signal with said fluidic device; comparing said signal with a known profile associated with said medical treatment to determine if said patient is compliant or noncompliant with said medical treatment; and notifying a patient of said compliance or noncompliance.

Noncompliance with a medical treatment, including a clinical trial, can seriously undermine the efficacy of the treatment or trial. As such, in some embodiments the system of the present invention can be used to monitor patient compliance and notify the patient or other medical personnel of such noncompliance. For example, a patient taking a pharmaceutical agent as part of medical treatment plan can take a bodily fluid sample which is assayed as described herein, but a metabolite concentration, for example, detected by the reader assembly may be at an elevated level compared to a known profile that will indicate multiple doses of the pharmaceutical agent have been taken. The patient or medical personnel may be notified of such noncompliance via any or the wireless methods discussed herein, including without limitation notification via a handheld device such a PDA or cellphone. Such a known profile may be located or stored on an external device described herein.

In some embodiments noncompliance may include taking an improper dose of a pharmaceutical agent including without limitation multiple doses and no doses, or may include inappropriately mixing pharmaceutical agents. In preferred embodiments a patient is notified substantially immediately after the signal is compared with a known profile.

A patient or subject of a clinical trial may forget to take a bodily fluid sample as described herein. In some embodiments a method of alerting a patient to test a sample of bodily fluid using a fluidic device as described herein comprises providing a protocol to be run on said fluid device, said protocol located on an external device, associated with said patient, and comprising a time and date to test said sample of bodily fluid; and notifying patient to test said bodily fluid on said date and time if said sample has not been tested. In some embodiments a patient can be notified wirelessly as described herein.

A patient may be provided with a fluidic device or devices when procuring a prescription of drugs by any common methods, for example, at a pharmacy. Likewise, a clinical trial subject may be provided with such devices when starting a clinical trial. The patient or subject's contact information, including without limitation cell phone, email address, text messaging address, or other means of wireless communication, may at that time be entered into the external device and associated with the patient or subject as described herein, for example, in a database. Software on the external device may include a script or other program that can detect when a signal generated from a detection device has not yet been sent to the external device, for example at a given time, and the external device can then send an alert notifying the patient to take a bodily fluid sample.

In some embodiments the present invention provides a method of assessing the reliability of an assay for an analyte in a bodily fluid with the use of a fluidic device. The method comprises the steps of a) providing a system, said system comprising a fluidic device, said fluidic device comprising a sample collection unit and an assay assembly, wherein said sample collection unit allows a sample of bodily fluid to react with reactants contained within said assay assembly, for detecting the presence of an analyte in a bodily fluid from a subject, and a reader assembly for detecting the presence of said analyte; and b) sensing with a sensor a change in operation parameters under which the system normally operates.

In some aspects a sensor may be present either in the fluidic device, the reader assembly, both, or in some cases it may be advantageous to include a sensor in the packaging in which the fluidic device and/or reader assembly are packaged. The sensor can, for example without limitation, detect temperate or pressure changes that may provide for an inaccurate analyte concentration calculation. For example, if the temperature of reagents stored in said fluidic device falls outside an acceptable temperature range, this may indicate that the detection will not be accurate using the then existing calibration and processing algorithms, for example. Likewise, for example, the pressure in the pump in the reader assembly may fall outside an acceptable range. In some embodiments a moisture sensor is provided to detect the presence of moisture in the cartridge before the assay begins. In some embodiments there may be thiosyanate in one layer of the fluidic device and iron salt in another layer, wherein a dye is formed when these are mixed, whereby the dye is a visual indication of the presence of moisture.

In some disposable systems, particularly in those where sample acquisition is performed by the patient or end user, measurement errors are not uncommon Significant errors due to, for example, patient handling of the sample, could be due to the sample collection method. A patient may not collect the correct volume of the sample, the collection may not be performed at the appropriate time, or the sample may not be handled in an appropriate manner, thus compromising the sample integrity. It may be advantageous when using a disposable system in which the patient controls the initial sample collection and handling to utilize methods for minimizing the consequences of such errors by, for example, either alerting the patient to repeat the test or use calibration steps to compensate for such errors.

There is therefore a significant need for methods that would improve the calibration in hand held or disposable assay units, particularly in those units where the sample and reagent volumes are in the microliter and nanoliter ranges, where maintaining a controlled temperature is impractical, where the sample is not "clean" such that errors are caused by interfering substances, such as hematocrit, for example, or where it is difficult to maintain the desired conditions such as temperature or reagent quality, including the appropriate sample volume and handling by the user.

Immunoassays have a characteristic response similar in form to the well-known Scatchard binding isotherm (Bound/Maximum Bound (B/B0)=Ligand Concentration/(K+Ligand Concentration) where B is the amount of the labeled analyte bound to a solid phase when analyte is present, B0 is the amount bound when no analyte is present and K is the dissociation constant. The mathematical form of such assay responses is hyperbolic.

Figure 21:
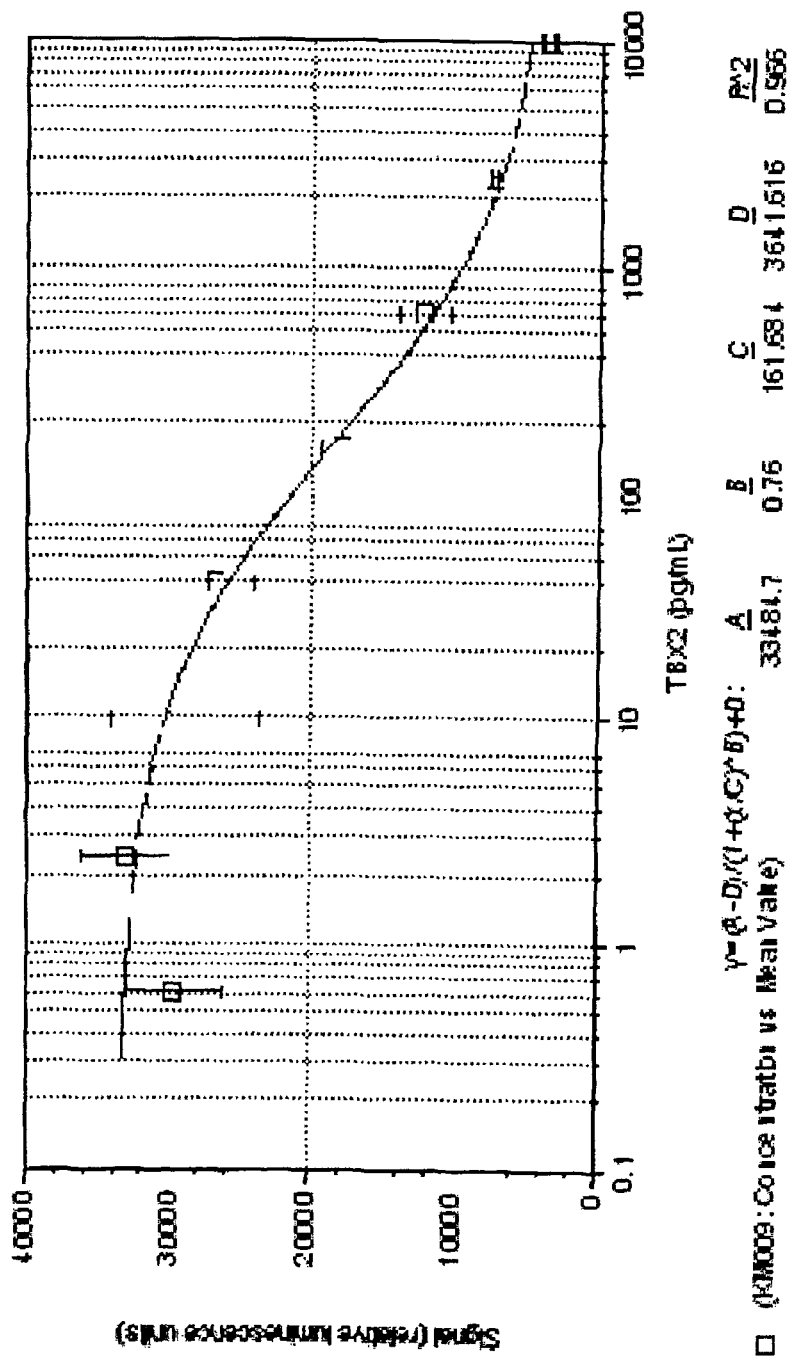
FIG. 21 shows a typical assay dose-response data for a two-step assay for TxB2.

Results of immunoassays of the types described above are typically analyzed using the known (ln-logit) or (log-logit) functions, in which the assay label (for example in a two-step process, alkaline phosphatase-labeled analyte) bound to a solid phase when analyte is present in the assay ("B") is compared with the amount bound when no analyte is present ("B0") to provide the ratio B/B0. Then, the "logit" function (logit=Log[(B/B0)/(1−B/B0)]) is plotted against Log (Analyte Concentration) resulting in a straight line. (Natural logarithms can also be used instead of logarithms to base 10). The slope and intercept of this plot can be used to derive simple equations that permit the calculation of (a) assay signal as a function of analyte concentration, or (b) analyte concentration as a function of assay signal. An example of such analysis is shown in FIG. 21 using Thromboxane as the analyte of interest. The best fit to the data is given by Equation 1: Signal=(A−D)/(1+(Analyte conc./C)^B)+D [Equation 1], where A is the signal at zero analyte concentration, D is the signal at infinite analyte concentration, C is the analyte concentration reached at a signal level half way between A and D, and B is a shape parameter. The relationship between analyte concentration and signal is given by: Analyte concentration=C*((((A−D)/(Signal−D)−1)^(1/B)) [Equation 2], where A, B, C and D are identical to the parameters used in Equation 1.

It is possible to compute errors that occur from mis-calibration using the equations described herein above. (The Analyte Concentration function from Equation 2 is differentiated with respect to each potential variable A, B, C, D and Signal). Estimates of the difference between the ideal value of the variable and the actual value in the system are used as $\Delta$ values in the calculation ($\Delta$(concentration)=(d(Concentration)/d(Param.))*$\Delta$ Param). Errors in calibration are reflected in erroneous values of A, B, C and D. Each of these parameters is influenced by a different factor. For example, temperature effects on calibration of immunoassays will have the strongest impact on the A, C and D parameters of the ln-logit calibration, while likely having a minimal impact on the shape parameter B. The detected signal, which in turn can be used to determine the analyte concentration, is biased by one or more of the following reader assembly and fluidic device characteristics: optics used in the instrument for signal measurement; temperature control; most chemical processes are highly temperature sensitive, including enzyme reactions, and equilibrium between antigens and antibodies; timing of assay steps; calibration relative to an "ideal" instrument; the inability of the patient to manually recalibrate the fluidic device when used; dimensions of the fluidic device; volume of the assay assembly and its shape; fluid movement within the device; timing and uniformity of fluid movement; efficiency in mixing (most assay methods used in disposables and employ microfluidics would involve some mixing). The following reagent variations can also contribute to a biased detected signal: reagent quantity; reagent dissolution (if it is in dry form); changes in activity of reagents following manufacture (instability) (This is particularly important for "distributed systems" where the disposable useful life is typically determined by reagents which can, for example, lose 20% of their activity. If they can be used without significantly compromising assay performance, the shelf-life of many expensive disposables could be extended several fold and severe constraints on disposable storage (refrigeration and the like) can be relaxed). In addition, when calibration is performed at the factory, small errors in the estimation of the calibration parameters can result in error in the calculated analyte concentration.

Figure 22:
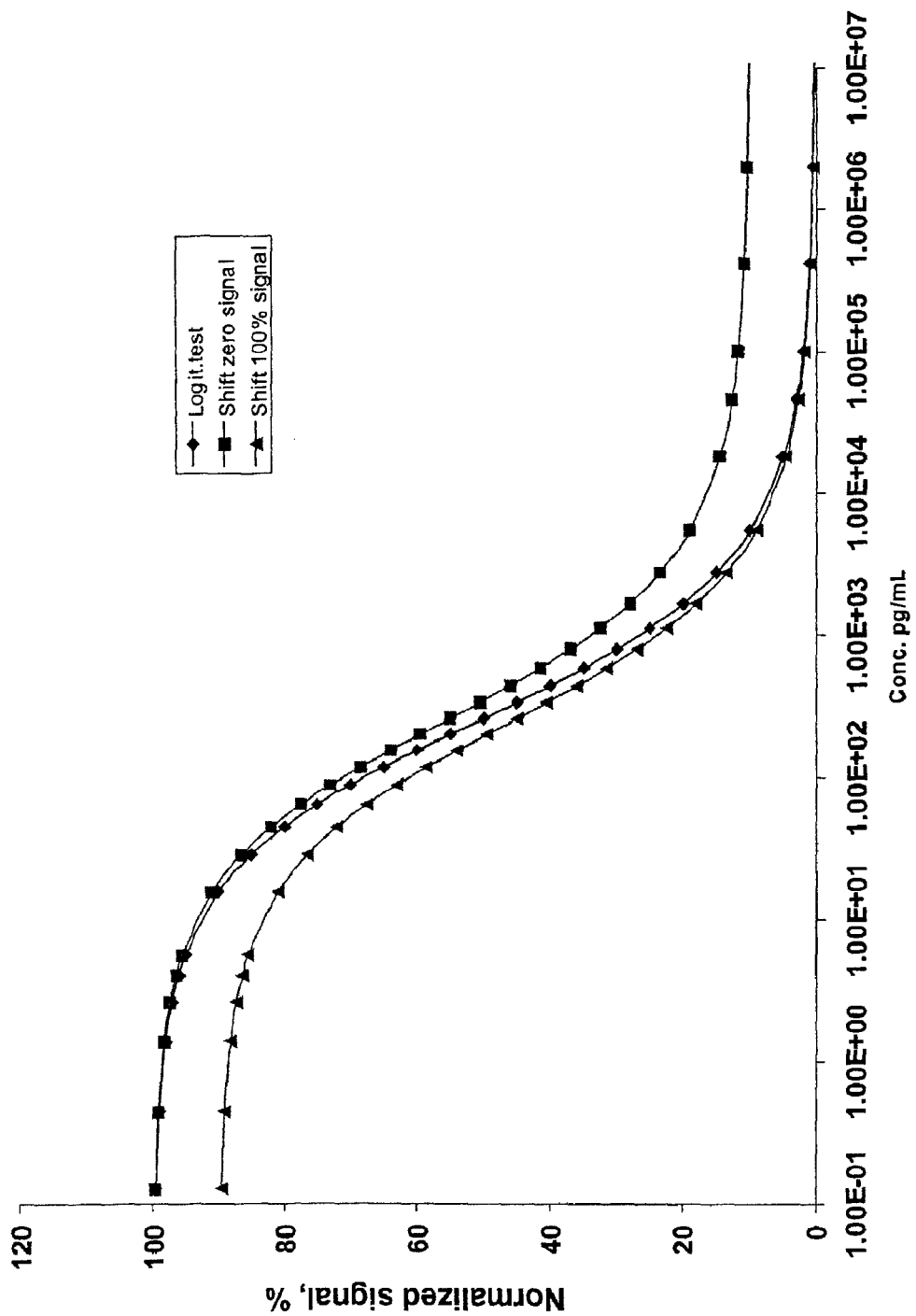
FIG. 22 shows dose responses computed with and without errors in calibration parameters.
Figure 23:
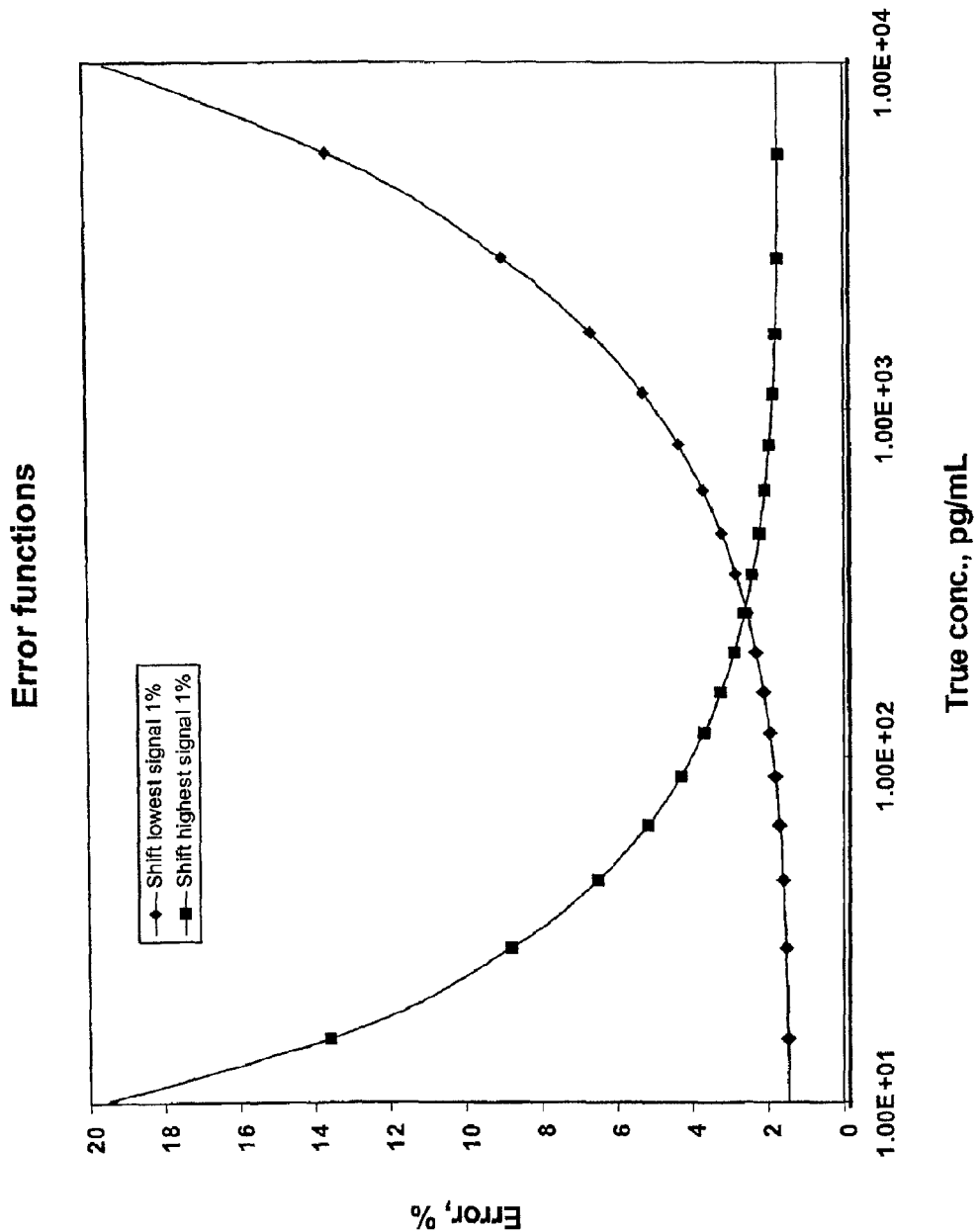
FIG. 23 shows computed concentration errors produced by 1% mis-estimation of A and D calibration values.

The magnitudes of these calibration errors and consequently errors introduced in estimating analyte concentrations can be quite significant. FIG. 21 shows the dose-response data for a two-step assay for Thromboxane. The top curve (Logit.test) in FIG. 22 shows a typical (ln-logit) assay response. When we adjust the level of the highest signal (A) and the lowest signal (D), shown as "Shift zero signal" and "Shift 100% signal", respectively, the curves shift as seen in FIG. 22. The corresponding computed values of error in the concentration that would be calculated from Equation 2 were large (>20% across the entire range of the assay) as shown in FIG. 23. In FIG. 22, the signal is normalized by subtracting the D value from the signal and dividing the difference by (A−D):(Signal−D)/(A−D). This yields what is usually described as $B/B_0$ (the ratio of bound label at a given analyte concentration to that at zero analyte level). The ln-logit function was modified by adding 10% of (A−D) to D or subtracting 10% of (A−D) from A before recalculating the normalized signals (corresponding to two types of significant calibration error (shifting the value of A or D respectively). At signal levels intermediate between A and D the change made was adjusted by 10%*(Original signal−D)/(A−D). FIG. 23 shows that when modifications of only 1%*(A−D) were made, and concentration of the analyte was computed, errors in concentration were still significant at certain parts of the analyte concentration range.

In a laboratory setting, errors in measuring biochemical parameters of blood and other bodily fluids due to calibration errors are dealt with using many known compensation mechanisms. One of the simplest techniques is to add a known quantity of a trace amount of a radiolabeled analyte and construct a calibration curve based on those readings.

Other methods include adding a known amount of a standard to the analyte solution that needs to be analyzed. However, such techniques are impractical in a disposable, handheld system for analysis, without particular adaptation of those techniques for dealing with small sample volumes, lack of large amounts of other solutions (such as buffers), and ability to exercise precise controls over the volumes of the samples and their dilutions.

Conventionally, a calibration exercise is performed in parallel with assaying the sample. This is, however, impractical in a self-contained, disposable assay system intended to be compact and inexpensive. To address any calibration challenges that may occur while assaying analytes using a fluidic device of the present invention, in some embodiments parameters A, or in preferred embodiments A and D, of Equation 1 described herein above, are measured within the fluidic device rather than using manufacturer's values or an external device. The value(s) is compared with the parameter values estimated when the fluidic device was calibrated by the manufacturer. Signal results are then adjusted using the following equation: $Signal_{adjusted} = Signal*(A_{factory\ calibration}/A_{measured\ within\ the\ assay})$ and the original calibration equation (Equation 1) is then used to calculate the analyte concentration. Alternatively, A and D values measured at the time of assay are substituted for the A and D values obtained during factory calibration. Typically the (A/D) calibration measurement would be made in a buffer sample, preferably for each analyte (in a multiple analyte assay device), or one analyte only, if each assay responds similarly to the various factors that alter the calibration parameters.

In some embodiments of this invention, the calibration parameters of Equation 1 are corrected using differential calibration. The following example using Thromboxane B2 as the analyte illustrates this approach. Thromboxane B2 (TxB2) (1.25 mg) was dissolved in a mixture of dimethylsulfoxide (342 µl) and water (342 µl). To this, 5 µl of a solution of 1-(3-(dimethylamino)propyl)-3-ethyl-carbodiimide hydrochloride in water (0.1 g/ml) and 10 µl of a solution of n-hydroxy-succinimide in water (0.1 g/ml) were added. After 1 hour at room temperature the resulting NHS-ester of TxB2 was used in the preparation of TxB2 labeled with alkaline phosphatase (described below) without further purification. Alkaline phosphatase (bovine intestine, Sigma-Aldrich) was dissolved in phosphate-buffered saline at 1 mg/ml. To 1 ml of this solution 120 µl of the NHS-ester of TxB2 was added and the mixture allowed to react for 1 hour at room temperature. The enzyme-TxB2 conjugate was then purified overnight by dialysis against tris-buffered saline containing $MgCl_2$.

Described is an example of a two-step enzyme immunoassay where TxB2 is the analyte. Samples and mouse monoclonal anti-TxB2 (15 µl of Cayman Chemical Kit Catalog number 10005065, appropriately diluted into Assay Designs buffer) were added to 384-well plates to which anti-Mouse IgG had been immobilized ((Becton Dickenson 356177)). The sample was 30 µl of plasma diluted 1:4 with assay buffer (Assay Designs Correlate-CLIA™ kit 910-002) and supplemented with known concentrations of TxB2. Other types of sample (for example TxB2 dissolved in assay buffer) can be substituted.

Plates were covered to prevent evaporation and incubated at room temperature with gentle mixing (100 rpm) on an orbital shaker for 12 hours. The contents of the wells were then removed by aspiration. Thromboxane-labeled with alkaline phosphatase (25 µl diluted 1:1500 with assay buffer) was added and incubated at room temperature for 2 minutes. The contents of the wells were removed by aspiration and wells washed thrice with 100 µl wash buffer (from the Assay Designs Kit 910-002).

Enzyme bound to the wells was then measured by addition of 40 µl Lumiphos™ 530 substrate solution which contains (4-methoxy-4-(3-phosphate-phenyl-spiro-[1,2-dioxetane-3, 2'-adamantane])). Incubation was allowed to proceed for 1 hour with orbital mixing and the luminescent product measured in a Molecular Devices MD5 Spectrometer (0.5 second integration time).

FIG. 21 shows the typical assay dose-response data for a two-step assay for TxB2. Using Equation 1, the parameters A, B, C and D are fitted to the curve shown in FIG. 21. As described herein, even small changes in values of the parameters A and D can have a significant impact on the measured concentration. Thus, any errors in computing A and D are magnified in the estimated analyte (TxB2) concentration. This concept is illustrated in FIGS. 22 and 23, where even a 1% change in (A–D) resulted in significant errors in estimating TxB2 concentrations in the samples. In FIG. 22, the signal is normalized by subtracting the D value and dividing the difference by (A–D) viz: (Signal–D)/(A–D). This calculates what is commonly described as B/B0 (the ratio of bound label at a given analyte concentration to that at zero analyte level). The (ln-logit) function was modified by adding 10% of (A–D) to D or subtracting 10% of (A–D) from A before recalculating the normalized signals (corresponding to two types of significant calibration error (shifting the value of A or D respectively). At signal levels intermediate between A and D, the change made was adjusted by 10%*(Original signal–D)/(A–D). FIG. 23 shows the computed errors in estimating the analyte concentrations for a 1% error in estimating A and D. As can be seen for the low analyte concentrations, the errors are pronounced even for small errors in the calibration parameters A and D.

Figure 24:
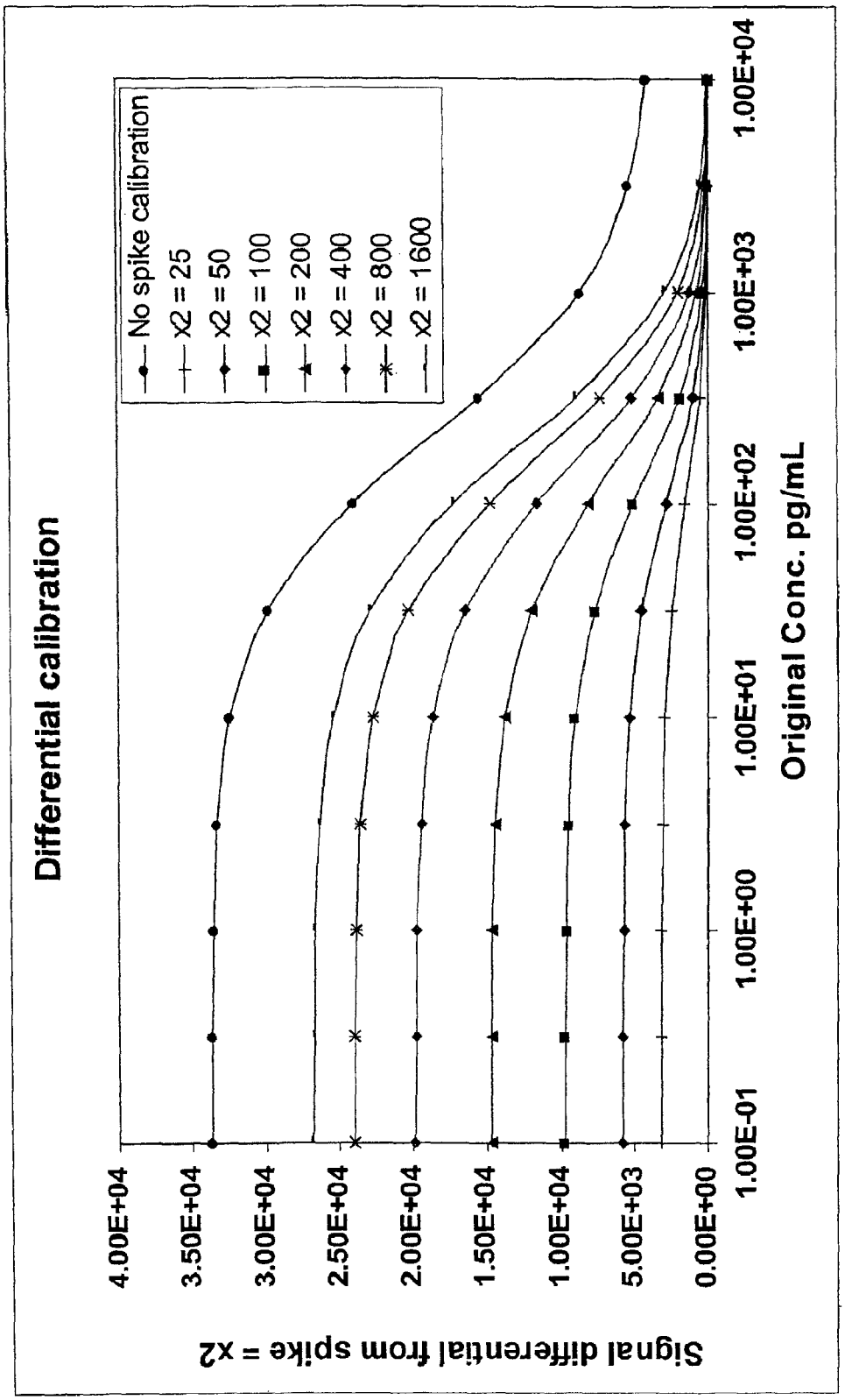
FIG. 24 illustrates calibration using a "differential" approach.

FIGS. 24-27 illustrate an embodiment of this invention where the sample containing an unknown analyte concentration is spiked with a known concentration of the analyte to minimize calibration errors. Spiking can be achieved by a variety of methods, for example, by incorporating analyte in known quantities to the assay well during manufacture of the fluidic device. Separate spike wells could also be accommodated in the fluidic device described herein. FIG. 24 shows calibration using differences between signal response between unspiked and spiked samples. The amount of the spiked analyte is indicated by x2 and the original (endogenous concentration in the sample) is denoted as original concentration or x1 (pg/ml). The difference in signal between unspiked and spiked sample is plotted against the signal for the original concentration for various amounts of known amount of analyte (spike) introduced into the sample. The (ln-logit) parameters (for the top curve in FIG. 24) are shown in Table 1.

TABLE 1

| Original Calibration Parameters for Data Shown in FIG. 24 | |
|---|---|
| A | 3.37E+04 |
| B | 1.01E+00 |
| C | 2.10E+02 |
| D | 3.56E+03 |

The data shown in the top curve in FIG. 24 were used in a recalibration exercise by calibrating against the difference in signal for each original concentration level and each level spiked with 200 pg/ml analyte. Equation 3 shown below was empirically derived and is useful in calculating the original endogenous concentration of analyte. The best-fit parameter values in Table 2 were computed by minimization of the sum of the square of the differences between target and calculated analyte values. Concentration=$C*((A-D)/((Signal-D)^{(1/B)})+E$ [Equation 3].

TABLE 2

Calculated Parameter Values for 1-point Spike Calibration

| | |
|---|---|
| A | 1.20E+02 |
| B | 1.996189 |
| C | 292.7824 |
| D | −0.14393 |
| E | −287.931 |

Figure 25:
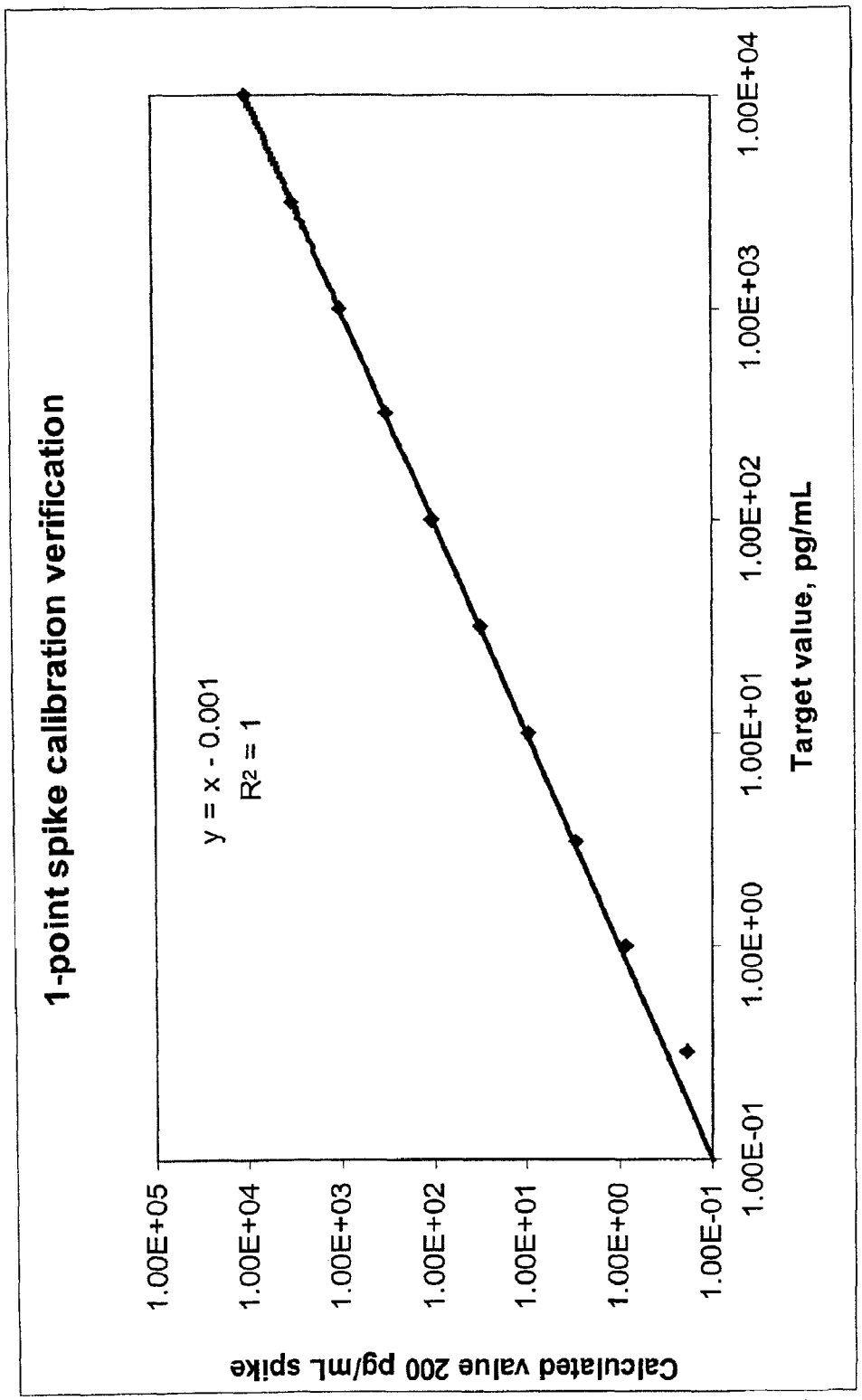
FIG. 25 shows the verification of calibration using the "1-point spike" method (log scale).
Figure 26:
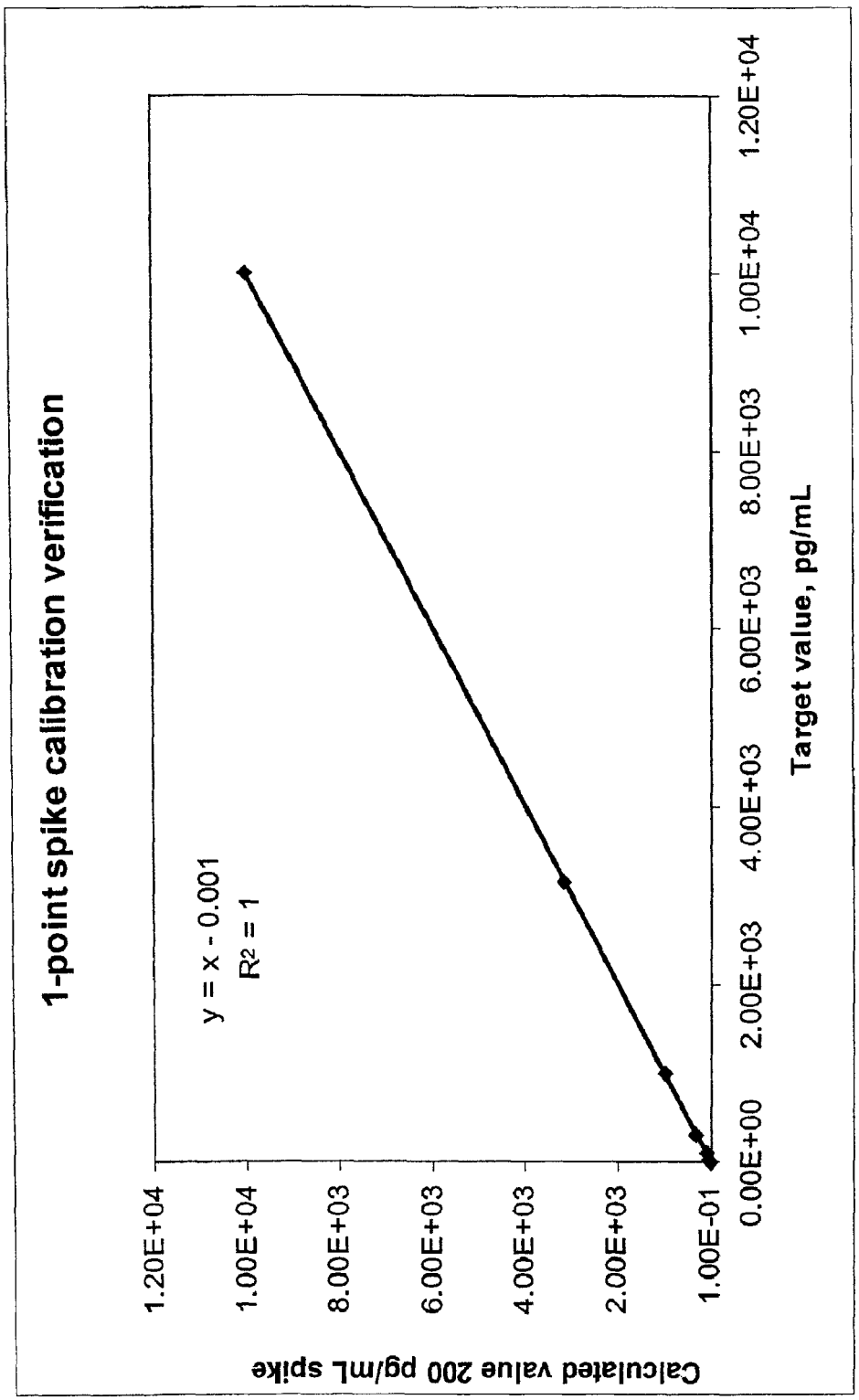
FIG. 26 shows the verification of calibration using the "1-point spike" method (linear scale).

This calibration was verified as shown in FIG. 25 (log scale) and FIG. 26 (linear scale). Note the regression equation was calculated for data in linear form. The formula resulted in near perfect results.

Figure 27:
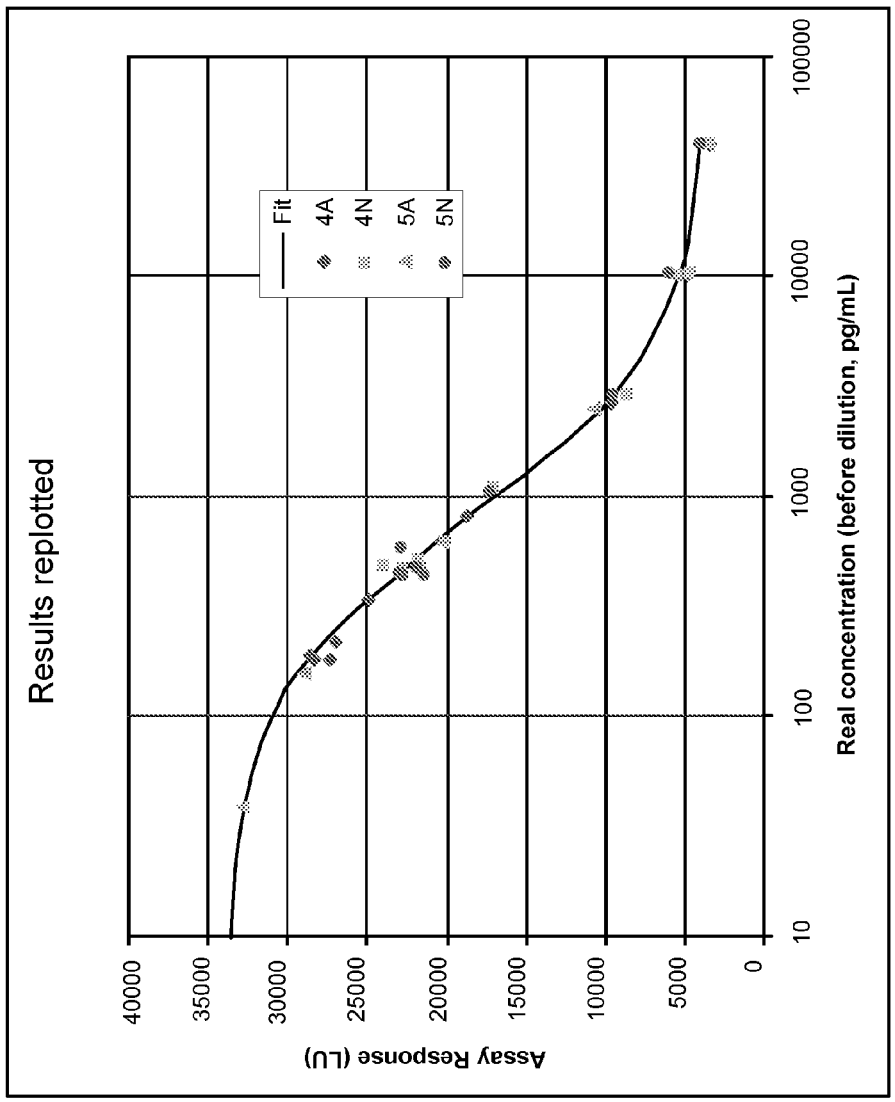
FIG. 27 shows dose-response of assays calibrated against a plasma sample with a very low TxB2 concentration.

The results of one embodiment of this invention are shown in FIG. 27, where the extent of the recovery of the spike signal is used to correct for the concentration of the value of the unspiked sample. This method has the advantage that changes in the parameter C in the (ln-logit) equation due to, for example, reagent instability, are accounted for. The method involves the following steps: calculate x1 (endogenous conc.), and x2 (spike conc.) using original calibration; calculate recovery of spike as % (x2−x1)/spike [Equation 4]; correct x1 by recovery factor: (x1*100/Spike recovery) [Equation 5].

Figure 28:
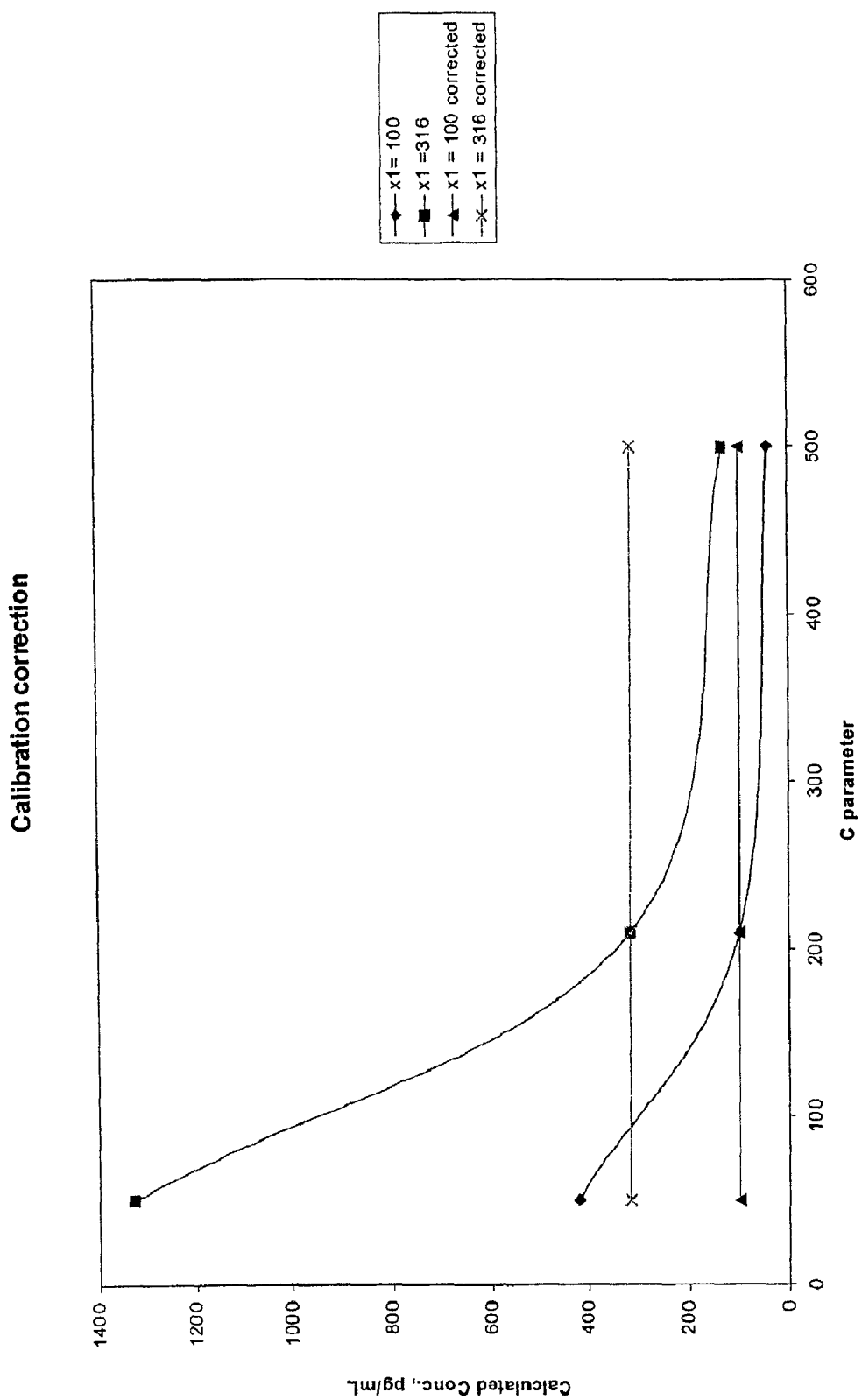
FIG. 28 shows use of spike recovery to eliminate calibration errors of the "C" parameter.

This was tested with the calibration curve shown in FIG. 24 and the original calibration parameters of Table 1. As shown in Table 3, it was possible to use spike concentration values from 100-500 pg/ml and C values that varied from 500 to 50 such that the actual signals corresponding to the modified C values were changed very significantly from what had been the case with the original C value and the spike recovery (calculated with the original C value ranged from 42-420% respectively, yet the recovery of the unspiked sample (once corrected for the recovery of the spike) was 100% over the entire calibration range. This effect is graphically illustrated in FIG. 28, where the C parameter is varied between 50 and 500 (a ten fold range), but the corrected values for the analyte concentration (x1) accurately reflects the expected analtye concentration.

TABLE 3

Effects of changes in the C parameter on spike and original analyte recovery at two original concentration levels:

| C | x1 Pg/ml | S (x1) | x2 pg/ml | S (x1 + x2) | x2 recovery % | x1 recovery % |
|---|---|---|---|---|---|---|
| 500 | 100 | 2.88E+04 | 500 | 1.73E+06 | 42 | 100 |
| 210 | 100 | 2.40E+04 | 500 | 1.13E+04 | 100 | 100 |
| 50 | 100 | 1.36E+04 | 500 | 5.83E+03 | 420 | 100 |
| 500 | 316 | 2.21E+04 | 500 | 1.50E+04 | 42 | 100 |
| 210 | 316 | 1.56E+04 | 500 | 9.66E+03 | 100 | 100 |
| 50 | 316 | 7.61E+03 | 500 | 5.25E+03 | 420 | 100 |
| 500 | 100 | 2.88E+04 | 200 | 2.25E+04 | 42 | 100 |
| 210 | 100 | 2.40E+04 | 200 | 1.60E+04 | 100 | 100 |
| 50 | 100 | 1.36E+04 | 200 | 7.80E+03 | 420 | 100 |
| 500 | 316 | 2.21E+04 | 200 | 1.84E+04 | 42 | 100 |
| 210 | 316 | 1.56E+04 | 200 | 1.22E+04 | 100 | 100 |
| 50 | 316 | 7.61E+03 | 200 | 6.16E+03 | 420 | 100 |

In Table 3, X1 is the endogenous concentration and x2 is the spike concentration; S is the signal level corresponding to the designated analyte concentration; x2 recovery is the apparent recovery of x2 and x1 recovery is calculated (using Equation 5) after compensating for x2 recovery (using Equation 4).

The spike level must be carefully chosen. The optimal level will be a compromise between the operating range of the assay and the likely range of concentrations of samples. If it is too low, the change in signal caused by the spike will be too small to be reliably measured. If it is too high, the assay response will be too shallow to reliably measure the spike. The ideal spike level would change the measured signal by much more than the standard deviation in the signal. In the above example, the assay range had been adjusted to make measurements for sample with concentrations in the range of about 0 to about 500 pg/ml and spikes of about 200 to about 1000 pg/ml would likely be useful.

In some embodiments the following various guidelines for choosing spike levels can be followed: spikes should change the observed signal across the desired range by at least 10%; spikes should be in the same range as the anticipated mid range of sample concentrations; spikes should be less than about three times the original C value. Note that the useful part of the dose-response is from about 0.2*C to about 5*C.

The following example illustrates the estimation of endogenous TxB2 concentrations using spike recovery. Two citrated human plasma samples were analyzed by the two-step assay. Aliquots of the samples were also supplemented (spiked) with known concentrations of TxB2 prior to assay. Some samples were also supplemented with indomethacin (0.1 mM) and/or EDTA (5 mM). Samples were stored either flash-frozen then thawed or refrigerated unfrozen prior to assay. These procedures generated a set of samples with various original endogenous concentrations (storage and freezing and thawing tends to cause platelet activation and production of TxB2; indomethacin inhibits TxB2 production).

The results of the above experiment are shown in FIG. 27. Sample 5A was known to have a very low TxB2 concentration (estimated to be <10 pg/ml). When the dose-response of the assay in sample 5 was used to calibrate the assay, the concentration was assumed to be zero. Dose responses for the other samples 4A, 4N, 5N were then plotted and it was observed that their response corresponded to higher concentrations of TxB2 and could be fitted to the 5N response by moving each to the left (in the direction of lower concentration) by an amount corresponding to removing a certain fixed TxB2 concentration from each the known spike levels. All the samples had responses that were almost identical in shape to that of sample 5N. When the curves fitted as closely as possibly to the A5 curve, the concentration of TxB2 notionally removed corresponds to the estimate of the TxB2 concentration in the sample.

Figure 29:
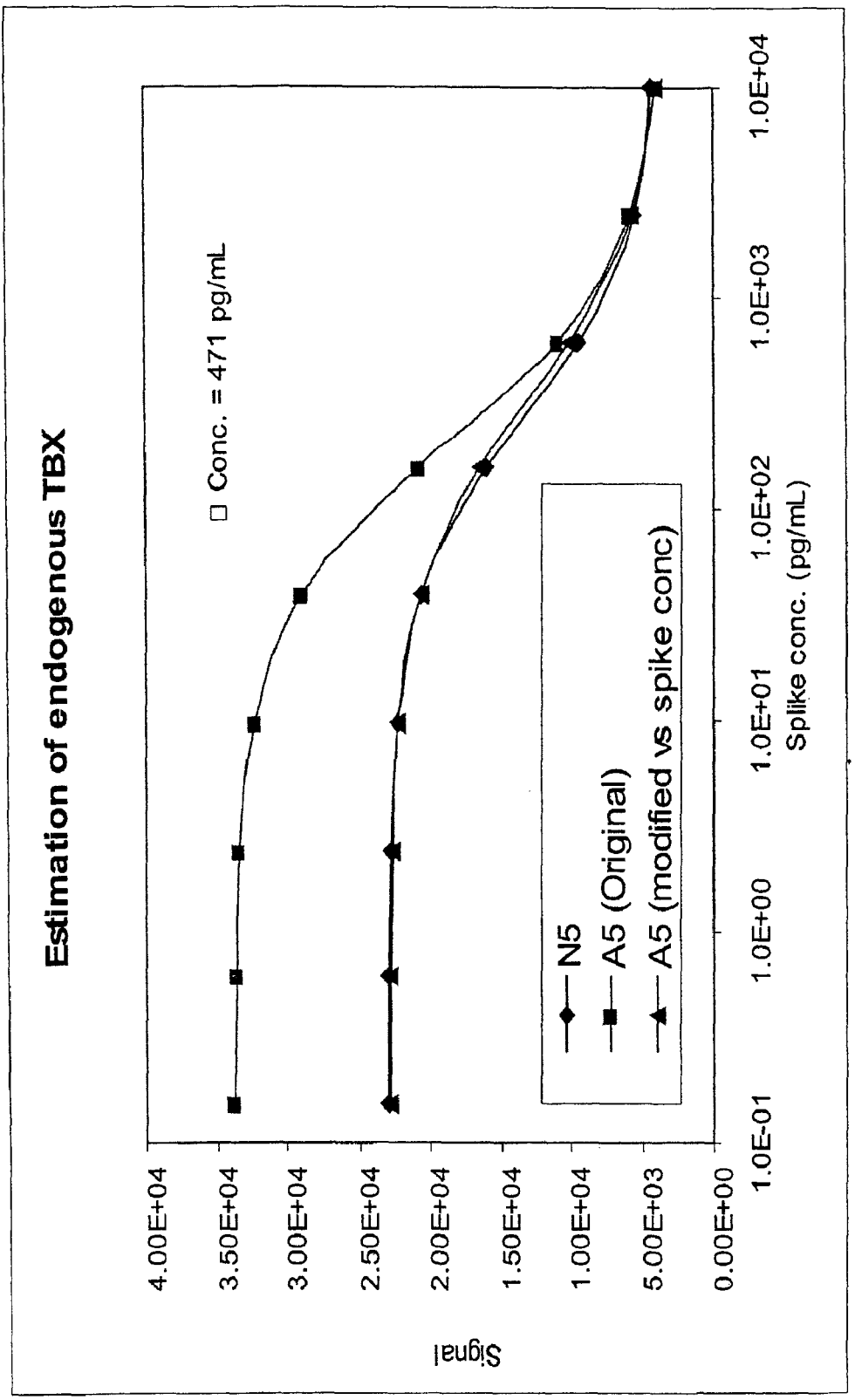
FIG. 29 illustrates calculating differences in concentration between two samples.

The original data of FIG. 27 were represented in FIG. 29 by the best fit (ln-logit) approximation. The Solver function in Microsoft Excel was used to compute a value of TxB2 that caused the A5 response to approximate that of the sample N5. As can be seen, this generated a good fit and the computed value (471 pg/ml) is an estimate of the concentration difference between TxB2 levels in the two samples.

Figure 30:
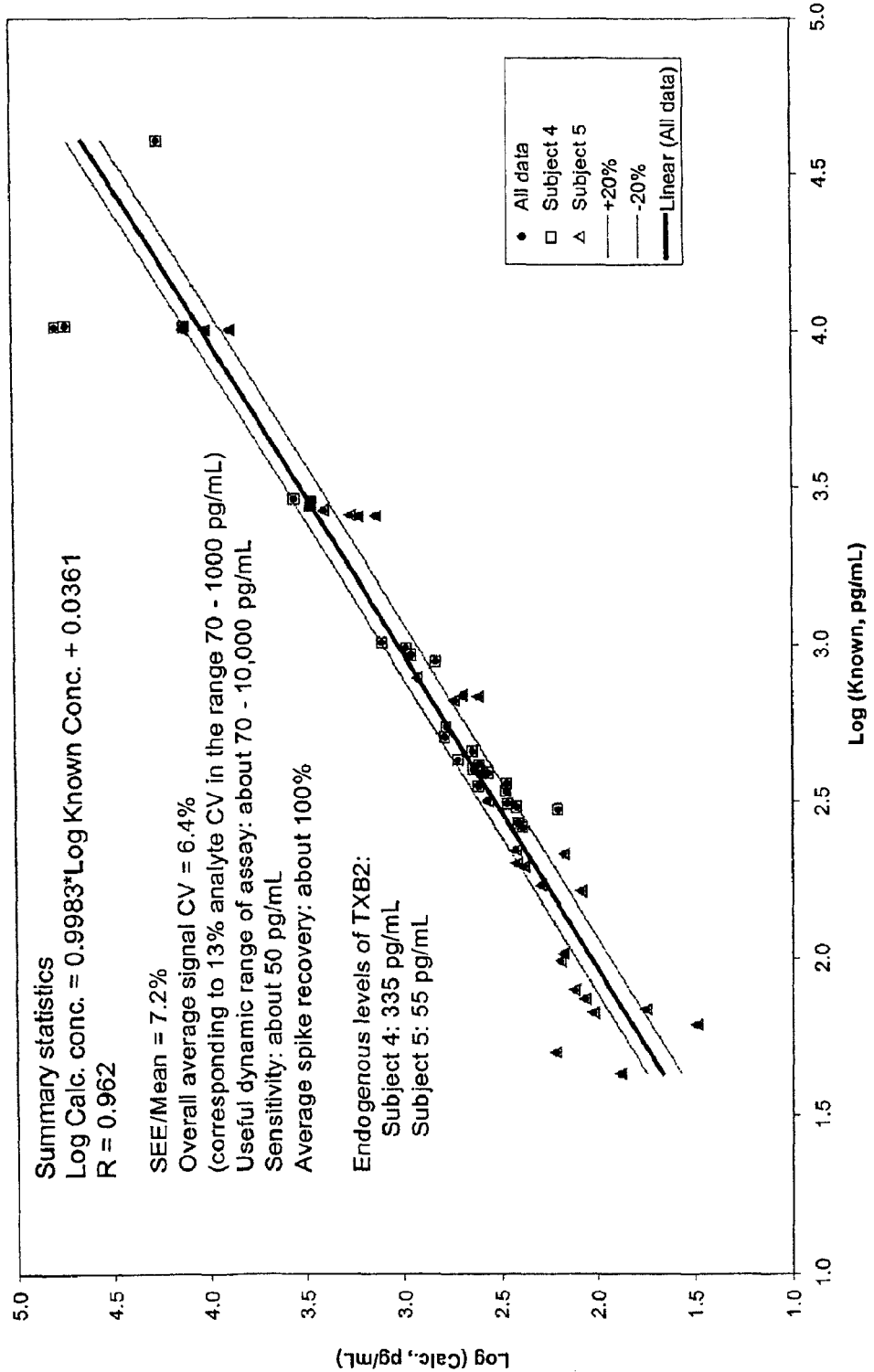
FIG. 30 illustrates an assay of plasma samples.

In another embodiment of our invention a single point can could be used (all the points fit closely to the calibration curve, so any single point could have been used) rather than a multi point spike that was illustrated in the earlier FIGS. 24-27. The following experiment illustrates this concept. Two plasma samples were spiked to many levels of TxB2 and assayed by the two-step method. Assays were calibrated using buffer calibrators rather than plasma-based materials. Results are presented in FIG. 30. Plasma was analyzed as described earlier. Data in FIG. 30 are plotted on a log scale.

The concentration of unspiked samples was calculated from the calibration and the concentration of spiked samples taken as "endogenous+spike." Results are plotted only for the spiked samples. As can be seen, there was desirable correlation between the calculated and known values over the range of about 50 to about 10,000 pg/ml. When recovery was estimated for spikes in the range about 40 to about 2,500 pg/ml, the correlation was 99.7%.

Spike recovery method for correcting the calibration parameters are useful for compensating temperature effects on immunoassays in self-contained disposable analytical systems, also some times referred to as handheld analytical systems or assay systems. As is well known, instabilities in temperature during an assay introduce significant errors in the estimated analyte concentration. Temperature effects on calibration of immunoassays have the strongest impact on the A, C and D parameters of the (ln-logit) calibration. It is likely that the B (shape) parameter is minimally affected by temperature changes. As shown above, the spike recovery method can correct for errors introduced in the C parameter and hence could be an excellent approach for correcting temperature induced errors in computing the calibration parameters of the (ln-logit) equation. Similarly, normalizing signal levels to the zero analyte calibrator level, as described earlier, can compensate for errors in the A and D parameters, which are again negatively influenced by temperature changes.

Internal calibration and/or spike recovery means of calibration have significant advantages over conventional factory-calibration methods. One obvious advantage is that two quantities of assay-related information are used to compute the assay result rather than one, which improves the reliability of the assay. A second advantage is that this approach compensates, to a large extent, reagent instability. Another advantage is that several instrument, assay environment, and procedural variables are factored into the assay results.

Figure 31:
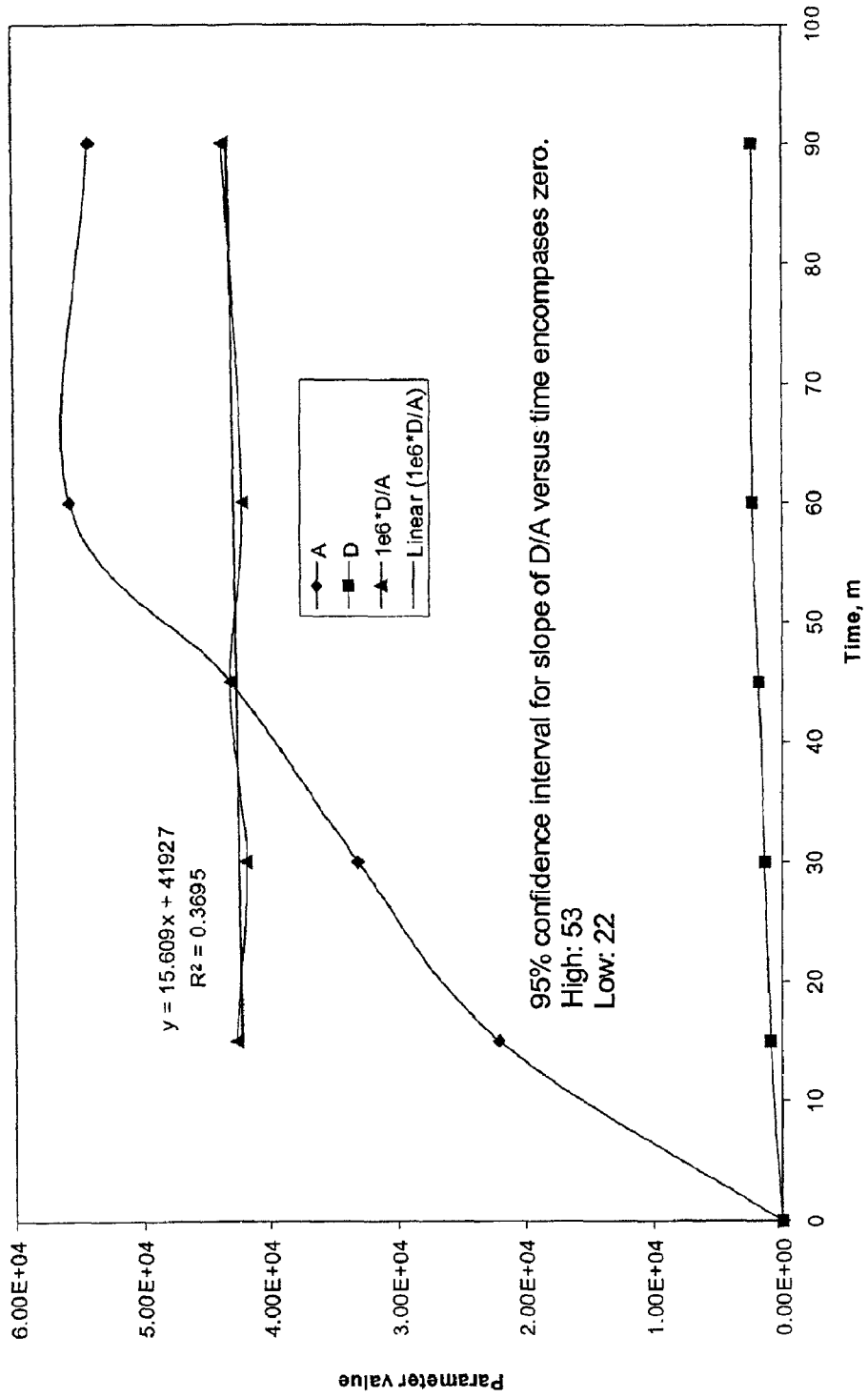
FIG. 31 shows the time course of assay signal generation.

Other uncontrolled changes in system response, besides temperate change, can also negatively impact the computed A and D parameters. For example, FIG. 31 shows the time course of the signal generation during an assay. To correct for these errors, one embodiment of the claimed invention is to compare assay signals B in a fluidic device with the B0 signal so to eliminate errors due to variation of the absolute value of assay signals due to uncontrolled changes in system response. This concept was verified by the following experiment.

A competitive immunoassay for TxB2 was set up using the protocol described in Assay Designs Product Literature for their corresponding Correlate-CLEIA kit (catalog 910-002). An alkaline phosphatase conjugate was prepared as described earlier and was diluted 1:112,000 and substituted for the kit conjugate. A and D parameters are the calibration parameters used in the (log-logit) fit to the assay response. Best fit values were obtained at each time point. Note that at zero time the A and D parameters are not measured, but all signal values would be (are known to be) zero. The ratio D/A was multiplied by 1e6 so as to be presentable on the same scale. The A and D values when plotted against time vary significantly, particularly the A value (zero analyte). As seen from the straight line with practically zero slope, the scaled D/A remains constant over the time span.

Figure 32:
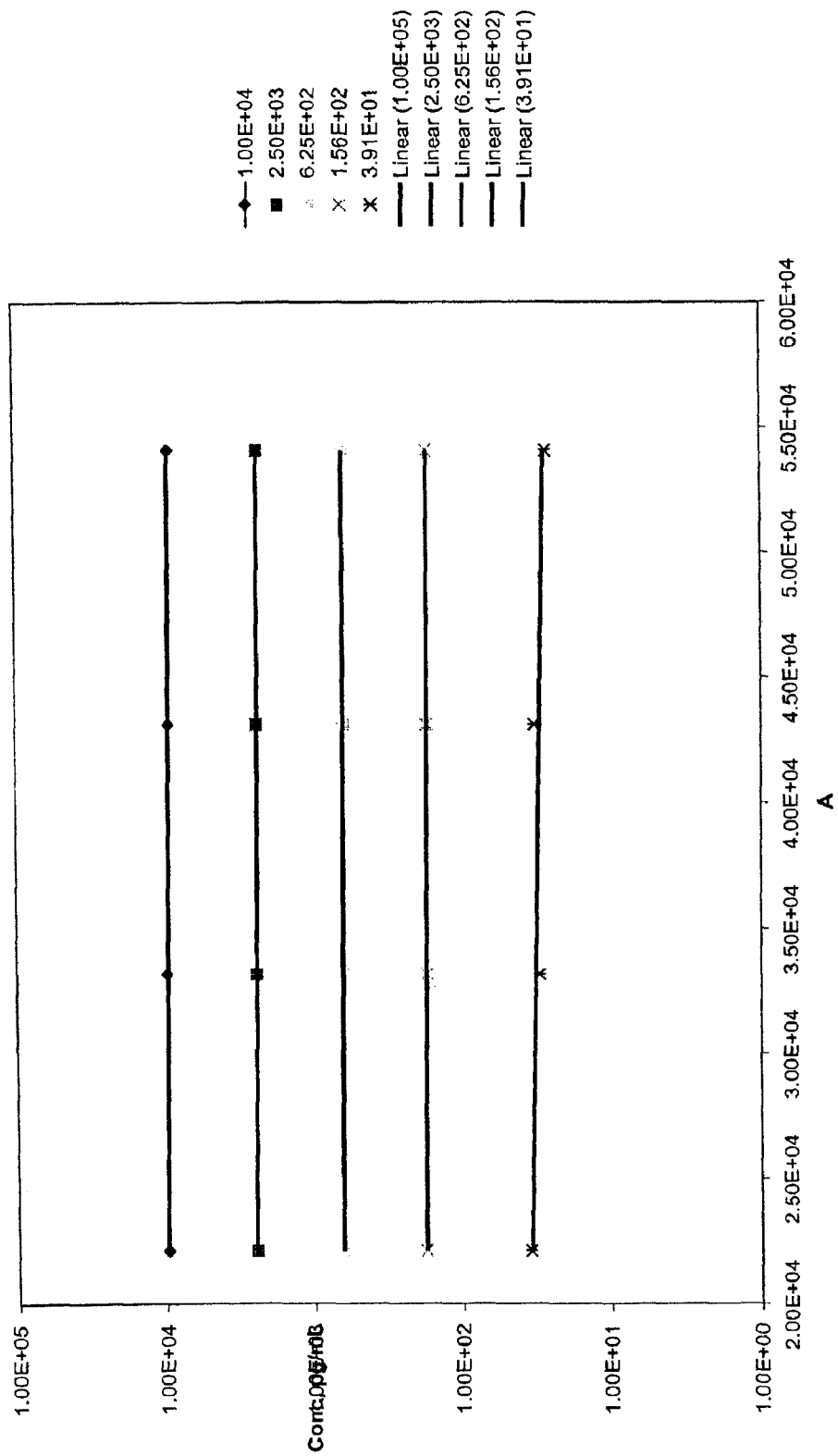
FIG. 32 shows the impact of change in calibration parameter "A" on assay calibration.

The above experimental data were then analyzed by normalizing the assay signal (B) to signal at zero analyte concentration (B0). Using this normalized signal (B/B0), (log-logit) best fits were obtained for each time point and averaged. Concentrations of analyte were computed using these calibration parameters for each time. FIG. 32 shows the derived concentrations that were plotted against the A parameter derived for each individual time point. Each line corresponds to different analyte levels (pg/ml) ranging from about 39 to about 10,000 pg/ml. As can be seen from FIG. 32, although signal values changed by about 2-fold during the course of the experiment, the derived analyte concentration was essentially constant over the analyte concentration spanning a range of about 39 to about 10,000 pg/ml. The variation of calculated concentration was computed and found to average only 2.7% over the calibration range of 39-625 pg/ml (which spans most of the range).

A calibration spike can be enabled by adding analyte to the antibody (or other solid phase capture agent) during manufacturing, and then drying, subsequently adding analyte to the appropriate well during manufacturing (then drying), or adding analyte to a portion of assay buffer which is then routed to the appropriate well. Methods 1 and 2 have a risk which is that the spiked analyte could be flushed from the well as sample or buffer enters. This may be handled in one of several ways such as relying on the tightness of the antigen: antibody interaction for the brief time the well is subject to flowing sample or buffer (which exit from the well), or careful management of liquid flow and placing the spike well as that most distal to the incoming liquid (last well to fill has the least flow through).

Errors in measuring analyte concentrations could also be due to variability in the pre-analysis phase. The primary cause of this type of errors is due to the patient collecting an incorrect volume of sample or where the sample integrity has been compromised. Errors due to incorrect sampling volume can by corrected by a variety of means. One method is to measure the volume of the sample during a pre-processing step. If the measured volume is significantly different from the expected volume, the patient could be instructed to provide a new sample. This could be accomplished by, for example, the wireless communication with the external device as described herein. Alternatively, the analytical methods or algorithms on the external device could be recalibrated to compensate for the change in the sample volume. The recalibration could be using any of the standard calibration techniques or the modifications to the calibration process, which have been described herein.

The following is a description of one embodiment of a method for determining the accuracy of the volume of the sample provided to the sample collection unit of a fluidic device described herein. The sample collection unit can be lined with conductive elements spaced apart at known separations similar to the graduations on a measuring cylinder or jar. The location of each conductor can correspond to a specific sample volume. As fluid comes into contact with the conductor, the measured conductivity of that conductor would be markedly increased. By identifying the highest placed conductor that has undergone the conductivity change, the volume of the sample in the sample collection unit can be computed.

Alternatively, if the sample volume has to meet a minimum, a conductive element could be placed at the appropriate level in the well. When the cassette is introduced into the handheld (or the sample holder is introduced in the analytical system), thereby the patient has indicated that she has completed the sampling process, and if the conductivity of the sensor remains at the baseline level, it could be easily concluded that the patient has not provided the required sample volume. The patient could be given the appropriate feedback such as replacing the sample or replenishing it. Alternatively, the back-end server or computer at the network headquarters could be informed of the issue and appropriate corrective measures taken. An alternative to the electrical sensing for the correct volume could be using known optical sensing means.

Sample integrity could be affected by many factors, some intrinsic to the patient and some that are extrinsic. Following are some of the sources of errors in sample integrity: (i) mixing of interstitial fluid with blood; (ii) variability in the hematocrit concentration; (iii) hemolysis; and (iv) activation of platelets and sample clotting.

Occasionally, interstitial fluid may leak from a finger-puncture wound and could mix with blood. Alternatively, if the patient had liquid on her hands due to washing prior to obtaining a blood sample, such liquid could also mix with blood plasma. Both fluids mentioned, above, interstitial fluid and wash liquid, contain no red cells and would mix with the blood plasma. When the amount of interstitial fluid is large so that the effective hematocrit is very low, the measured concentration of the external standard (fluorescein) would be low. This signal could be used to conclude that the sample is inappropriate for analysis and that it could lead to incorrect results. When blood is contaminated by water (which has low conductivity), it would be possible to detect this by measuring the conductivity of the fluid part of the sample (blood plasma has a characteristic high conductivity not subject to variation from day-to-day or individual-to-individual). If the measured conductivity of the sample is lower than the plasma conductivity, it is likely that the sample has been contaminated.

Errors could also be due to incorrect operation of the instrument and means of detecting and compensating those errors are described below. One source of error could be that the disposable is not properly accommodated in the handheld system. Having a sensor detect and report the proper mating of the disposable in the handheld would be one means of avoiding this problem. Another source of errors is from the fluidic system, where there may be an issue with where the sample is applied in the sample well and the volume of the applied sample. This could again be addressed by the use of appropriate sensors which detect the application of a sample and report on the adequacy of the volume that is applied. Other fluidics related problems could be blocked channels, insufficient reagents, bubbles, etc., all of which again could be detected and reported by the use of appropriate sensors.

In some embodiments any of the errors described herein can be measured using sensors located on either the fluidic device or the reader assembly. In some embodiments an error messages could be displayed on an LCD screen in the reader assembly using the processing power of the microchip on the handheld. Alternatively, a signal from the sensors could be communicated to the external device which can then relay an error message to either the reader assembly or a third device such as a PDA or cell phone. Such action could be a message communicated to the patient in the form of an audio, video or simple text message that the patient could receive. In some embodiments the external server can transmit corrected calibration parameters to the reader assembly to compensate for any of the errors described herein.

In yet another embodiment, after the identifier is detected by an identifier detector as described herein to determine, for example, a protocol, if a signal transmitted by a sensor doesn't match the expected value for the sensor signal, then the external device can transmit a pre-programmed alert based on each cartridge bar code and sensed signal to either, for example, an LCD display on the reader assembly or to a handheld device, to take a designated action. Nonlimiting examples of error alerts, the problems they indicate, and required action to be taken are, for example:

| Error Code | Symbol | Problem | Action |
|---|---|---|---|
| Er1 | Thermometer | Temperature out of range | Wait until Temp >10 or <35 C. |
| Er2 | Blood drop | Blood sample too small | If detected w/in 15 minutes of first sample add more blood, other wise use new cartridge |
| Er3 | Battery | Power disruption | Do not start test until power resumes |
| Er4 | Bar code symbol | Cartridge expired | Run test on a non expired cartridge |
| Er5 | Line through fluidic device | Cartridge already used | Run test on a new cartridge |
| Er6 | Phone receiver | No Cell Phone coverage | Do not start test until in coverage area |
| Er7 | Line through a box | Reader malfunction | Call Theranos |
| Er8 | Bottle with a "C" in the label | Calibration overdue | Run Calibration standard, then run test |

After the identifier detector detects the identifier to determine a protocol and any sensed signals are detected and either patient notification is complete or calibration parameter are updated, the fluidic device calibration can occur, followed by the appropriate assay.

Despite the corrective actions described here, the generated analyte concentrations values could still be erroneous. For example, the actual analyte concentration could be well outside the expected range, and thus the calibration parameters used may be incorrect. Values which are unlikely, impossible or inconsistent with prior data for a particularly patient could be flagged and subjected to a software review. Values with suspect accuracy can be communicated to the appropriate decision maker, such as the patient's physician.

Figure 34:
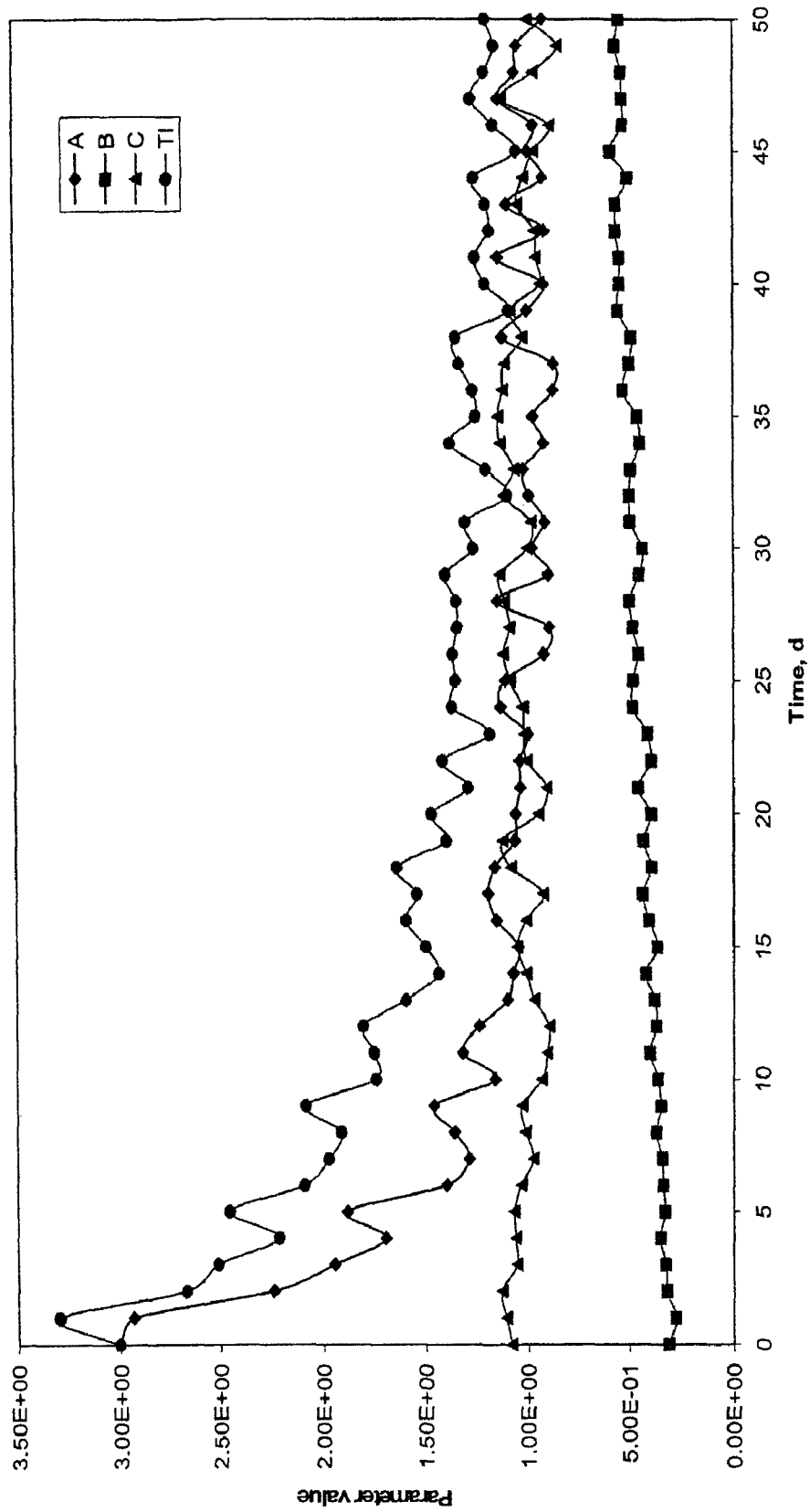
FIG. 34 illustrates computing the therapeutic index.

The concept of the reference therapeutic index (TI) and how it is computed is illustrated in FIGS. 33 and 34. A TI is computed from a retrospective analysis of many measured parameters, including the blood concentrations of drugs of interest, their metabolites, other analytes and biomarkers in blood that change concentrations due to the drugs the patient is consuming, physiologic parameters (such as blood pressure, respiratory rate, body temperature, heart rate, etc.), and clinical parameters that indicate disease progression (such as angina, stroke, infarct, etc.). Typically, many serial measurements would be made for the many treated patient and corresponding controls (unmedicated or placebo treated). The clinical parameter would be an "outcome parameter" (OP). The other measured parameters can be "input parameters" (IP).

For the retrospective analysis and TI computation, data from many subjects and their respective output and input parameters, including subject's relevant details such as height, weight, race, sex, family history, etc., would be populated in a database. Each candidate outcome parameter (stroke, infarct, angina, death, etc.) will be subject to multiple regression analysis against input parameters.

The multiple regression analysis is performed for each candidate OP versus all available IPs. Database columns are constructed by using each IP, each IP^2, and all cross-terms (IPi*IPj). The analysis is then performed using the equation:

$$OPi=(a*IP1+b*IP2+\ldots n*IPn)+(aa*IP1^2+bb*IP2^2+\ldots +nn*IPn^2)+(aaa*IP1*IP2+bbb*IP1*IP3+\ldots +nnn*IPn-1*IPn),$$

where $a \ldots n$, $aa \ldots nn$, $aaa \ldots nnn$ are arbitrary constants.

Multiple regression analysis establishes the best fit to the equation and indicates which IPs are strong candidates for inclusion. Weakly correlated IPs are dropped and the analysis repeated until each candidate OP has an optimal relation to the remaining IPs. The therapeutic index will then have the form:

$$TI=a*IP+cc*IP3^2+nnn*IP3*IP5+ \quad \text{(Equation 6)}.$$

FIG. 34 illustrates the computation of a TI and the use of the TI concept for determining therapeutic efficacy (the therapeutic index is also indicated by the term efficacy index). The example illustrated in FIG. 34 shows the time course of successful drug therapy of a disease state (such as atherosclerosis) that is indicated by three biochemical analytes represented by parameters A, B and C. The disease is treated (with for example a Statin) starting on day zero.

Parameters A, B and C are measured daily using an ambulatory system as described herein. At the outset, relative to "ideal levels", Parameter A (for example LDL-cholesterol) is elevated, Parameter B (for example HDL-cholesterol) is low and Parameter C (for example, alanine aminotransferase, an indicator of liver damage) is normal. All parameters (A, B, C) are presented normalized to their respective ideal level. As therapy proceeds, the drug causes the levels of A and B to approach normal values but at different rates. Analyte C remains normal indicating the drug is not causing liver damage. The relative risk of an outcome for the patient is represented by an initially unknown TI. As described above, TI is a surrogate to the outcome parameter that reflects the physiological functions of the patient (blood pressure, etc.) or other pre-identified factors in a patient record and can be indicative of improvement in the patient's condition. We further assume that parameter TI is influenced by parameters A and B. In certain cases, at the beginning of the study this relationship remains to be determined.

Figure 35:
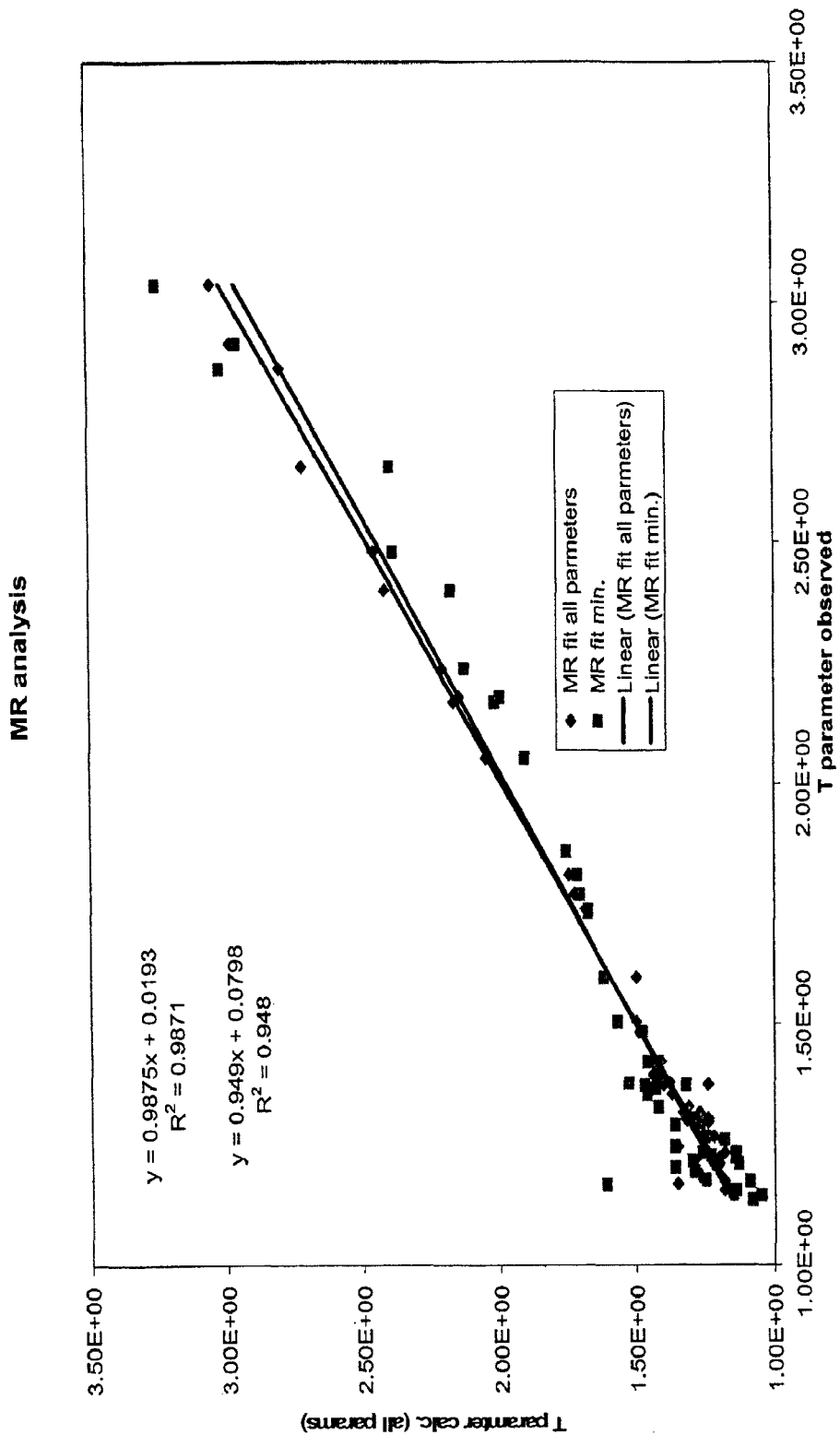
FIG. 35 shows multiple regression analysis of the computed therapeutic index.

Data from the monitoring system (device input) and the patient input are analyzed by multiple regression of TI and measured values A, B and C, as described above. In the example shown, these data are analyzed using multiple regression analysis, which fits parameter TI as a function of parameters A, B, C and their squares and the pair-wise cross terms (A*B, etc.) As shown in FIG. 35, for the simulated values shown in FIG. 34, an excellent fit was obtained ($R^2=0.99$) when all parameters were included. It is evident from inspection of the fit that most of the parameters can be eliminated leaving only A and A*B. When this is done the fit is still very good ($R^2=0.95$).

The multiple regression derived function is not identical to the base function which generated the first candidate TI data, but works well to compute an estimate of TI from (typically fewer) measured parameters, prior to clinical validation, if necessary. The appropriate threshold levels of TI, or the optimum TI is termed as $TI_{ref}$ (or "action threshold value".) Expert review can then determine the optimum therapeutic index for that particular patient or patient class. If the computed TI exceeds the preset $TI_{ref}$, appropriate action can be taken. An appropriate action could be alerting the physician, stopping the medication or the like. As can be understood, the appropriate $TI_{ref}$ for a patient would be decided based on the healthcare provider's judgment for that individual patient. The form of the TI is derived as a one time exercise using expert analysis of the data set derived from clinical studies and/or existing clinical information.

Figure 36:
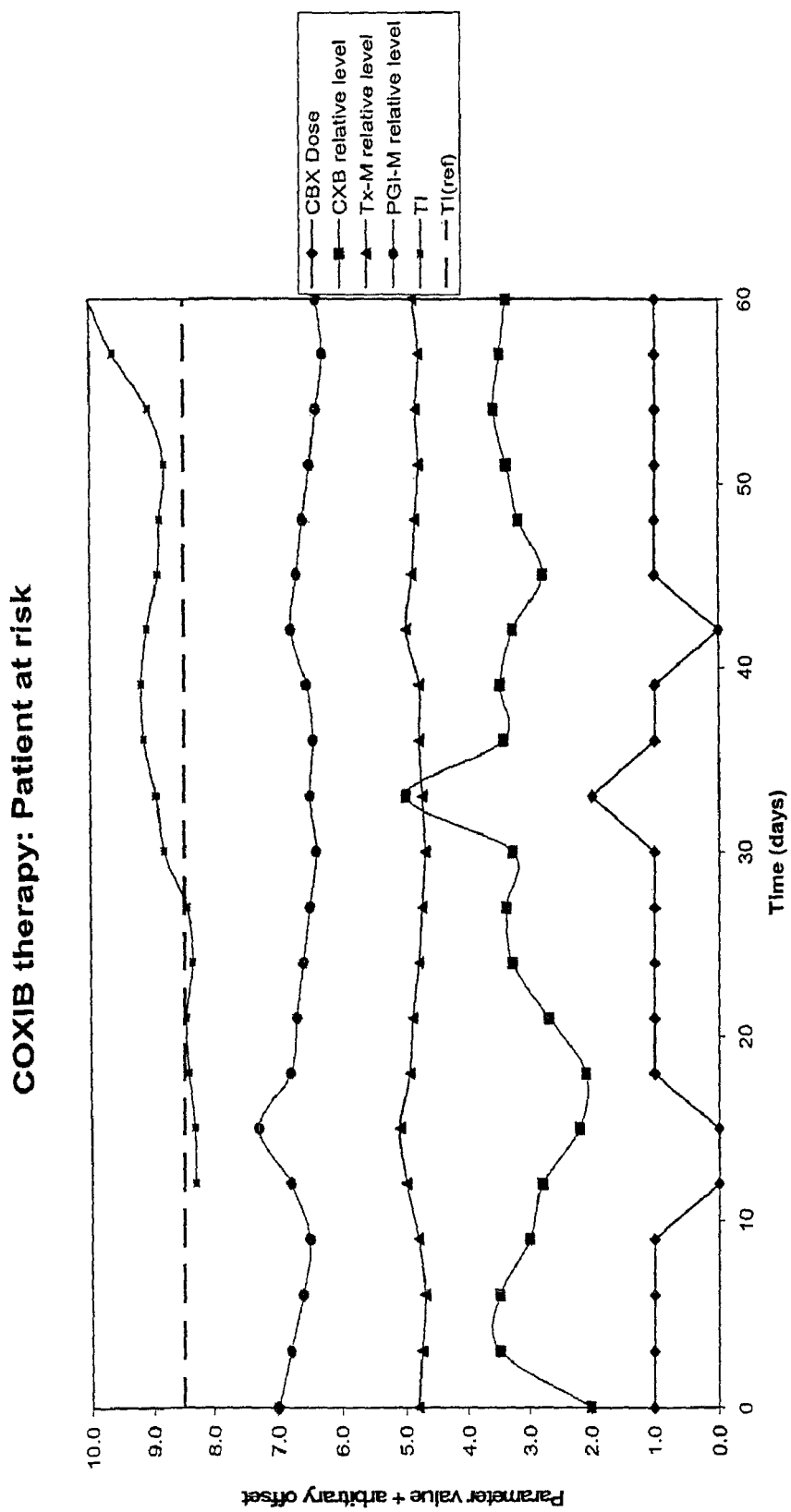
FIG. 36 is an illustration of the relationship between measured drug, analyte and biomarker concentration and therapeutic index.

Once the $TI_{ref}$ is identified, then the use of this parameter is illustrated in FIG. 36. Methods of measuring drug, analyte and biomarker concentrations and conducting a two-way communication with a database using a fluidic device and reader assembly are described in detail herein. The time course of various measured and computed parameters are shown in FIG. 36. The curve indicated CBX Dose illustrates the time course of a drug that is taken on a regular basis. The plotted values are normalized to what would be considered as "ideal levels" for that measurement. For example, if the expected ideal blood concentration of CBX is 100 ng/ml and if the measured concentration in blood is 100 ng/ml, the parameter value is 1.0 (with no offset) for CBX. Similarly, the concentrations of CXB, a metabolite of CBX, biomarkers Tx-M and PGI-M, which vary in response to the concentrations of the drug and the disease state, are also normalized to their ideal values and plotted. All the drug, analyte and biomarker concentrations could be measured using a system as described herein. As explained above, the $TI_{ref}$ for this particular patient is plotted on FIG. 36 as a flat line. Using the parameter values (a ... n, aa ... nn, aaa ... nnn) of Equation 6 and the measured input parameters (IP), the current TI for the patient is calculated. If the computed TI exceeds the $TI_{ref}$ value, then an alert can be generated. The alert could be targeted to the patient's healthcare provider, who in turn can take the appropriate action. An appropriate action could be to watch the patient closely for other clinical indications and/or alter the dosage and drugs the patient is taking.

Figure 37:
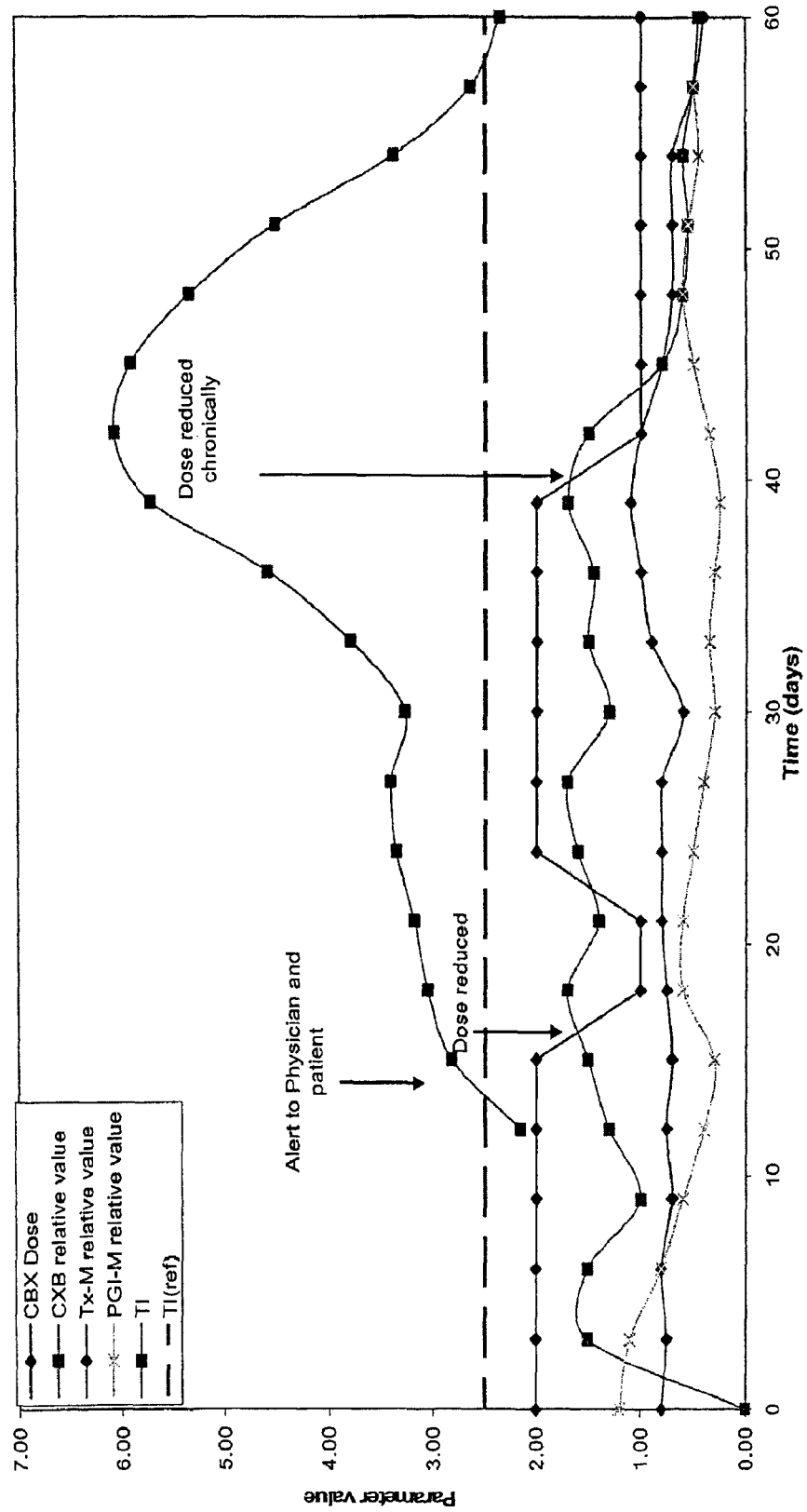
FIG. 37 is an illustration of the application of this invention to minimize adverse drug reactions.

FIGS. 36 and 37 illustrate the concept as to how when the computed TI exceeds the $TI_{ref}$ a proactive action could avert an ADR. In FIG. 36, the patient's TI exceeded $TI_{ref}$ about day 15. The patient is monitored closely and as the TI values continue to increase after day 30, the physician intervenes and reduces the dosage. This action starts lowering the TI for the patient and ultimately retreats to an acceptable level about day 60.

One or more individuals or entities that are involved in the care of the patient (nurses, physicians, pharmacist, etc.) can be alerted when the computed TI exceeds the $TI_{ref}$ so that they could take the appropriate action. Additionally, trends can be discerned and appropriate action taken before a TI reaches a particular value.

In some embodiments many different analytes can be measured and construed as input parameters, IPs, while computing the TI. Such analytes that may be used are described herein. Additionally, the can be expanded or modified depending on the disease area as well. The appropriate list of parameters relating to certain diseases and drug treatments, for example, cancer and infectious diseases and patient on NSAIDS, are disclosed herein.

In another aspect of this invention, the TI is calculated using information derived from the patient's biological sample and patient information that is non-drug related, the device input. For example, in an ambulatory setting, information relating to concentration of drug, metabolite and other biological markers can be detected in blood as described herein. The patient can also input many non-drug related personal parameters. This "patient input" can relate to the patient's personal information, for example, height, weight, gender, daily exercise status, food intake, etc. The patient input could also be provided by the patient's healthcare provider. An example of a patient input parameter and the input means is shown in FIG. 38.

In some embodiments the device input and patient input are used to compute the TI. A reference TI for the patient is already known using retrospective analysis of the data contained in the database. In formulating the TI using multiple regression analysis, the parameters such as those shown in Equation 6 are used. The same parameters are then used with the device input and patient input to compute the TI. Comparing the TI to the $TI_{ref}$ it is possible to determine the efficacy of the therapy. If the TI falls within a pre-determined range of $TI_{ref}$, then the treatment is considered to be efficacious. Values below that range indicate that the treatment is ineffective and values higher then the range are considered to be undesirable and could lead to adverse events.

Another example illustrates the implementation of this invention for studying the efficacy of therapy in diseases where it is difficult to make frequent measurements and the efficacy of the treatment is difficult to quantify. An example is determining the efficacy of drug therapy in children with autism. Frequent sampling and concomitant laboratory analysis is impractical for children. Abnormalities in blood concentrations of certain metals are implicated in autism. Hence, following the blood concentration of certain metals, e.g., zinc, in autistic children might shed light on the efficacy of an intervention. However, it has been reported that lowered concentrations of, say, Zn due to a treatment does not imply that the therapy is working. It is an indicator, but not a definitive surrogate for determining therapeutic efficacy. Computing a TI and comparing it to a reference level would better indicate the efficacy. This is illustrated in FIG. 39 by simulating the concentration of various pertinent markers and their change due to a drug intervention in an autistic child.

The program can involve monitoring subjects and matched control individuals over time for toxic metals, surrogate markers for metals (metallothionein, etc.), and other biochemical markers. Subjects are those prone to, or afflicted with autism; controls are situation-matched people. It is not mandatory that there be a situation-matched control. The scenario assumes that during the study a significant "event" occurs. Events could be movement into a more or less risky environment or initiation of therapy. Subjects could be frequently monitored for several parameters (device input) using the ambulatory system described herein. Additional laboratory assays that are not determinable in the ambulatory system could be performed at a lower frequency using laboratory assays. Additional data such as patient information, local environment, use of drugs, diet, etc. would be logged (patient input). Of particular interest to this scenario is information such as exposure to lead, mercury etc.

Figure 39:
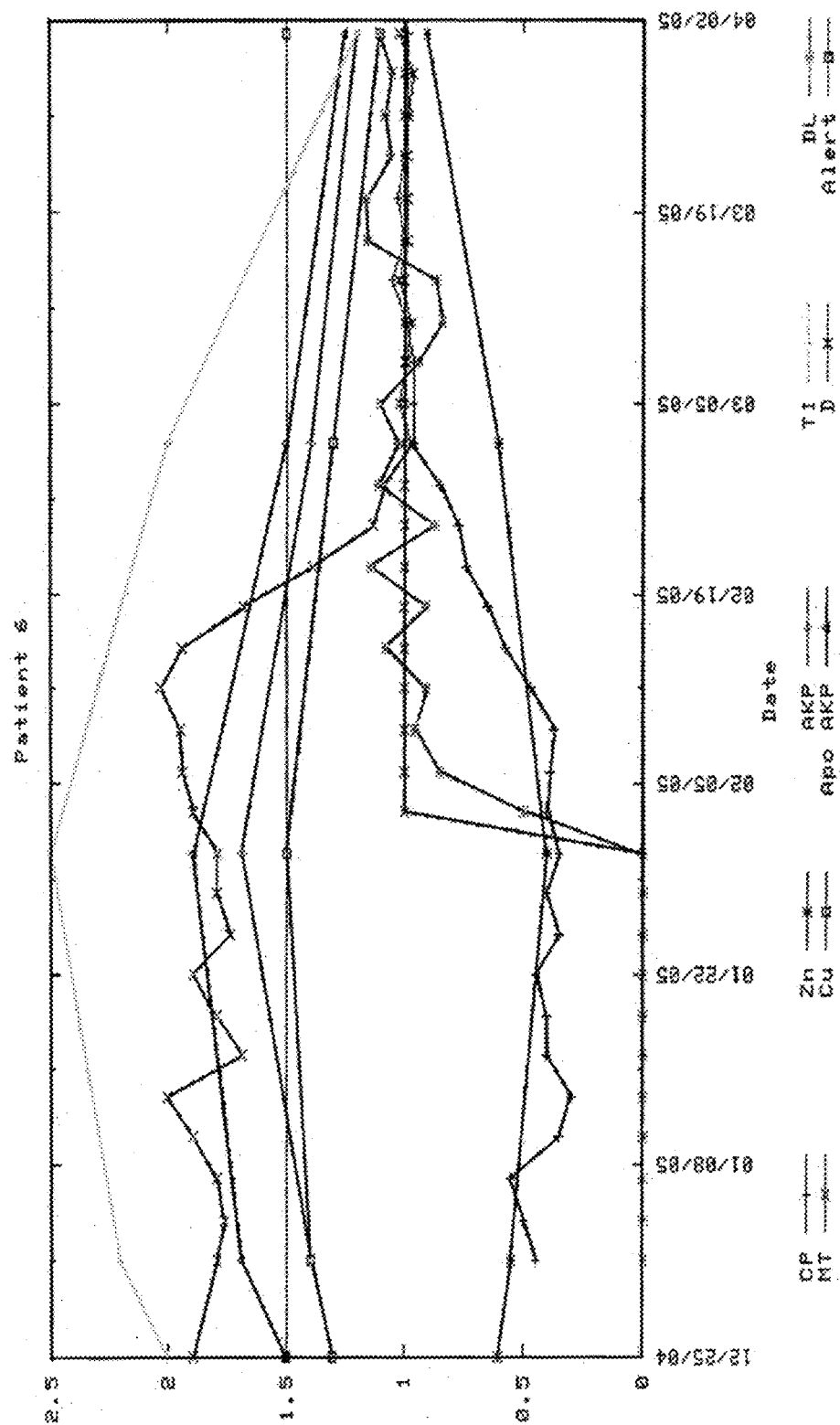
FIG. 39 shows use of a therapeutic index to follow treatment progression in an autism patient.

The time course shown in FIG. 39 envisages an event (initiation of therapy) at 33 days. The subject who is exhibiting abnormal levels of CP and MT, gradually reverts to normal levels of markers. The TI captures the risk or safety level of the subject based on all information. The study will define the best inputs to determine TI.

As described above, TI can be used for determining the efficacy of drug treatment. A similar approach is also well suited for determining the efficacy of drugs during clinical trials. Additionally, this approach could be beneficially used to identify sub-groups of patients who respond well or poorly to a given treatment regimen. The ability to segregate responders from non-responders is an extremely valuable tool. The concept of using TI can be used not only during a therapeutic regimen, but for performing diagnostic tests to determine, for example, whether or not a patient is in need of a biopsy after a complete examination of prostate specific markers.

TABLE 4

| | Exemplary Analyates |
|---|---|
| Liver | LDH, (LD5), (ALT), Arginase 1 (liver type), Alpha-fetoprotein (AFP), Alkaline phosphatase, Alanine aminotransferase, Lactate dehydrogenase, and Bilirubin |
| Kidney | TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP) |
| Heart | Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I) |
| Pancrease | Amylase, Pancreatitis-Assocoated protein (PAP-1), and Regeneratein proteins (REG) |
| Muscle tissue | Myostatin |
| Blood | Erythopoeitin (EPO) |
| Bone | Cross-linked N-telopeptides of bone type I collagen (NTx) Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone gla-protein), Alkaline phosphatase, Cathepsin K, COMP (Cartillage Oligimeric Matrix Protein), Osteocrin Osteoprotegerin (OPG), RANKL, sRANK, TRAP 5 (TRACP 5), Osteoblast Specific Factor 1 (OSF-1, Pleiotrophin), Soluble cell adhesion molecules (SCAMs), sTfR, sCD4, sCD8, sCD44, and Osteoblast Specific Factor 2 (OSF-2, Periostin) |
| Cancer | PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP) , hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit, KDR or Flt-1, KDR, AML, and Midkine |

TABLE 4-continued

| | Exemplary Analyates |
|---|---|
| Infectious disease | Viremia, Bacteremia, Sepsis, PMN Elastase, PMN elastase/α1-PI complex, Surfactant Protein D (SP-D), HBVc antigen, HBVs antigen, Anti-HBVc, Anti-HIV, T-supressor cell antigen, T-cell antigen ratio, T-helper cell antigen, Anti-HCV, Pyrogens, p24 antigen, Muramyl-dipeptide |
| Diabetes | C-Peptide, Hemoglobin A1c, Glycated albumin, Advanced glycosylation end products (AGEs), 1,5-anhydroglucitol, Gastric Inhibitory Polypeptide, Glucose, Hemoglobin, ANGPTL3 and 4 |
| Inflamation | Rheumatoid factor (RF), Antinuclear Antibody (ANA), C-reactive protein (CRP), Clara Cell Protein (Uteroglobin) |
| Allergy | Total IgE and Specific IgE |
| Autism | Ceruloplasmin, Metalothioneine, Zinc, Copper, B6, B12, Glutathione, Alkaline phosphatase, and activation of apo-alkaline phosphatase |
| Coagulation disorders | b-Thromboglobulin, Platelet factor 4, Von Willebrand factor |
| COX inhibitors | TxB2 (Cox-1), 6-keto-PGF-1-alpha (Cox 2), 11-Dehydro-TxB-1a (Cox-1) |
| Geriatric | Neuron-specific enolase, GFAP, and S100B |
| Nutritional status | Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4) Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, amd sTfR (soluble Transferrin Receptor) |
| Lipid metabolism | Apo-lipoproteins (several), Apo-A1, Apo-B, Apo-C-CII, Apo-D, Apo-E |
| Coagulation status | Factor I: Fibrinogen, Factor II: Prothrombin, Factor III: Tissue factor, Factor IV: Calcium, Factor V: Proaccelerin, Factor VI, Factor VII: Proconvertin, Factor VIII:, Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1). |
| Monoclonal antibodies | those for EGFR, ErbB2, and IGF1R |
| Tyrosine kinase inhibitors | Ab1, Kit, PDGFR, Src, ErbB2, ErbB 4, EGFR, EphB, VEGFR1-4, PDGFRb, FLt3, FGFR, PKC, Met, Tie2, RAF, and TrkA; VEGF |
| Serine/Threoline Kinase Inhibitors | AKT, Aurora A/B/B, CDK, CDK (pan), CDK1-2, VEGFR2, PDGFRb, CDK4/6, MEK1-2, mTOR, and PKC-beta |
| GPCR targets | Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors |
| Other | Theophylline, CRP, CKMB, PSA, Myoglobin, CA125, Progesterone, TxB2, 6-keto-PGF-1-alpha, and Theophylline, Estradiol, Lutenizing hormone, High sensitivity CRP, Triglycerides, Tryptase, Low density lipoprotein Cholesterol, High density lipoprotein Cholesterol, Cholesterol, IGFR, Leptin, Leptin receptor, and Pro-calcitonin, Brain S100 protein, Substance P, 8-Iso-PGF-2a; GIP; GLP-1 |

What is claimed is:

1. A method of detecting an analyte in a bodily fluid from a subject, comprising:
   a) providing a fluidic device comprising a cartridge, said cartridge comprising a sample collection unit and an assay assembly, wherein said sample collection unit is configured to collect a sample of bodily fluid from said subject, and wherein said assay assembly comprises at least one reaction site containing a reactant adapted to reacts with said analyte;
   b) metering a predetermined portion of said sample to be assayed in said sample collection unit;
   c) allowing said predetermined portion of sample to react with assay reagents contained within said assay assembly to yield a signal indicative of the presence of said analyte in said sample; and
   d) detecting said signal generated from said analyte collected in said sample of bodily fluid.

2. The method of claim 1, further comprising mixing said predetermined portion of said sample with a diluent in said fluidic device after the metering step.

3. The method of claim 2, wherein said mixing comprises diluting said predetermined portion of sample with said diluent to yield a diluted sample.

4. The method of claim 3, further comprising filtering said diluted sample before allowing said predetermined portion of sample to react with assay reagents.

5. The method of claim 3, wherein said assay assembly comprises at least one reagent chamber and an actuatable valve assembly configured to control flow of the reagents out of said reagent chamber and into said at least one reaction site.

6. The method of claim 5, further comprising actuating said actuatable valve assembly to permit said reagent to flow from said reagent chamber to said reaction site.

7. The method of claim 6, wherein said actuatable valve assembly comprises an actuator pin and a sealing ball, and said actuating comprising actuating said actuator pin to displace said sealing ball.

8. The method of claim 1, further comprising the step of quantifying the amount of said analyte present in said bodily fluid after said detecting step.

9. The method of claim 8, further comprising the step of comparing the amount of said analyte present in said biologic fluid to a predetermined amount of said analyte.

10. The method of claim 1, wherein said fluidic device communicates data relating to said signal via a wireless transmitter to an external device.

11. The method of claim 1, wherein the analyte detected is indicative of at least one pharmacological parameter.

12. The method of claim 11, further comprising cross-referencing medical records of said subject with the at least one pharmacological parameter to assistant a clinician in providing an individualized medical treatment.

13. The method of claim 4, wherein said filtering comprises removing red blood cells from the diluted sample.

* * * * *